US008247652B2

(12) United States Patent
Blau et al.

(10) Patent No.: US 8,247,652 B2
(45) Date of Patent: Aug. 21, 2012

(54) POPULATION OF TRANSGENIC PLANTS INDIVIDUALLY COMPRISING DISTINCT CODOGENIC GENE SEGMENTS, THE POPULATION HAVING AT LEAST 50% OF THE CODOGENIC GENE SEGMENTS FROM A DONOR ORGANISM

(75) Inventors: Astrid Blau, Stahnsdorf (DE); Mathieu Klein, Berlin (DE); Birgit Wendel, Berlin (DE)

(73) Assignee: Metanomics GmbH & Co. KGaA (DE)

( * ) Notice: Subject to any disclaimer, the term of this patent is extended or adjusted under 35 U.S.C. 154(b) by 50 days.

(21) Appl. No.: 10/508,264

(22) PCT Filed: Mar. 18, 2003

(86) PCT No.: PCT/EP03/02815
§ 371 (c)(1),
(2), (4) Date: Sep. 20, 2004

(87) PCT Pub. No.: WO03/077642
PCT Pub. Date: Sep. 25, 2003

(65) Prior Publication Data
US 2005/0155100 A1 Jul. 14, 2005

(30) Foreign Application Priority Data
Mar. 19, 2002 (DE) .................................. 102 12 158

(51) Int. Cl.
*C12N 15/82* (2006.01)
*A01H 5/00* (2006.01)
*A01H 1/00* (2006.01)

(52) U.S. Cl. ........ 800/298; 800/279; 800/281; 800/282; 800/283; 800/284; 800/288; 800/289; 800/290; 800/294; 800/295; 800/320.2; 435/468; 435/419; 435/69.1

(58) Field of Classification Search .................. None
See application file for complete search history.

(56) References Cited

U.S. PATENT DOCUMENTS

| 2002/0120955 A1 | 8/2002 | Sonnewald et al. | |
|---|---|---|---|
| 2003/0003585 A1 | 1/2003 | Kawasaki | |
| 2003/0221212 A1 * | 11/2003 | Tomes et al. | 800/278 |
| 2007/0022495 A1 * | 1/2007 | Reuber et al. | 800/279 |

FOREIGN PATENT DOCUMENTS

| CA | 2 348 888 A1 | 5/2000 |
|---|---|---|
| CA | 2 379 498 A1 | 1/2001 |
| EP | 0 335 528 A2 | 4/1989 |
| EP | 0 388 186 A1 | 9/1990 |
| WO | WO 94/12015 A1 | 6/1994 |
| WO | WO 95/14098 A1 | 5/1995 |
| WO | WO 97/06268 A2 | 2/1997 |
| WO | WO 99/36516 A2 | 7/1999 |
| WO | WO 00/12680 * | 3/2000 |
| WO | WO 01/36598 * | 1/2001 |
| WO | WO 01/07600 * | 2/2001 |
| WO | WO 01/07600 A1 | 2/2001 |

OTHER PUBLICATIONS

Hamilton et al. Stable transfer of intact high molecular weight DNA into plant chromosomes. (1996) PNAS, vol. 93, pp. 9975-9979.*
Lazo et al. A DNA transformation-competent *Arabidopsis* genomic library in Agrobacterium. (1991) Bio/Technology, vol. 9, pp. 963-967.*
Weigel et al. Activation Tagging in *Arabidopsis*. (2000) Plant Physiology, vol. 122, pp. 1003-1013.*
Lehninger et al. Principles of Biochemistry, 2nd Edition. (1993) p. 898.*
Thorsness et al. Genetic Ablation of Floral Cells in *Arabidopsis*. (1993) The Plant Cell, vol. 5, pp. 253-261.*
ORF—Definition; "Open Reading Frame"; Biology-Online, p. 1 of 1.*
Schloss J.A. and Croom H.B. Normal Chlamydomonas nuclear gene structure on linkage group XIX. (1991) J. of Cell Science; vol. 100, pp. 877-881.*
Kaneko et al. Structural analysis of *Arabidopsis thaliana* chromosome 5. V. sequence features of the regions of 1,381,565 bp covered by twenty one physically assigned P1 and TAC clones. (1998) DNA Research; vol. 5, pp. 131-145.*
Kohchi et al. Construction of an equalized cDNA library from *Arabidopsis thaliana*. (1995) The Plant Journal; vol. 8; pp. 771-776.*
LeClere et al. A library of *Arabidopsis* 35S-cDNA lines for identifying novel mutants. (2001) PMB; vol. 46; pp. 695-703.*
The *Arabidopsis* Genome Initiative; Analysis of the genome sequence of the flowering plant *Arabidopsis thaliana* (2000) Nature; vol. 408; pp. 796-815.*
Varotto et al. GST-PRIME: a genome-wide primer design software for the generation of gene sequence tags. (2001) Nucleic Acids Research; vol. 29; pp. 4373-4377.*
McCubbin, A., et al., "Construction of a Binary Bacterial Artificial Chromosome Library of *Petunia inflata* and the Isolation of Large Genomic Fragments Linked to the Self-Incompatatibility (S–) Locus", Genome, vol. 43, 2000, pp. 820-826.

(Continued)

*Primary Examiner* — Cathy Kingdon Worley
(74) *Attorney, Agent, or Firm* — Connolly Bove Lodge & Hutz LLP

(57) ABSTRACT

The present invention relates to populations of trangenic plants encompassing a substantial part of all codogenic gene segments of a donor organism, and to biological material derived therefrom, plasmid collections and populations of transformed host organisms with which plants can be transformed in a suitable manner. There are also described methods for generating the plants and the material, and the use of the plants and of the material for functional studies. The codogenic gene segments are integrated into the genome of the plants. For example, there are described a population of plants of the species *Arabidopsis thaliana* into whose genome the codogenic gene segments from *Saccharomyces cerevisiae* are integrated, and their morphological analysis under normal conditions and stress conditions.

27 Claims, 44 Drawing Sheets

OTHER PUBLICATIONS

Hamilton, C. et al., "Stable Transfer of Intact High Molecular Weight DNA into Plant Chromosomes", Proc. Natl. Acad. Sci. USA, vol. 93, 1996, pp. 9975-9979.

Frary, A., et al., "Efficiency and Stability of High Molecular Weight DNA transformation: An Analysis in Tomato", Transgenic Research, vol. 10, 2001, pp. 121-132.

Stoesser, G., et al., "The EMBL Nucleotide Sequence Database", Nucleic Acids Research, vol. 29, No. 1, 2001, pp. 17-21.

Benson, D., et al., "GenBank", Nucleic Acids Research, vol. 28, No. 1, 2000, pp. 15-18.

Barker, W. C., et al., "The PIR-International Protein Sequence Database", Nucleic Acids Research, vol. 27, No. 1, 1999, pp. 39-43.

Cherry, J. M., et al., "SGD: *Saccharomyces* Genome Database", Nucleic Acids Research, vol. 26, No. 1, 1998, pp. 73-79.

Mewes, H. W., et al, "MIPS: A Database for Genomes and Protein Sequences", Nucleic Acids Research, vol. 27, No. 1, 1999, pp. 44-48.

Huala, E., et al., "The *Arabidopsis* Information Resource (TAIR): A Comprehensive Database and Web-Based Information Retrieval, Analysis, and Visualization System for a Model Plant", Nucleic Acids Research, vol. 29, No. 1, 2001, pp. 102-105.

Hellens, R. et al., "A Guide to *Agrobacterium* Binary Ti Vectors", Trends in Plant Science, vol. 5, No. 10, 2000, pp. 446-451.

Clough, S. J., et al., "Flora Dip: A Simplified Method for *Agrobacterium*-mediated Transformation of *Arabidopsis thaliana*;" The Plant Journal, vol. 16, No. 6, 1998, pp. 735-743.

Koncz, C., et al., "The Promoter of $T_L$-DNA Gene 5 Controls the Tissue-Specific Expression of Chimaeric Genes Carried by a Novel Type of *Agrobacterium* Binary Vector", Mol. Gen. Genet., vol. 204, 1986, pp. 383-396.

Mewes, H. W., et al., "Overview of the Yeast Genome", Nature, vol. 387, 1997, pp. 7-8.

* cited by examiner

| | | | | |
|---|---|---|---|---|
| YAL002W | YAL044C | YAR027W | YBL019W | YBL065W |
| YAL003W | YAL045C | YAR028W | YBL021C | YBL066C |
| YAL005C | YAL046C | YAR029W | YBL022C | YBL067C |
| YAL007C | YAL047C | YAR030C | YBL025W | YBL069W |
| YAL008W | YAL048C | YAR031W | YBL026W | YBL070C |
| YAL009W | YAL049C | YAR033W | YBL027W | YBL071C |
| YAL010C | YAL051W | YAR035W | YBL028C | YBL072C |
| YAL011W | YAL053W | YAR042W | YBL030C | YBL073W |
| YAL012W | YAL054C | YAR044W | YBL031W | YBL074C |
| YAL013W | YAL055W | YAR047C | YBL032W | YBL075C |
| YAL014C | YAL056W | YAR053W | YBL033C | YBL076C |
| YAL015C | YAL058C-A | YAR060C | YBL035C | YBL077W |
| YAL016W | YAL058W | YAR061W | YBL036C | YBL078C |
| YAL018C | YAL059W | YAR062W | YBL037W | YBL080C |
| YAL019W | YAL060W | YAR064W | YBL038W | YBL082C |
| YAL020C | YAL061W | YAR066W | YBL039C | YBL083C |
| YAL022C | YAL062W | YAR068W | YBL041W | YBL086C |
| YAL023C | YAL064W | YAR069C | YBL043W | YBL087C |
| YAL025C | YAL064W-B | YAR070C | YBL044W | YBL089W |
| YAL027W | YAL065C | YAR071W | YBL045C | YBL090W |
| YAL028W | YAL066W | YAR073W | YBL046W | YBL091C |
| YAL030W | YAL067C | YAR075W | YBL048W | YBL091C-A |
| YAL031C | YAL068C | YBL001C | YBL049W | YBL092W |
| YAL032C | YAL069W | YBL002W | YBL050W | YBL093C |
| YAL033W | YAR002W | YBL003C | YBL053W | YBL094C |
| YAL034C | YAR003W | YBL005W-A | YBL054W | YBL095W |
| YAL034W-A | YAR007C | YBL006C | YBL055C | YBL096C |
| YAL035C-A | YAR008W | YBL007C | YBL056W | YBL097W |
| YAL036C | YAR010C | YBL008W | YBL057C | YBL098W |
| YAL037W | YAR014C | YBL010C | YBL059W | YBL099W |
| YAL038W | YAR015W | YBL011W | YBL060W | YBL100C |
| YAL039C | YAR018C | YBL012C | YBL061C | YBL101C |
| YAL040C | YAR019C | YBL013W | YBL062W | YBL101W-A |
| YAL041W | YAR020C | YBL016W | YBL063W | YBL102W |
| YAL042W | YAR023C | YBL018C | YBL064C | YBL103C |

FIG. 1A

| | | | | |
|---|---|---|---|---|
| YBL104C | YBR029C | YBR066C | YBR110W | YBR149W |
| YBL106C | YBR030W | YBR067C | YBR111C | YBR151W |
| YBL107C | YBR031W | YBR068C | YBR112C | YBR152W |
| YBL107W-A | YBR032W | YBR069C | YBR113W | YBR153W |
| YBL108W | YBR033W | YBR071W | YBR114W | YBR154C |
| YBL109W | YBR034C | YBR072W | YBR115C | YBR155W |
| YBL111C | YBR035C | YBR074W | YBR116C | YBR156C |
| YBL112C | YBR036C | YBR075W | YBR117C | YBR157C |
| YBL113C | YBR037C | YBR076W | YBR118W | YBR158W |
| YBR001C | YBR038W | YBR077C | YBR119W | YBR159W |
| YBR002C | YBR039W | YBR083W | YBR120C | YBR160W |
| YBR003W | YBR040W | YBR084C-A | YBR121C | YBR161W |
| YBR004C | YBR041W | YBR084W | YBR122C | YBR162C |
| YBR005W | YBR042C | YBR085W | YBR123C | YBR162W-A |
| YBR006W | YBR043C | YBR086C | YBR124W | YBR163W |
| YBR007C | YBR044C | YBR087W | YBR125C | YBR164C |
| YBR009C | YBR045C | YBR088C | YBR126C | YBR166C |
| YBR010W | YBR046C | YBR089C-A | YBR127C | YBR167C |
| YBR011C | YBR047W | YBR089W | YBR128C | YBR168W |
| YBR012C | YBR048W | YBR090C | YBR129C | YBR169C |
| YBR012W-A | YBR049C | YBR091C | YBR130C | YBR170C |
| YBR013C | YBR050C | YBR092C | YBR131W | YBR171W |
| YBR014C | YBR051W | YBR093C | YBR132C | YBR173C |
| YBR015C | YBR052C | YBR094W | YBR133C | YBR174C |
| YBR016W | YBR053C | YBR095C | YBR134W | YBR175W |
| YBR017C | YBR054W | YBR096W | YBR135W | YBR176W |
| YBR018C | YBR055C | YBR098W | YBR137W | YBR177C |
| YBR019C | YBR056W | YBR099C | YBR138C | YBR178W |
| YBR020W | YBR057C | YBR100W | YBR139W | YBR181C |
| YBR021W | YBR058C | YBR101C | YBR141C | YBR182C |
| YBR022W | YBR059C | YBR102C | YBR142W | YBR183W |
| YBR023C | YBR060C | YBR103W | YBR143C | YBR184W |
| YBR024W | YBR061C | YBR104W | YBR144C | YBR185C |
| YBR025C | YBR062C | YBR106W | YBR145W | YBR186W |
| YBR026C | YBR063C | YBR107C | YBR146W | YBR187W |
| YBR027C | YBR064W | YBR108W | YBR147W | YBR188C |
| YBR028C | YBR065C | YBR109C | YBR148W | YBR189W |

FIG. 1B

| | | | | |
|---|---|---|---|---|
| YBR190W | YBR236C | YBR274W | YCL014W | YCL074W |
| YBR191W | YBR237W | YBR276C | YCL016C | YCL075W |
| YBR192W | YBR238C | YBR277C | YCL017C | YCL076W |
| YBR193C | YBR239C | YBR278W | YCL018W | YCR001W |
| YBR194W | YBR240C | YBR279W | YCL019W | YCR002C |
| YBR195C | YBR241C | YBR280C | YCL020W | YCR003W |
| YBR196C | YBR242W | YBR281C | YCL022C | YCR004C |
| YBR197C | YBR243C | YBR282W | YCL023C | YCR005C |
| YBR198C | YBR244W | YBR283C | YCL024W | YCR006C |
| YBR199W | YBR245C | YBR284W | YCL025C | YCR007C |
| YBR200W | YBR246W | YBR285W | YCL027W | YCR008W |
| YBR204C | YBR247C | YBR286W | YCL029C | YCR009C |
| YBR205W | YBR248C | YBR287W | YCL031C | YCR010C |
| YBR206W | YBR249C | YBR288C | YCL032W | YCR012W |
| YBR207W | YBR250W | YBR289W | YCL034W | YCR013C |
| YBR209W | YBR251W | YBR290W | YCL038C | YCR014C |
| YBR210W | YBR252W | YBR291C | YCL039W | YCR015C |
| YBR211C | YBR253W | YBR292C | YCL040W | YCR016W |
| YBR213W | YBR254C | YBR293W | YCL043C | YCR019W |
| YBR214W | YBR255W | YBR294W | YCL048W | YCR020C |
| YBR217W | YBR256C | YBR295W | YCL049C | YCR020C-A |
| YBR218C | YBR257W | YBR296C | YCL050C | YCR020W-B |
| YBR219C | YBR258C | YBR297W | YCL051W | YCR021C |
| YBR221C | YBR259W | YBR298C | YCL052C | YCR022C |
| YBR222C | YBR260C | YBR299W | YCL054W | YCR023C |
| YBR223C | YBR261C | YBR300C | YCL055W | YCR024C |
| YBR225W | YBR262C | YBR301W | YCL056C | YCR024C-A |
| YBR226C | YBR263W | YBR302C | YCL057W | YCR025C |
| YBR227C | YBR264C | YCL001W-A | YCL058C | YCR027C |
| YBR228W | YBR265W | YCL002C | YCL059C | YCR028C |
| YBR229C | YBR266C | YCL005W | YCL064C | YCR028C-A |
| YBR230C | YBR268W | YCL006C | YCL065W | YCR030C |
| YBR231C | YBR269C | YCL007C | YCL066W | YCR034W |
| YBR232C | YBR270C | YCL008C | YCL067C | YCR035C |
| YBR233W | YBR271W | YCL009C | YCL068C | YCR037C |
| YBR234C | YBR272C | YCL011C | YCL069W | YCR039C |
| YBR235W | YBR273C | YCL012W | YCL073C | YCR041W |

FIG. 1C

| | | | | |
|---|---|---|---|---|
| YCR043C | YCR097W | YDL037C | YDL085W | YDL130W |
| YCR044C | YCR099C | YDL040C | YDL086W | YDL130W-A |
| YCR045C | YCR100C | YDL041W | YDL088C | YDL131W |
| YCR046C | YCR101C | YDL043C | YDL089W | YDL132W |
| YCR047C | YCR102C | YDL045C | YDL090C | YDL133C-A |
| YCR048W | YCR102W-A | YDL045W-A | YDL091C | YDL133W |
| YCR049C | YCR103C | YDL047W | YDL092W | YDL134C |
| YCR050C | YCR104W | YDL048C | YDL093W | YDL135C |
| YCR051W | YCR105W | YDL049C | YDL094C | YDL136W |
| YCR053W | YCR107W | YDL050C | YDL096C | YDL137W |
| YCR054C | YDL001W | YDL051W | YDL097C | YDL139C |
| YCR059C | YDL002C | YDL052C | YDL098C | YDL142C |
| YCR060W | YDL003W | YDL053C | YDL100C | YDL143W |
| YCR061W | YDL004W | YDL054C | YDL101C | YDL144C |
| YCR062W | YDL005C | YDL055C | YDL103C | YDL146W |
| YCR063W | YDL006W | YDL056W | YDL104C | YDL147W |
| YCR064C | YDL008W | YDL057W | YDL105W | YDL148C |
| YCR065W | YDL009C | YDL059C | YDL106C | YDL149W |
| YCR066W | YDL010W | YDL060W | YDL107W | YDL150W |
| YCR069W | YDL011C | YDL062W | YDL108W | YDL151C |
| YCR071C | YDL013W | YDL064W | YDL109C | YDL152W |
| YCR072C | YDL014W | YDL065C | YDL110C | YDL153C |
| YCR073W-A | YDL015C | YDL066W | YDL111C | YDL154W |
| YCR077C | YDL016C | YDL067C | YDL115C | YDL155W |
| YCR079W | YDL017W | YDL068W | YDL116W | YDL156W |
| YCR083W | YDL018C | YDL069C | YDL117W | YDL157C |
| YCR084C | YDL019C | YDL070W | YDL118W | YDL158C |
| YCR085W | YDL020C | YDL071C | YDL119C | YDL159W |
| YCR086W | YDL023C | YDL072C | YDL120W | YDL160C |
| YCR087C-A | YDL024C | YDL076C | YDL122W | YDL161W |
| YCR088W | YDL025C | YDL078C | YDL123W | YDL162C |
| YCR090C | YDL026W | YDL079C | YDL124W | YDL163W |
| YCR091W | YDL027C | YDL080C | YDL125C | YDL164C |
| YCR092C | YDL029W | YDL081C | YDL126C | YDL165W |
| YCR094W | YDL033C | YDL082W | YDL127W | YDL166C |
| YCR095C | YDL034W | YDL083C | YDL128W | YDL167C |
| YCR096C | YDL036C | YDL084W | YDL129W | YDL168W |

FIG. 1D

| | | | | |
|---|---|---|---|---|
| YDL169C | YDL212W | YDR007W | YDR048C | YDR089W |
| YDL170W | YDL213C | YDR008C | YDR049W | YDR090C |
| YDL172C | YDL215C | YDR009W | YDR050C | YDR091C |
| YDL173W | YDL216C | YDR010C | YDR051C | YDR092W |
| YDL174C | YDL217C | YDR012W | YDR052C | YDR094W |
| YDL177C | YDL218W | YDR013W | YDR053W | YDR095C |
| YDL178W | YDL219W | YDR016C | YDR054C | YDR096W |
| YDL179W | YDL220C | YDR018C | YDR055W | YDR098C-A |
| YDL180W | YDL221W | YDR019C | YDR056C | YDR100W |
| YDL181W | YDL222C | YDR020C | YDR057W | YDR101C |
| YDL182W | YDL223C | YDR021W | YDR058C | YDR103W |
| YDL183C | YDL224C | YDR022C | YDR060W | YDR104C |
| YDL184C | YDL226C | YDR024W | YDR061W | YDR106W |
| YDL186W | YDL227C | YDR025W | YDR062W | YDR108W |
| YDL187C | YDL228C | YDR026C | YDR063W | YDR109C |
| YDL188C | YDL230W | YDR027C | YDR064W | YDR110W |
| YDL190C | YDL233W | YDR029W | YDR065W | YDR112W |
| YDL191W | YDL234C | YDR030C | YDR066C | YDR116C |
| YDL192W | YDL235C | YDR031W | YDR067C | YDR118W |
| YDL193W | YDL236W | YDR032C | YDR068W | YDR120C |
| YDL195W | YDL237W | YDR033W | YDR070C | YDR122W |
| YDL196W | YDL238C | YDR034C | YDR071C | YDR123C |
| YDL197C | YDL239C | YDR034C-A | YDR072C | YDR125C |
| YDL198C | YDL240W | YDR034C-C | YDR073W | YDR128W |
| YDL199C | YDL241W | YDR034W-B | YDR074W | YDR130C |
| YDL200C | YDL242W | YDR035W | YDR075W | YDR131C |
| YDL201W | YDL243C | YDR036C | YDR077W | YDR132C |
| YDL202W | YDL244W | YDR037W | YDR078C | YDR134C |
| YDL203C | YDL246C | YDR038C | YDR079W | YDR136C |
| YDL204W | YDL247W | YDR040C | YDR080W | YDR137W |
| YDL205C | YDL248W | YDR041W | YDR082W | YDR138W |
| YDL206W | YDR001C | YDR042C | YDR083W | YDR139C |
| YDL207W | YDR002W | YDR043C | YDR084C | YDR141C |
| YDL208W | YDR003W | YDR044W | YDR085C | YDR142C |
| YDL209C | YDR004W | YDR045C | YDR086C | YDR143C |
| YDL210W | YDR005C | YDR046C | YDR087C | YDR144C |
| YDL211C | YDR006C | YDR047W | YDR088C | YDR145W |

FIG. 1E

| | | | | |
|---|---|---|---|---|
| YDR146C | YDR205W | YDR252W | YDR297W | YDR340W |
| YDR148C | YDR206W | YDR253C | YDR298C | YDR341C |
| YDR149C | YDR207C | YDR254W | YDR299W | YDR342C |
| YDR152W | YDR208W | YDR255C | YDR300C | YDR343C |
| YDR156W | YDR209C | YDR256C | YDR302W | YDR344C |
| YDR158W | YDR210W | YDR258C | YDR303C | YDR346C |
| YDR160W | YDR210W-A | YDR259C | YDR304C | YDR347W |
| YDR161W | YDR210W-C | YDR260C | YDR305C | YDR348C |
| YDR162C | YDR211W | YDR261C | YDR307W | YDR349C |
| YDR163W | YDR212W | YDR261C-C | YDR308C | YDR350C |
| YDR165W | YDR214W | YDR261W-A | YDR310C | YDR351W |
| YDR167W | YDR215C | YDR262W | YDR311W | YDR353W |
| YDR168W | YDR216W | YDR266C | YDR312W | YDR354W |
| YDR169C | YDR217C | YDR269C | YDR313C | YDR355C |
| YDR170W-A | YDR218C | YDR270W | YDR314C | YDR357C |
| YDR173C | YDR219C | YDR271C | YDR315C | YDR358W |
| YDR174W | YDR220C | YDR272W | YDR316W | YDR359C |
| YDR175C | YDR222W | YDR273W | YDR316W-A | YDR360W |
| YDR178W | YDR223W | YDR274C | YDR317W | YDR363W-A |
| YDR179C | YDR224C | YDR275W | YDR318W | YDR364C |
| YDR179W-A | YDR225W | YDR276C | YDR319C | YDR365W-A |
| YDR183W | YDR230W | YDR277C | YDR320C | YDR367W |
| YDR185C | YDR232W | YDR278C | YDR321W | YDR368W |
| YDR187C | YDR235W | YDR279W | YDR322C-A | YDR370C |
| YDR188W | YDR236C | YDR280W | YDR322W | YDR371W |
| YDR189W | YDR238C | YDR281C | YDR324C | YDR372C |
| YDR190C | YDR239C | YDR282C | YDR325W | YDR373W |
| YDR191W | YDR240C | YDR284C | YDR327W | YDR374C |
| YDR193W | YDR242W | YDR286C | YDR328C | YDR375C |
| YDR194C | YDR243C | YDR287W | YDR329C | YDR376W |
| YDR195W | YDR244W | YDR288W | YDR330W | YDR377W |
| YDR196C | YDR245W | YDR289C | YDR331W | YDR378C |
| YDR197W | YDR246W | YDR290W | YDR332W | YDR379W |
| YDR198C | YDR247W | YDR292C | YDR333C | YDR380W |
| YDR199W | YDR248C | YDR294C | YDR336W | YDR382W |
| YDR200C | YDR249C | YDR295C | YDR337W | YDR383C |
| YDR202C | YDR250C | YDR296W | YDR338C | YDR384C |

FIG. 1F

| | | | | |
|---|---|---|---|---|
| YDR385W | YDR439W | YDR481C | YDR521W | YEL016C |
| YDR386W | YDR440W | YDR482C | YDR522C | YEL017C-A |
| YDR387C | YDR441C | YDR483W | YDR523C | YEL017W |
| YDR388W | YDR442W | YDR484W | YDR524C | YEL018W |
| YDR389W | YDR444W | YDR485C | YDR525W-A | YEL019C |
| YDR390C | YDR445C | YDR486C | YDR526C | YEL020C |
| YDR391C | YDR446W | YDR487C | YDR527W | YEL020W-A |
| YDR392W | YDR447C | YDR488C | YDR528W | YEL021W |
| YDR394W | YDR448W | YDR489W | YDR529C | YEL024W |
| YDR395W | YDR449C | YDR490C | YDR530C | YEL026W |
| YDR396W | YDR450W | YDR491C | YDR531W | YEL027W |
| YDR397C | YDR451C | YDR492W | YDR532C | YEL028W |
| YDR399W | YDR453C | YDR493W | YDR533C | YEL029C |
| YDR400W | YDR454C | YDR494W | YDR534C | YEL030W |
| YDR401W | YDR455C | YDR496C | YDR535C | YEL032W |
| YDR402C | YDR456W | YDR497C | YDR536W | YEL033W |
| YDR403W | YDR458C | YDR498C | YDR537C | YEL034W |
| YDR404C | YDR459C | YDR499W | YDR538W | YEL035C |
| YDR405W | YDR460W | YDR500C | YDR539W | YEL036C |
| YDR408C | YDR461W | YDR501W | YDR540C | YEL037C |
| YDR410C | YDR462W | YDR502C | YDR541C | YEL038W |
| YDR411C | YDR463W | YDR503C | YDR542W | YEL039C |
| YDR412W | YDR465C | YDR504C | YDR543C | YEL040W |
| YDR413C | YDR467C | YDR506C | YDR544C | YEL041W |
| YDR414C | YDR468C | YDR508C | YEL001C | YEL042W |
| YDR415C | YDR469W | YDR509W | YEL002C | YEL044W |
| YDR417C | YDR470C | YDR510W | YEL003W | YEL045C |
| YDR418W | YDR471W | YDR511W | YEL004W | YEL046C |
| YDR423C | YDR472W | YDR512C | YEL005C | YEL047C |
| YDR425W | YDR473C | YDR513W | YEL008W | YEL048C |
| YDR427W | YDR474C | YDR514C | YEL009C | YEL049W |
| YDR428C | YDR475C | YDR515W | YEL010W | YEL050C |
| YDR429C | YDR476C | YDR516C | YEL011W | YEL051W |
| YDR431W | YDR477W | YDR517W | YEL012W | YEL052W |
| YDR435C | YDR478W | YDR518W | YEL013W | YEL053C |
| YDR437W | YDR479C | YDR519W | YEL014C | YEL054C |
| YDR438W | YDR480W | YDR520C | YEL015W | YEL055C |

FIG. 1G

| | | | | |
|---|---|---|---|---|
| YEL056W | YER019W | YER062C | YER113C | YER152C |
| YEL057C | YER020W | YER063W | YER115C | YER153C |
| YEL058W | YER021W | YER065C | YER116C | YER154W |
| YEL059C-A | YER022W | YER067W | YER117W | YER156C |
| YEL059W | YER023W | YER068W | YER118C | YER157W |
| YEL061C | YER025W | YER071C | YER119C | YER158C |
| YEL062W | YER026C | YER072W | YER119C-A | YER159C |
| YEL064C | YER027C | YER074W | YER120W | YER159C-A |
| YEL065W | YER028C | YER075C | YER121W | YER161C |
| YEL066W | YER029C | YER076C | YER122C | YER163C |
| YEL067C | YER030W | YER077C | YER123W | YER165W |
| YEL068C | YER031C | YER078C | YER124C | YER167W |
| YEL069C | YER034W | YER081W | YER125W | YER168C |
| YEL070W | YER036C | YER082C | YER126C | YER169W |
| YEL071W | YER037W | YER083C | YER127W | YER170W |
| YEL072W | YER038C | YER084W | YER128W | YER171W |
| YEL073C | YER039C | YER085C | YER130C | YER173W |
| YEL074W | YER039C-A | YER086W | YER131W | YER174C |
| YEL075C | YER040W | YER087C-A | YER133W | YER175C |
| YEL076C | YER042W | YER087W | YER134C | YER176W |
| YEL076C-A | YER043C | YER089C | YER135C | YER177W |
| YEL076W-C | YER044C | YER090W | YER136W | YER178W |
| YER001W | YER044C-A | YER091C | YER137C | YER179W |
| YER003C | YER046W | YER091C-A | YER137C-A | YER180C |
| YER004W | YER048C | YER092W | YER138W-A | YER181C |
| YER005W | YER048W-A | YER093C-A | YER139C | YER182W |
| YER006W | YER049W | YER094C | YER140W | YER183C |
| YER007C-A | YER050C | YER096W | YER141W | YER184C |
| YER007W | YER051W | YER097W | YER142C | YER185W |
| YER009W | YER052C | YER099C | YER143W | YER186C |
| YER010C | YER053C | YER100W | YER144C | YER187W |
| YER012W | YER055C | YER101C | YER145C | YER187W-A |
| YER014W | YER056C-A | YER102W | YER146W | YER188W |
| YER015W | YER058W | YER104W | YER147C | YER189W |
| YER016W | YER059W | YER106W | YER148W | YFL001W |
| YER018C | YER060W | YER107C | YER149C | YFL002C |
| YER019C-A | YER060W-A | YER112W | YER150W | YFL002W-B |

FIG. 1H

| | | | | |
|---|---|---|---|---|
| YFL003C | YFL042C | YFR012W | YFR049W | YGL032C |
| YFL004W | YFL043C | YFR013W | YFR050C | YGL033W |
| YFL005W | YFL044C | YFR014C | YFR051C | YGL035C |
| YFL006W | YFL045C | YFR015C | YFR052W | YGL036W |
| YFL009W | YFL046W | YFR017C | YFR053C | YGL037C |
| YFL010C | YFL047W | YFR018C | YFR054C | YGL038C |
| YFL010W-A | YFL048C | YFR020W | YFR055W | YGL039W |
| YFL011W | YFL049W | YFR021W | YFR056C | YGL040C |
| YFL012W | YFL050C | YFR022W | YFR057W | YGL041C |
| YFL013C | YFL051C | YFR023W | YGL001C | YGL042C |
| YFL013W-A | YFL052W | YFR024C | YGL002W | YGL043W |
| YFL014W | YFL053W | YFR025C | YGL003C | YGL044C |
| YFL015C | YFL054C | YFR026C | YGL004C | YGL045W |
| YFL016C | YFL055W | YFR027W | YGL005C | YGL046W |
| YFL017C | YFL056C | YFR028C | YGL006W | YGL047W |
| YFL017W-A | YFL057C | YFR029W | YGL007W | YGL048C |
| YFL018C | YFL058W | YFR030W | YGL008C | YGL050W |
| YFL019C | YFL059W | YFR031C | YGL009C | YGL051W |
| YFL020C | YFL060C | YFR031C-A | YGL010W | YGL052W |
| YFL021W | YFL061W | YFR032C | YGL011C | YGL053W |
| YFL022C | YFL062W | YFR032C-A | YGL012W | YGL054C |
| YFL023W | YFL063W | YFR033C | YGL015C | YGL055W |
| YFL025C | YFL064C | YFR034C | YGL016W | YGL056C |
| YFL026W | YFL065C | YFR035C | YGL017W | YGL057C |
| YFL027C | YFL066C | YFR036W | YGL018C | YGL058W |
| YFL028C | YFL067W | YFR037C | YGL019W | YGL059W |
| YFL029C | YFL068W | YFR038W | YGL020C | YGL060W |
| YFL030W | YFR001W | YFR039C | YGL021W | YGL061C |
| YFL031W | YFR002W | YFR040W | YGL023C | YGL062W |
| YFL032W | YFR003C | YFR041C | YGL024W | YGL063W |
| YFL034C-B | YFR005C | YFR042W | YGL025C | YGL064C |
| YFL034W | YFR006W | YFR043C | YGL026C | YGL065C |
| YFL036W | YFR007W | YFR044C | YGL027C | YGL066W |
| YFL038C | YFR008W | YFR045W | YGL028C | YGL067W |
| YFL039C | YFR009W | YFR046C | YGL029W | YGL068W |
| YFL040W | YFR010W | YFR047C | YGL030W | YGL069C |
| YFL041W | YFR011C | YFR048W | YGL031C | YGL070C |

FIG. 1I

| | | | | |
|---|---|---|---|---|
| YGL071W | YGL112C | YGL168W | YGL214W | YGL258W |
| YGL072C | YGL113W | YGL169W | YGL217C | YGL259W |
| YGL074C | YGL114W | YGL170C | YGL218W | YGL260W |
| YGL075C | YGL115W | YGL171W | YGL219C | YGL262W |
| YGL076C | YGL116W | YGL172W | YGL220W | YGL263W |
| YGL077C | YGL117W | YGL174W | YGL221C | YGR001C |
| YGL078C | YGL118C | YGL175C | YGL222C | YGR002C |
| YGL079W | YGL119W | YGL176C | YGL223C | YGR003W |
| YGL080W | YGL120C | YGL177W | YGL224C | YGR004W |
| YGL081W | YGL121C | YGL179C | YGL225W | YGR005C |
| YGL082W | YGL122C | YGL180W | YGL226C-A | YGR006W |
| YGL083W | YGL123W | YGL181W | YGL226W | YGR007W |
| YGL085W | YGL124C | YGL182C | YGL227W | YGR008C |
| YGL086W | YGL125W | YGL183C | YGL228W | YGR009C |
| YGL087C | YGL126W | YGL184C | YGL230C | YGR010W |
| YGL088W | YGL127C | YGL185C | YGL231C | YGR011W |
| YGL089C | YGL130W | YGL186C | YGL232W | YGR012W |
| YGL090W | YGL132W | YGL187C | YGL233W | YGR013W |
| YGL091C | YGL134W | YGL188C | YGL234W | YGR014W |
| YGL093W | YGL135W | YGL189C | YGL235W | YGR015C |
| YGL094C | YGL138C | YGL190C | YGL236C | YGR016W |
| YGL095C | YGL141W | YGL191W | YGL237C | YGR018C |
| YGL096W | YGL143C | YGL193C | YGL239C | YGR019W |
| YGL097W | YGL146C | YGL194C | YGL240W | YGR020C |
| YGL098W | YGL147C | YGL196W | YGL242C | YGR021W |
| YGL099W | YGL148W | YGL198W | YGL243W | YGR022C |
| YGL100W | YGL149W | YGL199C | YGL244W | YGR023W |
| YGL101W | YGL151W | YGL200C | YGL245W | YGR024C |
| YGL102C | YGL152C | YGL202W | YGL246C | YGR025W |
| YGL103W | YGL153W | YGL204C | YGL247W | YGR026W |
| YGL104C | YGL154C | YGL205W | YGL248W | YGR027C |
| YGL105W | YGL155W | YGL207W | YGL250W | YGR027W-A |
| YGL106W | YGL159W | YGL208W | YGL252C | YGR028W |
| YGL108C | YGL161C | YGL210W | YGL253W | YGR029W |
| YGL109W | YGL162W | YGL211W | YGL254W | YGR030C |
| YGL110C | YGL165C | YGL212W | YGL255W | YGR031W |
| YGL111W | YGL166W | YGL213C | YGL256W | YGR033C |

FIG. 1J

| | | | | |
|---|---|---|---|---|
| YGR034W | YGR070W | YGR113W | YGR150C | YGR187C |
| YGR035C | YGR072W | YGR114C | YGR151C | YGR188C |
| YGR036C | YGR073C | YGR116W | YGR152C | YGR190C |
| YGR037C | YGR074W | YGR117C | YGR153W | YGR191W |
| YGR038C-A | YGR075C | YGR118W | YGR154C | YGR192C |
| YGR038C-B | YGR076C | YGR119C | YGR155W | YGR193C |
| YGR038W | YGR077C | YGR120C | YGR156W | YGR194C |
| YGR039W | YGR078C | YGR121C | YGR157W | YGR195W |
| YGR040W | YGR079W | YGR122C-A | YGR158C | YGR196C |
| YGR041W | YGR081C | YGR122W | YGR159C | YGR197C |
| YGR042W | YGR082W | YGR123C | YGR160W | YGR198W |
| YGR043C | YGR083C | YGR124W | YGR161C | YGR200C |
| YGR044C | YGR084C | YGR125W | YGR161C-C | YGR201C |
| YGR045C | YGR086C | YGR126W | YGR161W-A | YGR202C |
| YGR046W | YGR087C | YGR127W | YGR162W | YGR203W |
| YGR047C | YGR088W | YGR128C | YGR163W | YGR204W |
| YGR048W | YGR091W | YGR129W | YGR164W | YGR205W |
| YGR049W | YGR092W | YGR130C | YGR165W | YGR206W |
| YGR050C | YGR093W | YGR131W | YGR166W | YGR207C |
| YGR051C | YGR094W | YGR132C | YGR167W | YGR208W |
| YGR053C | YGR095C | YGR133W | YGR168C | YGR209C |
| YGR054W | YGR096W | YGR134W | YGR169C | YGR210C |
| YGR055W | YGR097W | YGR135W | YGR170W | YGR211W |
| YGR056W | YGR099W | YGR136W | YGR171C | YGR212W |
| YGR057C | YGR100W | YGR137W | YGR172C | YGR213C |
| YGR058W | YGR101W | YGR138C | YGR173W | YGR214W |
| YGR059W | YGR102C | YGR139W | YGR174C | YGR215W |
| YGR060W | YGR103W | YGR140W | YGR175C | YGR216C |
| YGR061C | YGR104C | YGR141W | YGR176W | YGR218W |
| YGR062C | YGR106C | YGR142W | YGR177C | YGR219W |
| YGR063C | YGR107W | YGR143W | YGR178C | YGR220C |
| YGR064W | YGR108W | YGR144W | YGR179C | YGR221C |
| YGR065C | YGR109C | YGR145W | YGR180C | YGR222W |
| YGR066C | YGR109W-A | YGR146C | YGR181W | YGR223C |
| YGR067C | YGR110W | YGR147C | YGR182C | YGR224W |
| YGR068C | YGR111W | YGR148C | YGR183C | YGR226C |
| YGR069W | YGR112W | YGR149W | YGR185C | YGR227W |

FIG. 1K

| YGR228W | YGR267C | YHL015W | YHR005C | YHR049W |
| YGR229C | YGR268C | YHL016C | YHR005C-A | YHR050W |
| YGR230W | YGR269W | YHL017W | YHR006W | YHR051W |
| YGR231C | YGR270W | YHL018W | YHR010W | YHR052W |
| YGR232W | YGR272C | YHL019C | YHR011W | YHR053C |
| YGR233C | YGR273C | YHL020C | YHR012W | YHR054C |
| YGR234W | YGR274C | YHL021C | YHR013C | YHR055C |
| YGR235C | YGR275W | YHL022C | YHR014W | YHR056C |
| YGR236C | YGR277C | YHL023C | YHR015W | YHR057C |
| YGR237C | YGR278W | YHL024W | YHR016C | YHR058C |
| YGR238C | YGR279C | YHL025W | YHR017W | YHR059W |
| YGR239C | YGR280C | YHL026C | YHR018C | YHR060W |
| YGR241C | YGR282C | YHL027W | YHR019C | YHR061C |
| YGR242W | YGR283C | YHL028W | YHR020W | YHR062C |
| YGR243W | YGR284C | YHL029C | YHR021C | YHR063C |
| YGR244C | YGR285C | YHL031C | YHR021W-A | YHR065C |
| YGR246C | YGR286C | YHL032C | YHR022C | YHR066W |
| YGR247W | YGR287C | YHL033C | YHR025W | YHR067W |
| YGR248W | YGR288W | YHL034C | YHR026W | YHR068W |
| YGR249W | YGR290W | YHL036W | YHR029C | YHR070W |
| YGR250C | YGR291C | YHL037C | YHR030C | YHR071W |
| YGR251W | YGR293C | YHL038C | YHR031C | YHR072W |
| YGR252W | YGR294W | YHL039W | YHR032W | YHR072W-A |
| YGR253C | YGR295C | YHL040C | YHR033W | YHR074W |
| YGR254W | YHL001W | YHL041W | YHR034C | YHR076W |
| YGR255C | YHL002W | YHL042W | YHR036W | YHR077C |
| YGR256W | YHL004W | YHL043W | YHR037W | YHR078W |
| YGR257C | YHL005C | YHL044W | YHR038W | YHR079C-A |
| YGR258C | YHL006C | YHL045W | YHR040W | YHR081W |
| YGR259C | YHL007C | YHL046C | YHR041C | YHR083W |
| YGR260W | YHL009C | YHL047C | YHR043C | YHR084W |
| YGR261C | YHL009W-A | YHL048W | YHR044C | YHR085W |
| YGR262C | YHL010C | YHL049C | YHR045W | YHR086W |
| YGR263C | YHL011C | YHR001W | YHR046C | YHR087W |
| YGR264C | YHL012W | YHR001W-A | YHR047C | YHR088W |
| YGR265W | YHL013C | YHR002W | YHR048W | YHR090C |
| YGR266W | YHL014C | YHR003C | YHR049C-A | YHR091C |

FIG. 1L

| | | | | |
|---|---|---|---|---|
| YHR093W | YHR133C | YHR173C | YHR214W | YIL031W |
| YHR094C | YHR134W | YHR174W | YHR214W-A | YIL032C |
| YHR095W | YHR135C | YHR175W | YHR215W | YIL033C |
| YHR096C | YHR136C | YHR176W | YHR216W | YIL034C |
| YHR097C | YHR137W | YHR177W | YHR218W | YIL035C |
| YHR099W | YHR138C | YHR178W | YHR219W | YIL036W |
| YHR100C | YHR139C | YHR179W | YIL001W | YIL037C |
| YHR101C | YHR139C-A | YHR180W | YIL002C | YIL038C |
| YHR103W | YHR140W | YHR181W | YIL003W | YIL039W |
| YHR104W | YHR141C | YHR183W | YIL004C | YIL040W |
| YHR105W | YHR142W | YHR184W | YIL005W | YIL041W |
| YHR106W | YHR143W | YHR185C | YIL006W | YIL042C |
| YHR107C | YHR143W-A | YHR188C | YIL007C | YIL043C |
| YHR108W | YHR144C | YHR189W | YIL008W | YIL044C |
| YHR109W | YHR145C | YHR190W | YIL009C-A | YIL045W |
| YHR110W | YHR147C | YHR191C | YIL009W | YIL046W |
| YHR111W | YHR148W | YHR192W | YIL010W | YIL047C |
| YHR112C | YHR149C | YHR193C | YIL011W | YIL048W |
| YHR113W | YHR150W | YHR195W | YIL012W | YIL049W |
| YHR114W | YHR151C | YHR196W | YIL014W | YIL050W |
| YHR115C | YHR152W | YHR197W | YIL015C-A | YIL051C |
| YHR116W | YHR153C | YHR198C | YIL015W | YIL052C |
| YHR117W | YHR154W | YHR199C | YIL016W | YIL053W |
| YHR118C | YHR155W | YHR200W | YIL017C | YIL054W |
| YHR119W | YHR157W | YHR202W | YIL018W | YIL055C |
| YHR120W | YHR158C | YHR203C | YIL019W | YIL056W |
| YHR121W | YHR159W | YHR204W | YIL020C | YIL057C |
| YHR122W | YHR160C | YHR205W | YIL021W | YIL058W |
| YHR123W | YHR162W | YHR206W | YIL022W | YIL059C |
| YHR124W | YHR163W | YHR207C | YIL023C | YIL060W |
| YHR125W | YHR165C | YHR208W | YIL024C | YIL061C |
| YHR126C | YHR166C | YHR209W | YIL025C | YIL062C |
| YHR127W | YHR168W | YHR210C | YIL026C | YIL063C |
| YHR129C | YHR169W | YHR211W | YIL027C | YIL064W |
| YHR130C | YHR170W | YHR212C | YIL028W | YIL065C |
| YHR131C | YHR171W | YHR213W | YIL029C | YIL066C |
| YHR132C | YHR172W | YHR214C-C | YIL030C | YIL067C |

FIG. 1M

| | | | | |
|---|---|---|---|---|
| YIL069C | YIL108W | YIL156W | YIR020C | YJL018W |
| YIL070C | YIL109C | YIL157C | YIR020W-B | YJL019W |
| YIL071C | YIL110W | YIL158W | YIR021W | YJL020C |
| YIL072W | YIL111W | YIL159W | YIR022W | YJL021C |
| YIL073C | YIL112W | YIL160C | YIR023W | YJL022W |
| YIL074C | YIL113W | YIL162W | YIR024C | YJL023C |
| YIL075C | YIL114C | YIL163C | YIR025W | YJL024C |
| YIL076W | YIL116W | YIL164C | YIR026C | YJL025W |
| YIL077C | YIL120W | YIL165C | YIR027C | YJL026W |
| YIL078W | YIL121W | YIL166C | YIR028W | YJL027C |
| YIL079C | YIL122W | YIL167W | YIR029W | YJL028W |
| YIL080W | YIL123W | YIL168W | YIR030C | YJL029C |
| YIL082W | YIL124W | YIL169C | YIR031C | YJL030W |
| YIL083C | YIL125W | YIL170W | YIR034C | YJL031C |
| YIL084C | YIL127C | YIL171W | YIR035C | YJL032W |
| YIL085C | YIL128W | YIL172C | YIR036C | YJL033W |
| YIL086C | YIL131C | YIL173W | YIR037W | YJL034W |
| YIL087C | YIL132C | YIL174W | YIR038C | YJL035C |
| YIL088C | YIL133C | YIL175W | YIR039C | YJL036W |
| YIL089W | YIL134W | YIL176C | YIR040C | YJL037W |
| YIL090W | YIL136W | YIR001C | YIR041W | YJL038C |
| YIL091C | YIL138C | YIR002C | YIR042C | YJL041W |
| YIL092W | YIL139C | YIR003W | YIR043C | YJL043W |
| YIL093C | YIL140W | YIR004W | YIR044C | YJL044C |
| YIL094C | YIL142W | YIR005W | YJL001W | YJL045W |
| YIL095W | YIL143C | YIR007W | YJL002C | YJL046W |
| YIL096C | YIL144W | YIR008C | YJL003W | YJL047C |
| YIL097W | YIL145C | YIR009W | YJL004C | YJL048C |
| YIL098C | YIL146C | YIR010W | YJL006C | YJL049W |
| YIL099W | YIL147C | YIR011C | YJL007C | YJL050W |
| YIL100W | YIL148W | YIR012W | YJL009W | YJL051W |
| YIL102C | YIL150C | YIR013C | YJL011C | YJL052W |
| YIL103W | YIL151C | YIR014W | YJL012C | YJL053W |
| YIL104C | YIL152W | YIR015W | YJL013C | YJL054W |
| YIL105C | YIL153W | YIR016W | YJL015C | YJL055W |
| YIL106W | YIL154C | YIR017C | YJL016W | YJL056C |
| YIL107C | YIL155C | YIR018W | YJL017W | YJL057C |

FIG. 1N

| | | | | |
|---|---|---|---|---|
| YJL058C | YJL098W | YJL142C | YJL181W | YJL222W |
| YJL059W | YJL099W | YJL143W | YJL182C | YJL223C |
| YJL060W | YJL100W | YJL144W | YJL183W | YJR001W |
| YJL061W | YJL101C | YJL145W | YJL184W | YJR002W |
| YJL062W | YJL102W | YJL147C | YJL185C | YJR003C |
| YJL063C | YJL103C | YJL148W | YJL186W | YJR004C |
| YJL064W | YJL104W | YJL149W | YJL187C | YJR005W |
| YJL065C | YJL105W | YJL150W | YJL188C | YJR006W |
| YJL066C | YJL106W | YJL151C | YJL189W | YJR007W |
| YJL067W | YJL107C | YJL152W | YJL190C | YJR008W |
| YJL068C | YJL108C | YJL153C | YJL191W | YJR009C |
| YJL069C | YJL110C | YJL154C | YJL192C | YJR010C-A |
| YJL070C | YJL111W | YJL155C | YJL193W | YJR011C |
| YJL071W | YJL112W | YJL156C | YJL194W | YJR012C |
| YJL072C | YJL115W | YJL157C | YJL195C | YJR013W |
| YJL073W | YJL116C | YJL158C | YJL197W | YJR014W |
| YJL074C | YJL117W | YJL160C | YJL199C | YJR015W |
| YJL075C | YJL118W | YJL161W | YJL200C | YJR016C |
| YJL077C | YJL119C | YJL162C | YJL201W | YJR017C |
| YJL078C | YJL120W | YJL163C | YJL202C | YJR018W |
| YJL079C | YJL121C | YJL164C | YJL203W | YJR019C |
| YJL080C | YJL122W | YJL165C | YJL204C | YJR020W |
| YJL081C | YJL123C | YJL166W | YJL206C | YJR021C |
| YJL082W | YJL124C | YJL167W | YJL208C | YJR022W |
| YJL083W | YJL125C | YJL168C | YJL209W | YJR024C |
| YJL084C | YJL126W | YJL169W | YJL210W | YJR025C |
| YJL085W | YJL127C | YJL170C | YJL211C | YJR026W |
| YJL086C | YJL128C | YJL171C | YJL212C | YJR028W |
| YJL087C | YJL129C | YJL172W | YJL213W | YJR032W |
| YJL088W | YJL131C | YJL173C | YJL214W | YJR033C |
| YJL089W | YJL133W | YJL174W | YJL215C | YJR034W |
| YJL090C | YJL134W | YJL175W | YJL216C | YJR036C |
| YJL091C | YJL135W | YJL176C | YJL217W | YJR037W |
| YJL093C | YJL137C | YJL177W | YJL218W | YJR038C |
| YJL094C | YJL138C | YJL178C | YJL219W | YJR043C |
| YJL096W | YJL139C | YJL179W | YJL220W | YJR044C |
| YJL097W | YJL140W | YJL180C | YJL221C | YJR046W |

FIG. 10

| | | | | |
|---|---|---|---|---|
| YJR047C | YJR087W | YJR127C | YKL009W | YKL053C-A |
| YJR048W | YJR088C | YJR128W | YKL010C | YKL053W |
| YJR049C | YJR089W | YJR129C | YKL011C | YKL055C |
| YJR050W | YJR091C | YJR131W | YKL012W | YKL056C |
| YJR051W | YJR093C | YJR132W | YKL013C | YKL057C |
| YJR052W | YJR094W-A | YJR133W | YKL015W | YKL058W |
| YJR053W | YJR095W | YJR134C | YKL016C | YKL059C |
| YJR054W | YJR096W | YJR135C | YKL017C | YKL060C |
| YJR055W | YJR097W | YJR135W-A | YKL018W | YKL061W |
| YJR056C | YJR098C | YJR136C | YKL019W | YKL062W |
| YJR057W | YJR099W | YJR139C | YKL021C | YKL063C |
| YJR058C | YJR100C | YJR141W | YKL023W | YKL065C |
| YJR059W | YJR101W | YJR142W | YKL024C | YKL066W |
| YJR060W | YJR102C | YJR144W | YKL025C | YKL067W |
| YJR062C | YJR103W | YJR145C | YKL026C | YKL069W |
| YJR063W | YJR104C | YJR146W | YKL027W | YKL070W |
| YJR064W | YJR105W | YJR147W | YKL028W | YKL071W |
| YJR065C | YJR106W | YJR148W | YKL029C | YKL072W |
| YJR067C | YJR107W | YJR149W | YKL031W | YKL073W |
| YJR068W | YJR108W | YJR150C | YKL033W | YKL074C |
| YJR069C | YJR109C | YJR152W | YKL033W-A | YKL075C |
| YJR070C | YJR110W | YJR153W | YKL034W | YKL076C |
| YJR071W | YJR111C | YJR154W | YKL035W | YKL077W |
| YJR072C | YJR112W | YJR155W | YKL036C | YKL078W |
| YJR073C | YJR113C | YJR156C | YKL037W | YKL079W |
| YJR074W | YJR114W | YJR157W | YKL039W | YKL080W |
| YJR075W | YJR115W | YJR159W | YKL040C | YKL081W |
| YJR076C | YJR116W | YJR162C | YKL041W | YKL082C |
| YJR077C | YJR117W | YKL001C | YKL043W | YKL084W |
| YJR078W | YJR118C | YKL002W | YKL044W | YKL085W |
| YJR079W | YJR119C | YKL003C | YKL045W | YKL086W |
| YJR080C | YJR120W | YKL004W | YKL046C | YKL087C |
| YJR082C | YJR121W | YKL005C | YKL047W | YKL088W |
| YJR083C | YJR122W | YKL006C-A | YKL048C | YKL090W |
| YJR084W | YJR124C | YKL006W | YKL049C | YKL091C |
| YJR085C | YJR125C | YKL007W | YKL051W | YKL092C |
| YJR086W | YJR126C | YKL008C | YKL052C | YKL093W |

FIG. 1P

| | | | | |
|---|---|---|---|---|
| YKL094W | YKL137W | YKL176C | YKL220C | YKR035W-A |
| YKL095W | YKL138C | YKL177W | YKL221W | YKR036C |
| YKL096W | YKL139W | YKL178C | YKL222C | YKR037C |
| YKL096W-A | YKL140W | YKL179C | YKL223W | YKR038C |
| YKL097C | YKL141W | YKL180W | YKL224C | YKR039W |
| YKL098W | YKL143W | YKL181W | YKR001C | YKR041W |
| YKL099C | YKL144C | YKL183W | YKR002W | YKR042W |
| YKL100C | YKL145W | YKL184W | YKR003W | YKR043C |
| YKL102C | YKL146W | YKL185W | YKR004C | YKR044W |
| YKL103C | YKL147C | YKL186C | YKR005C | YKR045C |
| YKL104C | YKL148C | YKL187C | YKR006C | YKR046C |
| YKL105C | YKL149C | YKL188C | YKR007W | YKR047W |
| YKL106W | YKL150W | YKL189W | YKR008W | YKR048C |
| YKL107W | YKL151C | YKL190W | YKR009C | YKR049C |
| YKL109W | YKL153W | YKL191W | YKR010C | YKR050W |
| YKL110C | YKL154W | YKL192C | YKR011C | YKR051W |
| YKL111C | YKL155C | YKL193C | YKR012C | YKR052C |
| YKL112W | YKL156W | YKL194C | YKR013W | YKR053C |
| YKL113C | YKL157W | YKL195W | YKR014C | YKR055W |
| YKL114C | YKL158W | YKL196C | YKR015C | YKR056W |
| YKL115C | YKL159C | YKL197C | YKR016W | YKR058W |
| YKL116C | YKL160W | YKL202W | YKR017C | YKR059W |
| YKL117W | YKL161C | YKL204W | YKR018C | YKR060W |
| YKL118W | YKL162C | YKL205W | YKR020W | YKR061W |
| YKL119C | YKL162C-A | YKL206C | YKR021W | YKR062W |
| YKL120W | YKL163W | YKL207W | YKR022C | YKR063C |
| YKL122C | YKL164C | YKL208W | YKR024C | YKR064W |
| YKL123W | YKL165C | YKL209C | YKR025W | YKR065C |
| YKL124W | YKL166C | YKL210W | YKR026C | YKR066C |
| YKL125W | YKL167C | YKL211C | YKR028W | YKR067W |
| YKL127W | YKL168C | YKL212W | YKR029C | YKR068C |
| YKL128C | YKL169C | YKL213C | YKR030W | YKR069W |
| YKL130C | YKL170W | YKL214C | YKR031C | YKR070W |
| YKL131W | YKL171W | YKL216W | YKR032W | YKR071C |
| YKL132C | YKL172W | YKL217W | YKR033C | YKR072C |
| YKL133C | YKL174C | YKL218C | YKR034W | YKR073C |
| YKL134C | YKL175W | YKL219W | YKR035C | YKR074W |

FIG. 1Q

| | | | | |
|---|---|---|---|---|
| YKR075C | YLL010C | YLL050C | YLR021W | YLR059C |
| YKR076W | YLL011W | YLL051C | YLR022C | YLR060W |
| YKR077W | YLL012W | YLL052C | YLR023C | YLR061W |
| YKR078W | YLL013C | YLL053C | YLR024C | YLR062C |
| YKR079C | YLL014W | YLL054C | YLR025W | YLR063W |
| YKR080W | YLL016W | YLL055W | YLR026C | YLR064W |
| YKR081C | YLL017W | YLL056C | YLR027C | YLR065C |
| YKR082W | YLL018C | YLL057C | YLR028C | YLR066W |
| YKR083C | YLL018C-A | YLL058W | YLR029C | YLR067C |
| YKR084C | YLL019C | YLL059C | YLR030W | YLR068W |
| YKR085C | YLL020C | YLL060C | YLR031W | YLR069C |
| YKR086W | YLL021W | YLL061W | YLR033W | YLR070C |
| YKR087C | YLL022C | YLL062C | YLR034C | YLR071C |
| YKR088C | YLL023C | YLL064C | YLR035C | YLR072W |
| YKR089C | YLL024C | YLL065W | YLR035C-A | YLR073C |
| YKR090W | YLL025W | YLL066C | YLR036C | YLR074C |
| YKR091W | YLL026W | YLL067C | YLR037C | YLR075W |
| YKR092C | YLL027W | YLR001C | YLR038C | YLR076C |
| YKR093W | YLL028W | YLR002C | YLR040C | YLR077W |
| YKR094C | YLL029W | YLR003C | YLR041W | YLR078C |
| YKR096W | YLL030C | YLR004C | YLR042C | YLR079W |
| YKR097W | YLL031C | YLR005W | YLR043C | YLR080W |
| YKR098C | YLL032C | YLR006C | YLR044C | YLR081W |
| YKR099W | YLL033W | YLR007W | YLR045C | YLR082C |
| YKR100C | YLL034C | YLR008C | YLR046C | YLR083C |
| YKR101W | YLL035W | YLR009W | YLR047C | YLR085C |
| YKR104W | YLL036C | YLR010C | YLR048W | YLR088W |
| YKR105C | YLL037W | YLR011W | YLR049C | YLR089C |
| YKR106W | YLL038C | YLR012C | YLR050C | YLR090W |
| YLL001W | YLL041C | YLR013W | YLR051C | YLR091W |
| YLL002W | YLL042C | YLR014C | YLR052W | YLR093C |
| YLL003W | YLL043W | YLR015W | YLR053C | YLR094C |
| YLL004W | YLL044W | YLR016C | YLR054C | YLR095C |
| YLL005C | YLL045C | YLR017W | YLR055C | YLR097C |
| YLL006W | YLL046C | YLR018C | YLR056W | YLR098C |
| YLL007C | YLL047W | YLR019W | YLR057W | YLR099C |
| YLL009C | YLL049W | YLR020C | YLR058C | YLR100W |

FIG. 1R

| | | | | |
|---|---|---|---|---|
| YLR101C | YLR144C | YLR181C | YLR224W | YLR266C |
| YLR102C | YLR145W | YLR182W | YLR225C | YLR267W |
| YLR103C | YLR146C | YLR183C | YLR226W | YLR268W |
| YLR104W | YLR147C | YLR184W | YLR227C | YLR269C |
| YLR105C | YLR148W | YLR185W | YLR227W-A | YLR270W |
| YLR107W | YLR149C | YLR186W | YLR228C | YLR271W |
| YLR108C | YLR150W | YLR187W | YLR230W | YLR273C |
| YLR109W | YLR151C | YLR188W | YLR231C | YLR274W |
| YLR110C | YLR152C | YLR190W | YLR232W | YLR275W |
| YLR111W | YLR153C | YLR191W | YLR233C | YLR276C |
| YLR112W | YLR154C | YLR192C | YLR235C | YLR277C |
| YLR113W | YLR155C | YLR193C | YLR236C | YLR279W |
| YLR116W | YLR156W | YLR194C | YLR237W | YLR280C |
| YLR118C | YLR157C | YLR195C | YLR238W | YLR281C |
| YLR119W | YLR157C-A | YLR196W | YLR239C | YLR282C |
| YLR120C | YLR158C | YLR197W | YLR240W | YLR283W |
| YLR121C | YLR159W | YLR198C | YLR241W | YLR284C |
| YLR122C | YLR160C | YLR199C | YLR242C | YLR285W |
| YLR123C | YLR161W | YLR201C | YLR243W | YLR286C |
| YLR124W | YLR162W | YLR203C | YLR244C | YLR287C |
| YLR125W | YLR163C | YLR204W | YLR245C | YLR287C-A |
| YLR126C | YLR164W | YLR205C | YLR246W | YLR288C |
| YLR127C | YLR165C | YLR207W | YLR248W | YLR289W |
| YLR128W | YLR166C | YLR208W | YLR250W | YLR290C |
| YLR130C | YLR167W | YLR209C | YLR251W | YLR291C |
| YLR132C | YLR168C | YLR210W | YLR252W | YLR292C |
| YLR133W | YLR170C | YLR212C | YLR253W | YLR293C |
| YLR134W | YLR171W | YLR213C | YLR254C | YLR294C |
| YLR135W | YLR172C | YLR214W | YLR255C | YLR295C |
| YLR136C | YLR173W | YLR215C | YLR256W-A | YLR296W |
| YLR137W | YLR174W | YLR216C | YLR257W | YLR297W |
| YLR138W | YLR175W | YLR217W | YLR258W | YLR298C |
| YLR139C | YLR176C | YLR218C | YLR261C | YLR299W |
| YLR140W | YLR177W | YLR219W | YLR262C | YLR300W |
| YLR141W | YLR178C | YLR220W | YLR263W | YLR301W |
| YLR142W | YLR179C | YLR221C | YLR264W | YLR302C |
| YLR143W | YLR180W | YLR222C | YLR265C | YLR303W |

FIG. 1S

| | | | | |
|---|---|---|---|---|
| YLR304C | YLR345W | YLR387C | YLR428C | YML008C |
| YLR306W | YLR346C | YLR388W | YLR429W | YML009C |
| YLR307W | YLR347C | YLR389C | YLR431C | YML010C-B |
| YLR308W | YLR348C | YLR390W | YLR432W | YML010W-A |
| YLR309C | YLR349W | YLR390W-A | YLR434C | YML011C |
| YLR310C | YLR350W | YLR392C | YLR435W | YML012W |
| YLR311C | YLR351C | YLR393W | YLR437C | YML013C-A |
| YLR312C | YLR352W | YLR394W | YLR438C-A | YML013W |
| YLR312W-A | YLR353W | YLR395C | YLR438W | YML014W |
| YLR313C | YLR354C | YLR396C | YLR439W | YML015C |
| YLR314C | YLR355C | YLR397C | YLR440C | YML018C |
| YLR315W | YLR356W | YLR398C | YLR441C | YML019W |
| YLR316C | YLR357W | YLR399C | YLR443W | YML020W |
| YLR317W | YLR358C | YLR400W | YLR444C | YML021C |
| YLR319C | YLR359W | YLR401C | YLR445W | YML022W |
| YLR321C | YLR360W | YLR402W | YLR446W | YML023C |
| YLR322W | YLR361C | YLR404W | YLR447C | YML024W |
| YLR323C | YLR362W | YLR405W | YLR448W | YML025C |
| YLR324W | YLR363C | YLR406C | YLR449W | YML026C |
| YLR325C | YLR364W | YLR407W | YLR451W | YML027W |
| YLR326W | YLR365W | YLR408C | YLR452C | YML028W |
| YLR327C | YLR366W | YLR409C | YLR453C | YML029W |
| YLR328W | YLR367W | YLR410W-A | YLR455W | YML030W |
| YLR329W | YLR369W | YLR411W | YLR456W | YML031W |
| YLR330W | YLR370C | YLR412W | YLR457C | YML032C |
| YLR331C | YLR372W | YLR413W | YLR458W | YML035C |
| YLR332W | YLR373C | YLR414C | YLR459W | YML035C-A |
| YLR333C | YLR374C | YLR415C | YLR460C | YML036W |
| YLR334C | YLR375W | YLR416C | YLR461W | YML037C |
| YLR335W | YLR376C | YLR417W | YLR462W | YML038C |
| YLR336C | YLR377C | YLR418C | YLR463C | YML040W |
| YLR338W | YLR378C | YLR420W | YLR465C | YML041C |
| YLR339C | YLR379W | YLR421C | YML001W | YML042W |
| YLR340W | YLR382C | YLR424W | YML004C | YML043C |
| YLR341W | YLR383W | YLR425W | YML005W | YML045W |
| YLR343W | YLR385C | YLR426W | YML006C | YML045W-A |
| YLR344W | YLR386W | YLR427W | YML007W | YML046W |

FIG. 1T

| | | | | |
|---|---|---|---|---|
| YML047C | YML087C | YML124C | YMR033W | YMR072W |
| YML048W | YML088W | YML125C | YMR034C | YMR073C |
| YML048W-A | YML089C | YML126C | YMR035W | YMR074C |
| YML050W | YML090W | YML127W | YMR036C | YMR075C-A |
| YML051W | YML091C | YML128C | YMR037C | YMR075W |
| YML052W | YML092C | YML129C | YMR038C | YMR076C |
| YML053C | YML094W | YML130C | YMR039C | YMR077C |
| YML054C | YML095C | YML131W | YMR040W | YMR079W |
| YML055W | YML095C-A | YML132W | YMR041C | YMR081C |
| YML056C | YML096W | YMR001C | YMR042W | YMR082C |
| YML058C-A | YML097C | YMR002W | YMR043W | YMR083W |
| YML058W | YML098W | YMR003W | YMR044W | YMR084W |
| YML058W-A | YML099C | YMR004W | YMR046C | YMR085W |
| YML059C | YML100W | YMR005W | YMR046W-A | YMR086C-A |
| YML060W | YML100W-A | YMR008C | YMR048W | YMR086W |
| YML063W | YML101C | YMR009W | YMR049C | YMR087W |
| YML064C | YML102C-A | YMR010W | YMR051C | YMR088C |
| YML065W | YML102W | YMR011W | YMR052C-A | YMR090W |
| YML066C | YML104C | YMR013C | YMR052W | YMR091C |
| YML067C | YML105C | YMR014W | YMR053C | YMR092C |
| YML068W | YML106W | YMR015C | YMR054W | YMR093W |
| YML069W | YML107C | YMR016C | YMR055C | YMR094W |
| YML070W | YML108W | YMR017W | YMR056C | YMR095C |
| YML071C | YML109W | YMR018W | YMR058W | YMR096W |
| YML073C | YML110C | YMR020W | YMR059W | YMR097C |
| YML074C | YML112W | YMR021C | YMR060C | YMR098C |
| YML075C | YML113W | YMR022W | YMR061W | YMR099C |
| YML077W | YML114C | YMR023C | YMR062C | YMR100W |
| YML078W | YML115C | YMR024W | YMR063W | YMR101C |
| YML079W | YML116W | YMR025W | YMR064W | YMR102C |
| YML080W | YML117W-A | YMR026C | YMR065W | YMR103C |
| YML081C-A | YML118W | YMR027W | YMR066W | YMR104C |
| YML082W | YML119W | YMR028W | YMR067C | YMR105C |
| YML083C | YML120C | YMR029C | YMR068W | YMR106C |
| YML084W | YML121W | YMR030W | YMR069W | YMR107W |
| YML085C | YML122C | YMR031C | YMR070W | YMR108W |
| YML086C | YML123C | YMR031W-A | YMR071C | YMR110C |

FIG. 1U

| | | | | |
|---|---|---|---|---|
| YMR111C | YMR151W | YMR189W | YMR232W | YMR274C |
| YMR112C | YMR152W | YMR191W | YMR233W | YMR276W |
| YMR113W | YMR153C-A | YMR192W | YMR234W | YMR277W |
| YMR115W | YMR153W | YMR193C-A | YMR235C | YMR278W |
| YMR116C | YMR154C | YMR193W | YMR236W | YMR279C |
| YMR117C | YMR155W | YMR194C-A | YMR237W | YMR280C |
| YMR118C | YMR156C | YMR194W | YMR238W | YMR281W |
| YMR119W | YMR157C | YMR195W | YMR239C | YMR282C |
| YMR119W-A | YMR158C-B | YMR197C | YMR240C | YMR283C |
| YMR120C | YMR158W | YMR198W | YMR241W | YMR284W |
| YMR121C | YMR158W-A | YMR199W | YMR242C | YMR285C |
| YMR122C | YMR159C | YMR200W | YMR243C | YMR286W |
| YMR123W | YMR160W | YMR201C | YMR244C-A | YMR287C |
| YMR124W | YMR163C | YMR202W | YMR244W | YMR289W |
| YMR125W | YMR166C | YMR204C | YMR245W | YMR290C |
| YMR126C | YMR167W | YMR206W | YMR246W | YMR290W-A |
| YMR127C | YMR168C | YMR208W | YMR250W | YMR291W |
| YMR129W | YMR169C | YMR209C | YMR251W | YMR292W |
| YMR130W | YMR170C | YMR210W | YMR251W-A | YMR293C |
| YMR131C | YMR171C | YMR211W | YMR252C | YMR294W |
| YMR132C | YMR172C-A | YMR212C | YMR253C | YMR294W-A |
| YMR134W | YMR173W | YMR213W | YMR254C | YMR295C |
| YMR135C | YMR173W-A | YMR214W | YMR255W | YMR296C |
| YMR135W-A | YMR174C | YMR215W | YMR256C | YMR297W |
| YMR137C | YMR175W | YMR216C | YMR257C | YMR298W |
| YMR138W | YMR177W | YMR217W | YMR258C | YMR299C |
| YMR139W | YMR178W | YMR218C | YMR260C | YMR300C |
| YMR140W | YMR179W | YMR220W | YMR262W | YMR301C |
| YMR141C | YMR180C | YMR221C | YMR263W | YMR302C |
| YMR143W | YMR181C | YMR222C | YMR264W | YMR303C |
| YMR144W | YMR182C | YMR223W | YMR267W | YMR304C-A |
| YMR145C | YMR183C | YMR224C | YMR268C | YMR304W |
| YMR146C | YMR184W | YMR225C | YMR269W | YMR305C |
| YMR147W | YMR185W | YMR226C | YMR270C | YMR306C-A |
| YMR148W | YMR186W | YMR227C | YMR271C | YMR307W |
| YMR149W | YMR187C | YMR228W | YMR272C | YMR308C |
| YMR150C | YMR188C | YMR231W | YMR273C | YMR309C |

FIG. 1V

| | | | | |
|---|---|---|---|---|
| YMR310C | YNL023C | YNL062C | YNL104C | YNL148C |
| YMR311C | YNL024C | YNL063W | YNL105W | YNL149C |
| YMR312W | YNL025C | YNL064C | YNL107W | YNL150W |
| YMR313C | YNL026W | YNL065W | YNL108C | YNL151C |
| YMR314W | YNL027W | YNL066W | YNL109W | YNL152W |
| YMR315W | YNL028W | YNL067W | YNL110C | YNL153C |
| YMR316C-A | YNL029C | YNL068C | YNL111C | YNL154C |
| YMR316C-B | YNL030W | YNL069C | YNL113W | YNL155W |
| YMR316W | YNL031C | YNL070W | YNL114C | YNL156C |
| YMR318C | YNL032W | YNL072W | YNL117W | YNL157W |
| YMR319C | YNL033W | YNL073W | YNL118C | YNL158W |
| YMR320W | YNL034W | YNL074C | YNL119W | YNL159C |
| YMR321C | YNL035C | YNL075W | YNL120C | YNL160W |
| YMR322C | YNL036W | YNL076W | YNL121C | YNL161W |
| YMR323W | YNL037C | YNL077W | YNL122C | YNL162W |
| YMR324C | YNL038W | YNL078W | YNL123W | YNL164C |
| YMR325W | YNL039W | YNL079C | YNL124W | YNL165W |
| YMR326C | YNL040W | YNL080C | YNL125C | YNL166C |
| YNL001W | YNL041C | YNL081C | YNL126W | YNL167C |
| YNL003C | YNL042W | YNL082W | YNL127W | YNL168C |
| YNL004W | YNL043C | YNL084C | YNL128W | YNL169C |
| YNL005C | YNL044W | YNL085W | YNL129W | YNL170W |
| YNL007C | YNL045W | YNL086W | YNL130C | YNL171C |
| YNL008C | YNL046W | YNL087W | YNL131W | YNL172W |
| YNL009W | YNL048W | YNL089C | YNL133C | YNL173C |
| YNL010W | YNL049C | YNL090W | YNL134C | YNL174W |
| YNL011C | YNL050C | YNL092W | YNL135C | YNL175C |
| YNL012W | YNL051W | YNL093W | YNL136W | YNL176C |
| YNL013C | YNL052W | YNL094W | YNL137C | YNL177C |
| YNL014W | YNL053W | YNL095C | YNL138W | YNL178W |
| YNL015W | YNL054W-A | YNL096C | YNL140C | YNL179C |
| YNL017C | YNL055C | YNL097C | YNL141W | YNL180C |
| YNL018C | YNL056W | YNL099C | YNL142W | YNL181W |
| YNL019C | YNL057W | YNL100W | YNL143C | YNL182C |
| YNL020C | YNL058C | YNL101W | YNL144C | YNL183C |
| YNL021W | YNL059C | YNL102W | YNL145W | YNL184C |
| YNL022C | YNL061W | YNL103W | YNL147W | YNL185C |

FIG. 1W

| | | | | |
|---|---|---|---|---|
| YNL186W | YNL230C | YNL276C | YNL315C | YNR020C |
| YNL187W | YNL231C | YNL277W | YNL316C | YNR021W |
| YNL188W | YNL232W | YNL278W | YNL317W | YNR022C |
| YNL189W | YNL233W | YNL279W | YNL319W | YNR023W |
| YNL190W | YNL234W | YNL280C | YNL320W | YNR024W |
| YNL191W | YNL235C | YNL281W | YNL321W | YNR025C |
| YNL193W | YNL236W | YNL282W | YNL322C | YNR026C |
| YNL194C | YNL237W | YNL283C | YNL323W | YNR027W |
| YNL195C | YNL238W | YNL284C | YNL324W | YNR028W |
| YNL196C | YNL239W | YNL284C-A | YNL325C | YNR029C |
| YNL198C | YNL240C | YNL285W | YNL326C | YNR030W |
| YNL199C | YNL241C | YNL286W | YNL327W | YNR032C-A |
| YNL200C | YNL243W | YNL287W | YNL328C | YNR032W |
| YNL202W | YNL244C | YNL288W | YNL329C | YNR033W |
| YNL203C | YNL245C | YNL289W | YNL330C | YNR034W |
| YNL204C | YNL246W | YNL290W | YNL331C | YNR035C |
| YNL206C | YNL248C | YNL291C | YNL332W | YNR036C |
| YNL207W | YNL249C | YNL292W | YNL333W | YNR038W |
| YNL208W | YNL252C | YNL293W | YNL334C | YNR039C |
| YNL209W | YNL253W | YNL294C | YNL335W | YNR041C |
| YNL210W | YNL254C | YNL295W | YNL336W | YNR042W |
| YNL211C | YNL255C | YNL296W | YNL337W | YNR045W |
| YNL212W | YNL256W | YNL299W | YNL338W | YNR046W |
| YNL213C | YNL257C | YNL300W | YNR001C | YNR047W |
| YNL214W | YNL258C | YNL301C | YNR002C | YNR048W |
| YNL217W | YNL259C | YNL303W | YNR003C | YNR049C |
| YNL218W | YNL260C | YNL304W | YNR005C | YNR050C |
| YNL219C | YNL261W | YNL305C | YNR006W | YNR051C |
| YNL220W | YNL263C | YNL306W | YNR007C | YNR052C |
| YNL221C | YNL264C | YNL307C | YNR008W | YNR054C |
| YNL222W | YNL265C | YNL308C | YNR009W | YNR055C |
| YNL223W | YNL266W | YNL309W | YNR010W | YNR056C |
| YNL224C | YNL268W | YNL310C | YNR014W | YNR057C |
| YNL225C | YNL269W | YNL311C | YNR015W | YNR058W |
| YNL226W | YNL270C | YNL312W | YNR017W | YNR059W |
| YNL228W | YNL274C | YNL313C | YNR018W | YNR060W |
| YNL229C | YNL275W | YNL314W | YNR019W | YNR061C |

FIG. 1X

| | | | | |
|---|---|---|---|---|
| YNR062C | YOL026C | YOL065C | YOL103W | YOL144W |
| YNR063W | YOL027C | YOL066C | YOL103W-A | YOL146W |
| YNR066C | YOL028C | YOL067C | YOL105C | YOL147C |
| YNR067C | YOL029C | YOL068C | YOL106W | YOL148C |
| YNR068C | YOL030W | YOL069W | YOL107W | YOL149W |
| YNR069C | YOL031C | YOL070C | YOL108C | YOL150C |
| YNR071C | YOL032W | YOL071W | YOL109W | YOL151W |
| YNR072W | YOL033W | YOL072W | YOL110W | YOL152W |
| YNR073C | YOL034W | YOL073C | YOL111C | YOL153C |
| YNR074C | YOL035C | YOL075C | YOL112W | YOL154W |
| YNR075W | YOL036W | YOL076W | YOL114C | YOL155C |
| YNR076W | YOL037C | YOL077C | YOL115W | YOL156W |
| YNR077C | YOL038W | YOL077W-A | YOL116W | YOL157C |
| YOL001W | YOL039W | YOL078W | YOL117W | YOL158C |
| YOL002C | YOL040C | YOL079W | YOL118C | YOL159C |
| YOL003C | YOL041C | YOL080C | YOL119C | YOL160W |
| YOL005C | YOL042W | YOL082W | YOL120C | YOL161C |
| YOL007C | YOL043C | YOL083W | YOL121C | YOL162W |
| YOL008W | YOL044W | YOL084W | YOL123W | YOL163W |
| YOL009C | YOL046C | YOL085C | YOL124C | YOL164W |
| YOL010W | YOL047C | YOL086C | YOL125W | YOL165C |
| YOL011W | YOL048C | YOL087C | YOL126C | YOL166C |
| YOL012C | YOL050C | YOL088C | YOL127W | YOR001W |
| YOL013C | YOL051W | YOL089C | YOL128C | YOR002W |
| YOL013W-A | YOL052C | YOL090W | YOL129W | YOR003W |
| YOL014W | YOL052C-A | YOL091W | YOL130W | YOR005C |
| YOL015W | YOL053W | YOL092W | YOL131W | YOR006C |
| YOL016C | YOL054W | YOL093W | YOL132W | YOR007C |
| YOL017W | YOL055C | YOL094C | YOL133W | YOR009W |
| YOL018C | YOL056W | YOL095C | YOL134C | YOR010C |
| YOL019W | YOL057W | YOL096C | YOL135C | YOR013W |
| YOL020W | YOL058W | YOL097C | YOL136C | YOR014W |
| YOL021C | YOL059W | YOL098C | YOL137W | YOR015W |
| YOL022C | YOL060C | YOL099C | YOL139C | YOR016C |
| YOL023W | YOL062C | YOL100W | YOL140W | YOR017W |
| YOL024W | YOL063C | YOL101C | YOL141W | YOR018W |
| YOL025W | YOL064C | YOL102C | YOL142W | YOR019W |

FIG. 1Y

| | | | | |
|---|---|---|---|---|
| YOR020C | YOR063W | YOR110W | YOR150W | YOR195W |
| YOR021C | YOR066W | YOR111W | YOR152C | YOR196C |
| YOR022C | YOR067C | YOR112W | YOR154W | YOR197W |
| YOR023C | YOR068C | YOR114W | YOR155C | YOR198C |
| YOR024W | YOR069W | YOR115C | YOR156C | YOR199W |
| YOR025W | YOR070C | YOR117W | YOR157C | YOR200W |
| YOR026W | YOR072W | YOR118W | YOR159C | YOR201C |
| YOR029W | YOR073W | YOR119C | YOR160W | YOR202W |
| YOR030W | YOR074C | YOR120W | YOR161C | YOR203W |
| YOR031W | YOR076C | YOR121C | YOR162C | YOR204W |
| YOR032C | YOR077W | YOR122C | YOR163W | YOR205C |
| YOR033C | YOR079C | YOR123C | YOR164C | YOR206W |
| YOR034C | YOR080W | YOR124C | YOR166C | YOR209C |
| YOR035C | YOR081C | YOR125C | YOR167C | YOR210W |
| YOR036W | YOR082C | YOR126C | YOR168W | YOR212W |
| YOR038C | YOR083W | YOR128C | YOR169C | YOR213C |
| YOR039W | YOR084W | YOR129C | YOR171C | YOR214C |
| YOR040W | YOR085W | YOR130C | YOR173W | YOR215C |
| YOR041C | YOR087W | YOR131C | YOR174W | YOR216C |
| YOR043W | YOR088W | YOR132W | YOR175C | YOR217W |
| YOR044W | YOR089C | YOR133W | YOR176W | YOR218C |
| YOR045W | YOR090C | YOR134W | YOR177C | YOR219C |
| YOR046C | YOR091W | YOR135C | YOR178C | YOR220W |
| YOR047C | YOR092W | YOR136W | YOR179C | YOR221C |
| YOR048C | YOR094W | YOR137C | YOR180C | YOR222W |
| YOR049C | YOR095C | YOR138C | YOR181W | YOR223W |
| YOR050C | YOR096W | YOR139C | YOR182C | YOR224C |
| YOR051C | YOR097C | YOR140W | YOR184W | YOR225W |
| YOR052C | YOR098C | YOR141C | YOR185C | YOR226C |
| YOR053W | YOR099W | YOR142W | YOR186W | YOR227W |
| YOR054C | YOR100C | YOR142W-A | YOR187W | YOR228C |
| YOR055W | YOR102W | YOR144C | YOR188W | YOR229W |
| YOR057W | YOR103C | YOR145C | YOR190W | YOR230W |
| YOR058C | YOR104W | YOR146W | YOR192C | YOR231W |
| YOR060C | YOR105W | YOR147W | YOR192C-A | YOR232W |
| YOR061W | YOR106W | YOR148C | YOR193W | YOR233W |
| YOR062C | YOR107W | YOR149C | YOR194C | YOR234C |

FIG. 1Z

| YOR235W | YOR273C | YOR311C | YOR355W | YPL004C |
| YOR236W | YOR274W | YOR312C | YOR357C | YPL005W |
| YOR237W | YOR275C | YOR313C | YOR358W | YPL007C |
| YOR238W | YOR276W | YOR314W | YOR359W | YPL008W |
| YOR239W | YOR277C | YOR315W | YOR360C | YPL009C |
| YOR240W | YOR278W | YOR316C | YOR361C | YPL010W |
| YOR241W | YOR279C | YOR317W | YOR362C | YPL011C |
| YOR242C | YOR280C | YOR318C | YOR364W | YPL013C |
| YOR243C | YOR281C | YOR319W | YOR365C | YPL015C |
| YOR244W | YOR282W | YOR320C | YOR366W | YPL017C |
| YOR245C | YOR283W | YOR321W | YOR367W | YPL018W |
| YOR246C | YOR284W | YOR322C | YOR368W | YPL019C |
| YOR247W | YOR285W | YOR323C | YOR369C | YPL020C |
| YOR248W | YOR286W | YOR325W | YOR370C | YPL021W |
| YOR249C | YOR287C | YOR327C | YOR371C | YPL023C |
| YOR250C | YOR288C | YOR329C | YOR372C | YPL024W |
| YOR251C | YOR289W | YOR330C | YOR374W | YPL025C |
| YOR252W | YOR292C | YOR332W | YOR375C | YPL026C |
| YOR253W | YOR294W | YOR333C | YOR376W | YPL027W |
| YOR254C | YOR295W | YOR334W | YOR377W | YPL028W |
| YOR255W | YOR296W | YOR335C | YOR378W | YPL029W |
| YOR256C | YOR297C | YOR338W | YOR379C | YPL030W |
| YOR257W | YOR298C-A | YOR339C | YOR383C | YPL031C |
| YOR258W | YOR298W | YOR340C | YOR384W | YPL032C |
| YOR259C | YOR299W | YOR342C | YOR385W | YPL033C |
| YOR260W | YOR300W | YOR343C | YOR386W | YPL034W |
| YOR261C | YOR301W | YOR343C-A | YOR387C | YPL035C |
| YOR262W | YOR302W | YOR344C | YOR388C | YPL036W |
| YOR263C | YOR303W | YOR345C | YOR389W | YPL037C |
| YOR264W | YOR304C-A | YOR347C | YOR390W | YPL038W |
| YOR265W | YOR304W | YOR348C | YOR391C | YPL039W |
| YOR266W | YOR305W | YOR349W | YOR392W | YPL040C |
| YOR268C | YOR306C | YOR350C | YOR393W | YPL041C |
| YOR269W | YOR307C | YOR351C | YOR394W | YPL042C |
| YOR270C | YOR308C | YOR352W | YPL001W | YPL043W |
| YOR271C | YOR309C | YOR353C | YPL002C | YPL044C |
| YOR272W | YOR310C | YOR354C | YPL003W | YPL045W |

FIG. 1A1

| YPL046C | YPL087W | YPL125W | YPL167C | YPL208W |
| YPL047W | YPL088W | YPL126W | YPL168W | YPL210C |
| YPL048W | YPL089C | YPL127C | YPL169C | YPL211W |
| YPL049C | YPL091W | YPL128C | YPL170W | YPL212C |
| YPL050C | YPL092W | YPL129W | YPL171C | YPL213W |
| YPL051W | YPL093W | YPL131W | YPL172C | YPL214C |
| YPL052W | YPL094C | YPL132W | YPL173W | YPL215W |
| YPL053C | YPL095C | YPL133C | YPL174C | YPL218W |
| YPL054W | YPL096W | YPL134C | YPL175W | YPL219W |
| YPL055C | YPL097W | YPL136W | YPL176C | YPL220W |
| YPL056C | YPL098C | YPL137C | YPL177C | YPL221W |
| YPL057C | YPL099C | YPL139C | YPL178W | YPL222W |
| YPL059W | YPL100W | YPL140C | YPL179W | YPL223C |
| YPL060C-A | YPL101W | YPL141C | YPL180W | YPL224C |
| YPL061W | YPL102C | YPL142C | YPL181W | YPL225W |
| YPL062W | YPL103C | YPL143W | YPL182C | YPL226W |
| YPL063W | YPL104W | YPL144W | YPL183W-A | YPL227C |
| YPL064C | YPL105C | YPL145C | YPL185W | YPL229W |
| YPL065W | YPL106C | YPL146C | YPL186C | YPL230W |
| YPL066W | YPL107W | YPL147W | YPL188W | YPL231W |
| YPL067C | YPL108W | YPL148C | YPL189W | YPL232W |
| YPL068C | YPL109C | YPL149W | YPL190C | YPL233W |
| YPL069C | YPL110C | YPL150W | YPL191C | YPL234C |
| YPL070W | YPL111W | YPL151C | YPL192C | YPL235W |
| YPL071C | YPL112C | YPL154C | YPL193W | YPL236C |
| YPL072W | YPL113C | YPL155C | YPL194W | YPL237W |
| YPL073C | YPL114W | YPL156C | YPL196W | YPL238C |
| YPL074W | YPL115C | YPL157W | YPL197C | YPL239W |
| YPL076W | YPL116W | YPL158C | YPL198W | YPL240C |
| YPL077C | YPL117C | YPL159C | YPL199C | YPL241C |
| YPL078C | YPL118W | YPL160W | YPL200W | YPL243W |
| YPL079W | YPL119C | YPL161C | YPL201C | YPL244C |
| YPL080C | YPL120W | YPL162C | YPL202C | YPL245W |
| YPL081W | YPL121C | YPL163C | YPL203W | YPL246C |
| YPL083C | YPL122C | YPL164C | YPL205C | YPL247C |
| YPL084W | YPL123C | YPL165C | YPL206C | YPL249C |
| YPL086C | YPL124W | YPL166W | YPL207W | YPL249C-A |

FIG. 1B1

| YPL250C | YPR006C | YPR047W | YPR085C | YPR130C |
| YPL251W | YPR007C | YPR048W | YPR086W | YPR131C |
| YPL252C | YPR008W | YPR049C | YPR088C | YPR132W |
| YPL253C | YPR009W | YPR050C | YPR089W | YPR133C |
| YPL254W | YPR010C | YPR051W | YPR091C | YPR133W-A |
| YPL255W | YPR011C | YPR052C | YPR092W | YPR134W |
| YPL256C | YPR012W | YPR053C | YPR093C | YPR136C |
| YPL257W | YPR013C | YPR054W | YPR094W | YPR137C-A |
| YPL257W-A | YPR014C | YPR055W | YPR095C | YPR137W |
| YPL258C | YPR015C | YPR056W | YPR096C | YPR138C |
| YPL259C | YPR016C | YPR057W | YPR097W | YPR139C |
| YPL260W | YPR017C | YPR058W | YPR098C | YPR140W |
| YPL261C | YPR018W | YPR059C | YPR099C | YPR141C |
| YPL262W | YPR019W | YPR060C | YPR100W | YPR142C |
| YPL263C | YPR020W | YPR061C | YPR101W | YPR143W |
| YPL264C | YPR022C | YPR062W | YPR102C | YPR144C |
| YPL265W | YPR023C | YPR063C | YPR103W | YPR145W |
| YPL267W | YPR024W | YPR064W | YPR105C | YPR147C |
| YPL268W | YPR025C | YPR065W | YPR107C | YPR148C |
| YPL269W | YPR027C | YPR066W | YPR108W | YPR149W |
| YPL270W | YPR028W | YPR067W | YPR109W | YPR150W |
| YPL271W | YPR029C | YPR068C | YPR110C | YPR151C |
| YPL272C | YPR030W | YPR069C | YPR111W | YPR152C |
| YPL273W | YPR031W | YPR070W | YPR112C | YPR153W |
| YPL275W | YPR032W | YPR071W | YPR113W | YPR154W |
| YPL276W | YPR033C | YPR072W | YPR114W | YPR155C |
| YPL277C | YPR034W | YPR073C | YPR116W | YPR156C |
| YPL278C | YPR035W | YPR074C | YPR118W | YPR157W |
| YPL279C | YPR036W | YPR075C | YPR119W | YPR158C-C |
| YPL280W | YPR037C | YPR077C | YPR121W | YPR158W |
| YPL282C | YPR038W | YPR078C | YPR123C | YPR158W-A |
| YPR001W | YPR039W | YPR079W | YPR124W | YPR159W |
| YPR002C-A | YPR040W | YPR080W | YPR125W | YPR161C |
| YPR002W | YPR043W | YPR081C | YPR126C | YPR162C |
| YPR003C | YPR044C | YPR082C | YPR127W | YPR163C |
| YPR004C | YPR045C | YPR083W | YPR128C | YPR165W |
| YPR005C | YPR046W | YPR084W | YPR129W | YPR166C |

FIG. 1C1

| | | | | |
|---|---|---|---|---|
| YPR167C | YPR175W | YPR183W | YPR193C | YPR202W |
| YPR168W | YPR176C | YPR185W | YPR194C | YPR203W |
| YPR169W | YPR177C | YPR186C | YPR195C | YBL059C-A |
| YPR170C | YPR178W | YPR187W | YPR196W | YHR132W-A |
| YPR171W | YPR179C | YPR188C | YPR197C | YCL027C-A |
| YPR172W | YPR180W | YPR190C | YPR198W | YCL021W-A |
| YPR173C | YPR181C | YPR191W | YPR199C | |
| YPR174C | YPR182W | YPR192W | YPR200C | |

FIG. 1D1

| | | | | | |
|---|---|---|---|---|---|
| araD | eutH | bglG | envZ | b1339 | yhaO |
| araA | eutG | rbsK | ompR | b1384 | yhbM |
| araB | eutJ | rbsR | spoT | b1422 | b3226 |
| araC | eutE | rhaD | phoU | b1439 | b3243 |
| gcd | eutI | rhaA | gppA | b1497 | yhdM |
| sfsA | b2550 | rhaB | cyaA | b1512 | yhfR |
| yagG | srlD | rhaS | cpxA | b1526 | yhgB |
| b0271 | gutM | rhaR | cytR | b1595 | yhhX |
| cynR | srlR | frwC | oxyR | rstA | yhhM |
| lacA | gutQ | frwB | lexA | gusR | yhhI |
| lacZ | ascG | frwD | soxS | ydhB | yhiI |
| lacI | ascB | malM | soxR | b1770 | b3515 |
| mhpB | b2787 | rpiB | creB | b1799 | yhiX |
| b0349 | b2788 | melR | creC | b1827 | yhjB |
| mhpE | b2789 | melA | arcA | uvrY | yhjC |
| b0352 | fucO | b4198 | yaaC | cbl | yiaJ |
| araJ | fucA | treC | yaeG | nac | yiaU |
| malZ | fucI | yjgT | yafC | b2015 | yicM |
| pgm | fucK | gntV | perR | b2056 | yidF |
| b0713 | fucU | yjhF | yagI | b2061 | b3680 |
| ybgB | fucR | uxuA | yagL | yegE | yidP |
| galK | galR | uxuB | yagW | yohI | yidU |
| galT | kduI | uxuR | b0294 | yeiE | b3694 |
| galE | bglA | lytB | ykgA | yeiL | yidY |
| poxB | ygfF | phoB | ykgD | yojN | yidZ |
| focA | glcG | phoR | b0316 | atoS | yifI |
| b1106 | glcD | lon | b0318 | b2248 | yihW |
| galU | glcC | fur | b0330 | b2299 | cpxR |
| uxaB | icc | kdpE | b0346 | b2326 | yiiT |
| mlc | ebgR | kdpD | b0417 | b2380 | yijO |
| manA | ebgA | phoQ | b0447 | b2382 | b3995 |
| uidA | ebgC | phoP | b0504 | b2409 | adiY |
| malI | uxaA | b1320 | b0506 | b2412 | yjdG |
| malY | uxaC | fnr | b0538 | b2428 | yjdH |
| celF | exuR | relB | b0570 | b2537 | yjfQ |
| celD | yhaU | rspB | b0571 | b2556 | yjgS |
| b1772 | agaZ | rspA | b0603 | yfiE | yjhI |
| amyA | nlp | rstB | b0619 | ygaE | yjhJ |
| b2045 | gph | osmE | criR | oraA | yjiE |
| gatR_1 | malQ | suhB | b0705 | ygaA | yjiR |
| gatR_2 | malP | era | ybhD | hypF | yjjQ |
| gatD | malT | rseC | b0805 | b2734 | yjjR |
| gatZ | treF | rseB | b0836 | b2735 | yi81_1 |
| gatY | kdgK | rseA | b0853 | b2768 | insB_1 |
| bglX | xylB | rpoE | b0900 | b2847 | insA_1 |
| galS | xylA | csrA | ycbE | b2852 | yafZ |
| yeiI | xylR | relA | b0986 | b2855 | tra8_1 |
| fruA | malS | barA | b1119 | b2921 | b0257 |
| yeiQ | lyxK | rpoN | b1162 | yggD | yi52_1 |
| pta | aldB | arcB | b1201 | b3025 | insB_2 |
| glk | mtlD | sspB | b1284 | b3026 | insA_2 |
| eutC | mtlR | sspA | b1314 | b3060 | insB_3 |
| eutB | bglB | crp | b1328 | yhaJ | insA_3 |

FIG. 2A

| | | | | | |
|---|---|---|---|---|---|
| b0281 | alpA | dacA | yeeC | rfaF | ychP |
| b0299 | b2633 | mrdB | rfc | rfaC | yciF |
| tra5_1 | emrR | mrdA | rfbX | rfaL | b1368 |
| ybaN | yi22_4 | rlpB | b2059 | rfaK | b1376 |
| intD | yi21_4 | pal | b2062 | rfaZ | b1505 |
| b0539 | yi52_9 | b0795 | yehA | rfaY | b1835 |
| tra5_2 | yi21_5 | ompX | yehD | rfaJ | b1999 |
| yi52_2 | yi22_5 | dacC | pbpG | rfaI | b2004 |
| nmpC | yi52_10 | b0869 | ompC | rfaB | b2007 |
| nohB | insA_6 | b0874 | rcsB | rfaS | b2175 |
| nfrA | insB_6 | kdsB | rcsC | rfaP | b2291 |
| nfrB | yi52_11 | ompF | b2253 | rfaG | yfcA |
| yi81_2 | yi5B | b0938 | mepA | rfaQ | b2338 |
| yi52_3 | hfq | b0940 | b2333 | kdtA | b2438 |
| tolQ | intB | b0941 | b2335 | kdtB | b2506 |
| tolR | b4273 | b0942 | b2339 | rfe | yfhG |
| tolA | tra8_3 | b0943 | b2351 | b3785 | yfiB |
| tolB | b4285 | ompA | amiA | rffT | b2879 |
| insB_4 | insA_7 | b0983 | b2505 | rffM | yggE |
| tra5_3 | creD | csgG | yfgA | rfaH | b2954 |
| lit | murE | csgF | b2519 | murI | yggM |
| b1140 | murF | csgE | smpA | murB | b3051 |
| b1145 | mraY | csgD | mltB | amiB | yhfK |
| b1157 | murD | csgB | mltA | yjfG | yibH |
| pin | murG | csgA | b2817 | fimB | yicC |
| pspF | murC | dsbB | b2865 | fimE | yigN |
| pspA | ddlB | kdsA | dsbC | fimA | yjbB |
| pspB | lpxC | yciD | ygiL | fimI | yjdA |
| pspC | hofC | b1377 | b3046 | fimC | yjeP |
| pspD | hofB | b1424 | b3047 | fimD | yjfJ |
| pspE | htrE | b1433 | glgS | fimF | yjgA |
| yi52_4 | ecpD | b1471 | yraH | fimG | yjjA |
| b1345 | mrcB | b1502 | yraJ | fimH | yjjP |
| racC | fhuA | hipA | yraK | slt | yaaJ |
| sieB | hlpA | hipB | dacB | yaeE | nhaA |
| b1362 | lpxD | lpp | murA | b0489 | nhaR |
| yi52_5 | lpxA | flhA | yrbM | rlpA | lspA |
| b1372 | lpxB | flhC | nanT | b0786 | yaaU |
| b1374 | rcsF | flhD | nanA | b1202 | kefC |
| tra8_2 | yaeC | fliA | mreD | b1472 | secA |
| nohA | gmhA | fliC | mreC | gusC | aroP |
| b1579 | crl | fliD | mreB | nlpC | fhuC |
| insB_5 | phoE | fliS | acrE | vacJ | fhuD |
| insA_5 | yagD | fliT | mrcA | nlpB | fhuB |
| yi52_7 | b0363 | fliE | glgP | nlpD | abc |
| ogrK | ddlA | fliF | glgA | nlpA | betT |
| tra5_4 | yajB | fliG | glgC | blc | codB |
| yi52_8 | bolA | fliH | glgX | yabC | cynX |
| b2292 | b0453 | fliL | glgB | yaeH | lacY |
| cvpA | acrA | fliM | slp | eaeH | brnQ |
| yfdB | b0532 | fliN | yiaD | b0357 | secD |
| b2394 | fimZ | fliO | yiaN | b0465 | secF |
| b2430 | b0558 | fliP | yiaT | ybbB | tsx |
| b2442 | ompT | fliQ | yibP | ybeL | mdlA |
| grpE | envY | fliR | yibD | b0780 | mdlB |
| intA | b0612 | rcsA | rfaD | b0878 | ybaL |

FIG. 2B

| | | | | | |
|---|---|---|---|---|---|
| b0484 | chaB | hisM | gntT | rhaT | ybeJ |
| ybbA | chaC | hisJ | gntU_2 | kdgT | b0660 |
| pheP | narK | argT | gntU_1 | sbp | b0715 |
| fepA | oppA | fadL | ugpC | glpF | b0752 |
| fes | oppB | b2387 | ugpE | ptsA | b0770 |
| fepE | oppC | nupC | ugpA | btuB | b0794 |
| fepC | oppD | xapB | ugpB | secE | b0820 |
| fepG | oppF | ptsH | livF | xylE | b0842 |
| fepD | kch | ptsI | livG | malG | b0879 |
| fepB | tonB | crr | livM | malF | ycaD |
| gltL | sapF | cysA | livH | malE | b0899 |
| gltK | sapD | cysW | livK | malK | b0934 |
| gltJ | sapC | cysU | livJ | lamB | b0949 |
| lnt | sapB | cysP | nikA | gltP | yccA |
| nagE | sapA | bcp | nikB | phnE | ychE |
| potE | tyrR | uraA | nikC | phnD | b1296 |
| kdpC | b1329 | lepB | nikD | phnC | b1311 |
| kdpB | trkG | kgtP | nikE | proP | b1312 |
| kdpA | b1453 | ffh | pitA | melB | b1318 |
| b0709 | b1483 | gabP | yhiP | dcuB | ydaH |
| pnuC | b1484 | proV | dctA | cadB | b1440 |
| modE | b1485 | proW | dppF | dcuA | b1441 |
| modA | b1486 | srlA_1 | dppD | cycA | b1442 |
| modB | uidB | srlA_2 | dppC | treB | b1443 |
| modC | malX | srlB | dppB | mgtA | b1451 |
| glnQ | b1634 | ascF | dppA | fecE | b1452 |
| glnP | btuD | sdaC | xylF | fecD | ydcC |
| glnH | btuE | fucP | xylG | fecC | b1487 |
| b0829 | btuC | ptsP | xylH | fecB | yddA |
| b0830 | celC | araE | mtlA | fecA | b1513 |
| b0831 | celB | cmtA | lldP | fecR | b1514 |
| b0832 | celA | cmtB | secB | fecI | b1515 |
| potF | manX | galP | gltS | yjhN | b1543 |
| potG | manY | nupG | uhpT | gntP | b1592 |
| potH | manZ | b2968 | uhpC | yabJ | ydhC |
| potI | araH | b2970 | uhpB | yabK | b1690 |
| artJ | araG | pitB | uhpA | yabM | b1691 |
| artM | araF | exbD | glvG | yacC | b1729 |
| artQ | ftn | exbB | glvB | yadG | b1756 |
| artI | tyrP | exuT | glvC | yadQ | b1801 |
| artP | gatC | tdcC | tnaB | yaeM | yeeF |
| aqpZ | gatB | mtr | bglF | b0263 | b2074 |
| cydC | gatA | secG | pstB | ykgG | b2077 |
| cydD | molR_1 | ptsN | pstA | b0353 | b2098 |
| lolA | molR_2 | ptsO | pstC | b0365 | yehW |
| msbA | molR_3 | panF | pstS | b0367 | yehX |
| putP | mglC | trkA | kup | b0486 | yehZ |
| msyB | mglA | hofF | rbsD | b0490 | yohG |
| ptsG | mglB | hofG | rbsA | b0491 | yohK |
| fhuE | cirA | hofH | rbsC | b0511 | yeiJ |
| potD | lysP | pshM | rbsB | b0513 | yeiM |
| potC | fruB | bfr | corA | b0572 | yeiO |
| potB | yejE | kefB | trkH | b0574 | yojI |
| potA | yejF | hofQ | frvR | ybdE | b2246 |
| nhaB | glpT | feoA | frvB | ybdG | b2258 |
| chaA | hisP | feoB | frvA | ybdA | b2322 |

FIG. 2C

| | | | | | |
|---|---|---|---|---|---|
| yfdC | b4115 | b0533 | sodB | ftsX | adhC |
| dsdX | b4130 | ybcG | katE | ftsE | cyoE |
| b2372 | yjeH | nfnB | b1828 | ftsY | cyoD |
| b2492 | yjeM | ahpC | htpX | uspA | cyoC |
| b2546 | ptxA | ahpF | b1840 | arsR | cyoB |
| b2547 | ytfQ | ybgD | msbB | arsB | cyoA |
| b2681 | ytfR | dps | cutC | arsC | b0492 |
| b2771 | ytfS | mdaA | b1880 | yhiU | b0604 |
| b2775 | ytfT | b0867 | cheZ | yhiV | b0617 |
| b2832 | yjfF | cspD | cheY | yhjX | fldA |
| b2845 | yjiO | ftsK | cheB | cspA | gltA |
| b2882 | b4356 | mukB | cheR | radC | sdhC |
| b2888 | htgA | sulA | tap | emrD | sdhD |
| ygfD | dnaK | cspG | tar | hslS | sdhA |
| yggB | dnaJ | cbpA | cheW | hslT | sdhB |
| b2950 | gefL | mdoG | cheA | thdF | sucA |
| b2952 | caiF | mdoH | motB | sodA | sucB |
| b2966 | caiE | htrB | motA | hslU | sucC |
| b2975 | caiD | mviM | otsA | ftsN | sucD |
| ygjU | caiC | mviN | otsB | katG | farR |
| b3195 | caiB | flgN | sdiA | htrC | cydA |
| yhbG | caiA | flgM | fliY | yjcR | cydB |
| yhcL | caiT | flgA | fliI | yjcT | gpmA |
| yhdW | ksgA | flgB | fliJ | cutA | b0872 |
| yhdX | imp | flgC | fliK | mopB | dmsA |
| yhdY | ftsL | flgD | b1981 | mopA | dmsB |
| yhdZ | ftsI | flgE | sanA | ampC | dmsC |
| prlA | ftsW | flgF | bcr | treR | pflA |
| yhfC | ftsQ | flgG | inaA | yjiY | pflB |
| yhfM | ftsA | flgH | pmrD | tsr | hyaA |
| yhfN | ftsZ | flgI | usg | mdoB | hyaB |
| yhgE | ampD | flgJ | div | osmY | hyaC |
| b3469 | ampE | flgK | emrY | b0531 | hyaD |
| yhhS | yadC | flgL | emrK | b0717 | hyaE |
| b3486 | yadK | minE | acrD | b0939 | hyaF |
| yhiD | yadL | minD | hscA | ycbF | appC |
| yhjE | yadM | minC | b2630 | yegD | appB |
| yhjV | yadN | treA | b2639 | yehC | torS |
| yiaO | mesJ | osmB | proX | b2336 | torT |
| yiaV | cutF | tpx | emrA | yraI | torR |
| yicE | fhiA | hslJ | emrB | yhcA | torC |
| yicJ | mbhA | trg | b2830 | talB | torA |
| yicL | ykgC | tehA | ygeD | fixA | torD |
| yidK | betA | tehB | ygeA | fixB | b1017 |
| yidE | betB | b1448 | sufI | fixX | ndh |
| yidT | betI | osmC | tolC | fruL | icdA |
| yieG | sbmA | ydeA | bacA | fruR | narL |
| yieO | b0427 | marR | air | pdhR | narX |
| yifK | ampG | marA | yraP | aceE | narG |
| yihN | tig | marB | hflB | aceF | narH |
| b3876 | acrB | cspB | ftsJ | lpdA | narJ |
| yihP | acrR | relF | cafA | acnB | narI |
| yjbK | htpG | dicC | envR | ldcC | adhE |
| yjcV | fsr | dicA | acrF | dniR | acnA |
| yjcW | b0487 | dicB | mscL | b0288 | aldH |
| yjcX | b0530 | sodC | fic | b0328 | ldhA |

FIG. 2D

| | | | | | |
|---|---|---|---|---|---|
| b1392 | nuoH | yhaI | frdB | alkA | hsdS |
| aldA | nuoG | yhaA | frdA | yejH | hsdM |
| gapC_2 | nuoF | yraM | cybC | alkB | mrr |
| gapC_1 | nuoE | mdh | yjjW | ada | dnaC |
| cybB | nuoB | nirB | polB | gyrA | dnaT |
| narV | nuoA | nirD | yacE | b2271 | holD |
| narW | lrhA | nirC | dksA | lig | rob |
| narY | ackA | rpe | rnhB | b2496 | hepA |
| narZ | tktB | glpR | dnaE | recO | pcnB |
| narU | narQ | glpG | rnhA | rnc | hrpB |
| fdnG | yffE | glpE | dnaQ | ung | yi22_1 |
| fdnH | b2482 | glpD | b0247 | recN | sbcC |
| fdnI | b2483 | yhjA | b0354 | b2623 | sbcD |
| b1587 | b2486 | yiaS | hupB | b2644 | nusB |
| b1588 | b2487 | lctR | priC | stpA | xseB |
| b1590 | b2488 | lctD | dnaX | recA | uvrB |
| fumC | b2489 | gpsA | recR | mutS | rhlE |
| fumA | fdx | atpC | rna | mutH | mcrA |
| b1650 | hmpA | atpD | holA | xerD | dbpA |
| pykF | yfiD | atpG | b0650 | iciA | recE |
| b1697 | yfiG | atpA | seqA | mutY | hrpA |
| b1698 | hydN | atpH | ybfD | parC | nth |
| pfkB | hycH | atpF | phrB | parE | xthA |
| b1758 | hycG | atpE | nei | dnaG | uvrC |
| b1773 | hycF | atpB | modF | fis | vsr |
| gapA | hycE | atpI | dinG | yrdD | sbcB |
| zwf | hycD | ubiB | ycaJ | pinO | baeS |
| pykA | hycC | fdhE | himD | dam | baeR |
| b1873 | hycB | fdoI | helD | tag | nfo |
| gnd | hycA | fdoH | rne | mutM | evgA |
| dld | hypA | fdoG | holB | dfp | evgS |
| fruK | hypB | fdhD | mfd | rph | xseA |
| narP | hypC | pfkA | umuD | dinD | srmB |
| ccmH | hypD | tpiA | umuC | recG | yfiA |
| dsbE | hypE | fpr | tpr | gyrB | rpoS |
| ccmF | fhlA | talC | hnr | recF | exo |
| ccmE | ygbE | pflD | hns | dnaN | recD |
| ccmD | b2769 | pflC | topA | dnaA | recB |
| ccmC | b2770 | ppc | rnb | rnpA | recC |
| ccmB | eno | hydH | ogt | gidB | recJ |
| ccmA | b2886 | hydG | lar | gidA | endA |
| napC | fldB | pgi | recT | mioC | rpoD |
| napB | rpiA | qor | b1360 | rep | deaD |
| napH | fba | nrfA | tus | xerC | pnp |
| napG | pgk | nrfB | rnt | uvrD | nusA |
| napA | tktA | nrfC | lhr | recQ | rpoA |
| napF | hybG | nrfD | himA | polA | greB |
| glpA | hybF | nrfE | topB | priA | rpoH |
| glpB | hybE | nrfF | rnd | hupA | rpoZ |
| glpC | hybD | nrfG | b1808 | dnaB | spoU |
| nuoN | hybC | fdhF | holE | uvrA | rhlB |
| nuoM | hybB | yjcU | ruvB | ssb | rhoL |
| nuoL | hybA | rpiR | ruvA | mutL | rho |
| nuoK | ttdA | fumB | ruvC | aidB | nusG |
| nuoJ | ttdB | frdD | dcm | priB | rpoB |
| nuoI | yhaH | frdC | b2002 | holC | rpoC |

FIG. 2E

| | | | | | |
|---|---|---|---|---|---|
| basS | rplT | rpsD | pepE | trpE | ilvN |
| basR | rpmI | rpsK | lysU | trpL | ilvB |
| mcrD | infC | rpsM | efp | cysB | tnaL |
| mcrC | thrS | rpmJ | miaA | tynA | tnaA |
| mcrB | selD | rplO | hflX | b1605 | asnC |
| hsdR | sppA | rpmD | hflK | aroD | asnA |
| rpsT | prc | rpsE | hflC | aroH | ilvL |
| ileS | ptrB | rplR | rpsF | b1748 | ilvG_1 |
| yadB | aspS | rplF | rpsR | gdhA | ilvG_2 |
| htrA | argS | rpsH | rplI | ansA | ilvM |
| map | metG | rpsN | fklB | b1800 | ilvE |
| rpsB | rplY | rplE | msrA | sdaA | ilvD |
| tsf | yejO | rplX | pmbA | hisL | ilvA |
| frr | eco | rplN | valS | hisG | ilvY |
| proS | truA | rpsQ | pepA | hisD | ilvC |
| prfH | b2385 | rpmC | iadA | hisC | dapF |
| pepD | gltX | rplP | rimI | hisB | metR |
| b0296 | b2490 | rpsC | prfC | hisH | metE |
| queA | hisS | rplV | lplA | hisA | glnG |
| tgt | lepA | rpsS | sms | hisF | glnL |
| clpP | clpB | rplB | thrL | hisI | glnA |
| clpX | rplS | rplW | thrA | wcaB | metJ |
| b0441 | trmD | rplD | thrB | aroC | metB |
| hha | rpsP | rplC | thrC | dsdC | metL |
| ppiB | b2647 | rpsJ | dapB | dsdA | argE |
| cysS | alaS | hofD | leuD | cysK | argC |
| b0546 | pcm | tufA | leuC | cysM | argB |
| leuS | iap | fusA | leuB | yffG | argH |
| b0648 | ygcA | rpsG | leuA | dapE | metA |
| ybeK | ptr | rpsL | leuL | dapA | metH |
| glnS | lysS | fkpA | leuO | glyA | lysC |
| hrsA | prfB | slyD | ilvI | glnB | alr |
| rimK | pepP | ppiA | ilvH | pheL | tyrB |
| clpA | b3020 | trpS | dapD | pheA | adi |
| infA | glnE | prlC | glnD | tyrA | cadA |
| aat | cca | yhjS | proB | aroF | cadC |
| serS | ygjD | glyS | proA | sdaB | argI |
| rpsA | rpsU | glyQ | yagF | argA | serB |
| mukF | ygjH | selB | argF | lysA | trpR |
| asnS | sohA | selA | proC | lysR | carA |
| pepN | yhbU | rpmG | aroL | serA | carB |
| rmf | rpsO | rpmB | aroM | ansB | apaH |
| b1031 | truB | rpmH | asnB | metC | mutT |
| rimJ | rbfA | yifB | aroG | tdcB | guaC |
| rpmF | infB | ppiC | ybiK | tdcA | hpt |
| pepT | greA | pepQ | serC | tdcR | gpt |
| pth | rpmA | dsbA | aroA | argG | codA |
| prfA | rplU | yihK | aspC | argR | apt |
| sohB | rpsI | hslV | wrbA | aroE | adk |
| rimL | rplM | rpmE | putA | argD | gsk |
| rpsV | hhoA | trmA | dadA | aroB | purK |
| dcp | hhoB | tufB | dadX | aroK | purE |
| tyrS | prmA | rplK | trpA | asd | deoR |
| pheT | def | rplA | trpB | avtA | trxB |
| pheS | fmt | rplJ | trpC | cysE | cmk |
| pheM | rplQ | rplL | trpD | tdh | pyrD |

FIG. 2F

| | | | | | |
|---|---|---|---|---|---|
| pyrC | pgpB | glnK | cpsB | agaA | tbpA |
| tmk | fabI | amtB | udk | agaS | nadC |
| purB | b1395 | ushA | mrp | agaY | panD |
| prsA | b1397 | b0482 | yeiG | agaB | panC |
| purU | b1409 | gcl | yejM | agaC | panB |
| tdk | acpD | gip | glpQ | agaD | folK |
| pyrF | cfa | b0512 | b2302 | agaI | hemL |
| add | fadD | b0517 | hisQ | mrsA | hemB |
| purR | pgsA | ybcF | b2342 | gltB | ribD |
| purT | atoC | appY | b2379 | gltD | ribH |
| amn | accD | ybdH | b2383 | gltF | ispA |
| dcd | fabB | b0600 | xapR | prkB | hemH |
| cdd | b2341 | b0608 | xapA | damX | folD |
| nrdA | acpS | rnk | cysZ | pckA | entD |
| nrdB | pssA | nagD | b2463 | gntK | entF |
| purF | lgt | nagC | b2464 | gntR | entC |
| purC | aas | nagA | gcvR | ugpQ | entE |
| upp | b2844 | nagB | b2484 | gadA | entB |
| purM | sbm | b0689 | b2491 | kbl | entA |
| purN | plsC | speF | ppk | glmS | lipA |
| guaA | accB | b0711 | ppx | glmU | lipB |
| guaB | accC | b0712 | sseA | rffE | phpB |
| ndk | yhjY | b0718 | yfhI | rffD | nadA |
| purL | pssR | galM | b2530 | rffG | bioA |
| thyA | fadA | ybhA | b2536 | rffH | bioB |
| dut | fadB | ybhE | b2538 | aslB | bioF |
| pyrE | cdh | ybhC | b2539 | aslA | bioC |
| gmk | arp | b0789 | b2540 | pldA | bioD |
| udp | plsB | b0825 | yfhA | pldB | moaA |
| purD | dgkA | lrp | gabD | glpK | moaB |
| purH | acs | yccK | gabT | metF | moaC |
| purA | psd | appA | nrdE | gldA | moaD |
| cpdB | yjgI | agp | nrdF | aceB | moaE |
| nrdD | speD | b1009 | cysC | aceA | moeB |
| pyrI | speE | phoH | cysN | aceK | moeA |
| pyrB | dgt | goaG | cysD | iclR | grxA |
| pyrL | pyrH | sfcA | cysH | phnP | pncB |
| deoC | yaeD | gadB | cysI | phnO | grxB |
| deoA | yafB | speG | cysJ | phnN | pabC |
| deoB | b0217 | pntB | b2765 | phnM | hemM |
| deoD | b0219 | pntA | pyrG | phnL | hemA |
| cdsA | b0221 | hdhA | gcvA | phnK | hemK |
| fabZ | yafJ | ydiD | kduD | phnJ | btuR |
| accA | ykfD | ppsA | gcvP | phnI | ribA |
| tesB | yagC | b1757 | gcvH | phnH | gst |
| ybaC | yagE | b1759 | gcvT | phnG | pdxH |
| tesA | yagT | eda | epd | phnF | ribE |
| fabA | b0331 | edd | speB | dsbD | nadE |
| plsX | b0333 | ntpA | speA | aspA | pabB |
| fabH | cynT | bisZ | metK | cysQ | cobT |
| fabD | cynS | rfbC | speC | ppa | cobS |
| fabG | b0355 | rfbA | glcB | fbp | cobU |
| acpP | b0366 | rfbD | gsp | nrdG | folE |
| fabF | phoA | rfbB | agaR | mog | ubiG |
| fadR | psiF | galF | agaV | folA | menE |
| cls | b0419 | cpsG | agaW | pdxA | menC |

FIG. 2G

| | | | | | |
|---|---|---|---|---|---|
| menB | b0485 | b1338 | b2298 | b3011 | yjcQ |
| menD | b0493 | b1378 | b2304 | yqiB | yjfC |
| menF | b0496 | b1385 | b2324 | ygiC | ytfL |
| b2303 | b0509 | b1393 | yfcB | b3050 | yjgU |
| ubiX | b0516 | b1394 | b2355 | b3052 | yjgV |
| folC | b0518 | ydbC | b2373 | ygjG | yjgB |
| pdxB | b0520 | b1408 | yfeN | ygjI | yjhC |
| hemF | b0615 | b1411 | yfeH | ygjL | yjhG |
| pdxJ | b0616 | b1435 | b2418 | yqjG | yjhM |
| nadB | b0618 | b1444 | yfeF | yhaE | yjhP |
| gshA | b0626 | b1449 | b2429 | yhaG | yjhR |
| ubiH | b0646 | b1454 | b2495 | yhbW | yjiL |
| gshB | b0658 | b1463 | b2511 | yhbX | yjjN |
| b2955 | ybiB | b1478 | b2512 | yrbH | yjjT |
| ribB | ybiC | b1498 | yfgB | yhcI | yjjG |
| folP | b0804 | b1501 | b2532 | b3223 | surA |
| ispB | b0815 | b1524 | b2534 | yhcQ | ppdD |
| pabA | b0823 | b1525 | b2541 | yhdH | dinJ |
| cysG | b0824 | ydfG | b2542 | yhdG | cspE |
| bioH | b0837 | b1542 | b2545 | yhdJ | pqiA |
| ggt | b0838 | b1680 | yfhD | b3279 | pqiB |
| gor | b0847 | ydiB | yfhC | yheB | b0989 |
| bisC | b0859 | b1695 | sfhB | yhfQ | dinI |
| grxC | b0865 | b1746 | b2657 | yhfV | xasA |
| trxA | b0868 | b1774 | b2668 | yhfW | cspF |
| hemY | b0870 | b1776 | b2710 | yrfF | asr |
| hemX | b0877 | b1781 | ygbD | yrfG | cspC |
| hemD | ycaH | b1803 | b2736 | b3468 | sbmC |
| hemC | ycbB | b1919 | b2738 | yhhU | ais |
| mobA | b0955 | b1971 | b2740 | yhjL | sseB |
| hemN | ycbG | b2016 | b2774 | yhjM | surE |
| menG | b0982 | yefJ | ygcE | yiaE | chpA |
| menA | b1006 | yefH | b2867 | b3575 | chpR |
| birA | b1011 | b2044 | b2868 | yiaL | ppdC |
| coaA | b1033 | b2047 | b2869 | yiaY | ppdB |
| thiH | b1059 | yefA | b2871 | b3592 | ppdA |
| thiG | yceG | b2054 | b2872 | yicF | mdaB |
| thiF | b1118 | b2055 | b2874 | yidJ | yhbZ |
| thiE | b1134 | yegA | b2875 | yidX | sugE |
| thiC | b1168 | b2070 | b2878 | b3715 | chpS |
| hemE | b1180 | b2100 | b2881 | yieK | chpB |
| ubiC | ycgC | b2104 | b2885 | yieL | b0005 |
| ubiA | b1199 | yohF | b2887 | yifJ | yaaA |
| nadR | b1200 | b2146 | b2889 | yigB | yaaH |
| b0011 | b1266 | yeiA | b2899 | b3830 | yaaI |
| yabF | yciK | yeiC | ygfA | yigZ | yi82_1 |
| yadF | b1287 | atoD | b2919 | yihG | b0024 |
| yadI | b1297 | atoA | b2920 | yihQ | yaaD |
| yafE | b1298 | b2224 | b2931 | yihR | yaaF |
| b0323 | ordL | b2247 | b2972 | yihT | fixC |
| b0324 | b1309 | b2254 | b2974 | yihU | apaG |
| b0325 | b1313 | b2255 | b2978 | yihV | yabH |
| b0350 | b1315 | yfbB | b2997 | yihX | yabP |
| b0374 | b1321 | b2269 | b3001 | yiiD | yabQ |
| b0420 | b1325 | b2290 | b3003 | udhA | yabO |
| yajG | b1326 | b2293 | b3010 | yjcP | yabI |

FIG. 2H

| | | | | | |
|---|---|---|---|---|---|
| yabN | yagK | b0395 | b0561 | b0762 | b0946 |
| yabB | b0279 | b0402 | b0562 | b0769 | b0947 |
| yacA | b0280 | yajC | b0563 | b0771 | b0948 |
| b0100 | yagP | yajD | ybcH | ybhB | b0952 |
| yacG | yagQ | yajI | b0573 | b0787 | b0959 |
| yacF | yagR | ybaD | ybdF | b0788 | b0960 |
| b0105 | yagS | b0418 | b0580 | b0790 | yccF |
| yacH | yagU | b0423 | b0581 | b0791 | yccG |
| yacL | yagV | thiJ | ybdB | b0792 | b0964 |
| yacK | yagX | apbA | b0598 | b0793 | b0965 |
| yadH | yagY | b0426 | b0601 | ybiH | b0966 |
| yadE | yagZ | b0442 | b0602 | ybiA | b0967 |
| yadD | b0295 | b0443 | b0607 | ybiJ | b0968 |
| yadP | b0298 | b0444 | b0609 | ybiI | yccC |
| yadR | ykgB | ybaE | b0613 | b0806 | b0984 |
| yadS | b0302 | cof | b0614 | b0807 | b0985 |
| yadT | b0303 | b0454 | b0621 | b0808 | b0987 |
| pfs | ykgE | ybaA | ybeG | ybiF | sfa |
| yaeI | ykgF | b0457 | ybeI | b0816 | b0992 |
| b0165 | b0309 | b0458 | ybeH | b0817 | yccD |
| b0174 | ykgH | b0459 | ybeC | b0818 | yccE |
| yaeL | yahA | ybaJ | ybeF | b0819 | yccJ |
| b0177 | b0317 | ybaM | ybeD | b0821 | b1005 |
| b0187 | b0319 | ybaB | ybeA | b0822 | b1007 |
| yaeO | b0320 | b0481 | ybeB | b0833 | b1008 |
| yaeQ | b0321 | b0483 | b0639 | b0834 | b1010 |
| yaeJ | b0322 | b0488 | b0644 | b0835 | b1012 |
| yaeF | b0326 | rhsD | b0645 | b0841 | b1013 |
| yaeB | b0327 | ybbC | b0647 | b0843 | b1016 |
| yafD | b0329 | b0499 | b0649 | b0844 | b1018 |
| b0212 | b0332 | ybbD | b0659 | b0845 | ycdB |
| b0213 | b0334 | b0501 | b0661 | b0846 | b1021 |
| b0218 | b0335 | b0502 | b0662 | b0848 | b1022 |
| b0220 | b0347 | b0505 | b0663 | ybjC | b1023 |
| yafK | b0358 | b0510 | b0667 | b0858 | b1024 |
| yafQ | b0359 | b0514 | b0669 | b0866 | b1025 |
| yafL | yi21_1 | b0515 | b0671 | b0873 | b1027 |
| yafM | b0362 | b0519 | b0681 | b0876 | b1028 |
| dinP | b0364 | ybbF | b0682 | b0881 | b1029 |
| yafN | b0368 | ybcI | b0685 | ycaC | b1030 |
| yafO | b0370 | ybcJ | b0686 | ycaK | b1034 |
| yafP | b0371 | b0540 | ybfG | b0905 | b1035 |
| b0235 | b0373 | b0542 | ybfH | b0906 | b1036 |
| yafA | b0375 | b0543 | ybfA | b0909 | b1043 |
| b0245 | yaiH | b0544 | rhsC | ycaI | b1044 |
| yafW | b0378 | b0545 | ybfB | b0916 | b1045 |
| yafX | b0379 | b0547 | b0703 | b0917 | b1046 |
| b0249 | b0380 | b0548 | ybfC | b0919 | b1047 |
| ykfB | yaiB | b0549 | ybgA | ycbC | yceK |
| yafY | yaiC | b0550 | b0710 | smtA | b1052 |
| ykfA | yaiI | b0551 | b0716 | mukE | yceE |
| b0255 | yaiA | b0554 | b0725 | b0926 | yceA |
| ykfC | yaiE | b0555 | ybgE | b0927 | yceI |
| yagB | b0392 | b0556 | ybgC | b0935 | b1057 |
| yagA | yaiD | b0557 | ybgF | b0936 | b1058 |
| yagJ | yajF | b0559 | b0753 | b0937 | b1060 |

FIG. 2I

| | | | | | |
|---|---|---|---|---|---|
| yceB | b1177 | b1346 | b1458 | b1566 | b1672 |
| b1065 | b1178 | ydaC | b1459 | b1567 | b1673 |
| yceH | b1179 | ydaD | ydcE | b1568 | b1674 |
| b1085 | b1181 | b1354 | b1462 | ydfA | b1675 |
| yceC | b1182 | b1355 | yddE | ydfB | b1678 |
| yceF | ycgB | b1356 | b1470 | ydfC | b1679 |
| yceD | b1191 | b1357 | yddG | ydfD | b1681 |
| ycfH | b1192 | b1358 | b1477 | ydfE | b1682 |
| ycfF | b1193 | b1359 | b1481 | b1578 | b1683 |
| b1104 | b1194 | b1361 | b1488 | b1582 | b1684 |
| b1105 | b1195 | b1364 | b1489 | b1583 | b1685 |
| b1107 | b1196 | b1365 | b1490 | b1585 | b1686 |
| b1108 | ychF | b1366 | b1491 | b1586 | b1687 |
| ycfJ | ychH | b1367 | yddC | b1589 | b1688 |
| b1111 | ychM | b1369 | yddB | b1591 | b1689 |
| b1112 | ychB | b1371 | b1499 | b1593 | ydiF |
| b1113 | b1213 | b1373 | b1500 | b1596 | b1696 |
| b1115 | ychA | b1375 | b1503 | b1598 | b1699 |
| b1116 | ychN | b1381 | b1504 | b1599 | b1700 |
| b1117 | b1228 | b1382 | b1506 | b1600 | ydiA |
| b1120 | ychJ | b1383 | b1509 | b1601 | ydiE |
| b1121 | ychK | b1387 | ydeK | b1604 | b1706 |
| b1122 | ychG | b1388 | b1511 | b1606 | b1707 |
| ycfD | b1240 | b1389 | b1516 | b1607 | b1720 |
| ycfC | b1248 | b1390 | b1517 | b1614 | b1721 |
| ycfB | ycil | b1391 | b1518 | b1624 | b1722 |
| b1135 | yciA | b1396 | b1519 | b1625 | b1724 |
| b1137 | yciB | b1398 | b1520 | b1626 | b1725 |
| b1138 | yciC | b1399 | b1522 | b1627 | b1726 |
| b1141 | yciE | b1400 | b1523 | b1628 | b1727 |
| b1142 | yciG | ydbA_1 | b1527 | b1629 | b1728 |
| b1143 | yciO | yi22_2 | ydeB | b1630 | b1730 |
| b1144 | yciQ | yi21_2 | ydeD | b1631 | b1731 |
| b1146 | yciL | ydbA_2 | ydeF | b1632 | ydjC |
| b1147 | yciN | ydbD | ydeH | b1636 | b1741 |
| b1148 | b1279 | b1410 | ydel | ydhA | b1742 |
| b1149 | yciM | ydcF | ydeJ | b1640 | b1743 |
| b1150 | yciH | b1419 | b1540 | b1641 | b1744 |
| b1151 | b1285 | b1420 | b1541 | b1642 | b1745 |
| b1152 | ycjD | b1423 | b1544 | b1643 | b1747 |
| b1153 | b1295 | b1425 | b1545 | b1644 | b1750 |
| ycfK | ycjC | ydcH | b1546 | b1645 | b1751 |
| b1155 | b1310 | b1428 | b1547 | b1647 | b1752 |
| ycfA | b1316 | b1431 | b1549 | b1648 | b1753 |
| b1160 | b1317 | b1432 | b1550 | b1649 | b1754 |
| b1161 | b1319 | b1434 | b1551 | b1651 | b1755 |
| b1163 | ycjF | b1436 | b1552 | ydhD | b1760 |
| b1164 | b1327 | b1437 | b1553 | b1655 | b1762 |
| b1165 | b1330 | b1438 | b1554 | b1657 | ydjA |
| b1166 | b1332 | b1445 | b1555 | ydhE | ydjB |
| b1167 | ydaA | b1446 | b1556 | b1664 | ydjE |
| b1169 | b1337 | b1447 | b1559 | b1667 | b1771 |
| b1170 | b1340 | b1450 | b1560 | b1668 | b1775 |
| b1171 | b1341 | b1455 | rem | b1669 | b1777 |
| b1172 | b1342 | rhsE | relE | b1670 | b1778 |
| b1173 | b1344 | ydcD | b1565 | b1671 | b1780 |

FIG. 2J

| | | | | | |
|---|---|---|---|---|---|
| b1782 | b1870 | b2000 | yohH | b2332 | b2461 |
| b1783 | b1871 | b2001 | yohJ | b2334 | b2462 |
| b1784 | b1875 | b2003 | b2145 | b2337 | b2466 |
| b1785 | b1877 | b2005 | yeiB | b2340 | yffH |
| b1786 | b1878 | b2006 | yeiH | b2343 | yffB |
| b1787 | yecG | yeeA | yeiK | b2345 | b2473 |
| b1788 | b1899 | yeeD | yeiN | b2350 | b2474 |
| b1789 | yecI | yeeE | yeiP | b2352 | b2475 |
| b1790 | b1903 | yefM | yeiR | b2353 | b2485 |
| b1791 | b1904 | b2027 | b2174 | b2354 | b2493 |
| b1792 | yecH | b2028 | b2176 | b2356 | b2494 |
| b1793 | yecA | yefI | yejA | b2357 | b2503 |
| b1794 | yecF | yefG | yejB | b2358 | b2504 |
| b1795 | b1917 | yefE | yejG | b2359 | b2510 |
| b1796 | yecC | b2043 | yejD | b2360 | b2513 |
| b1797 | fliZ | b2046 | yejK | b2361 | gcpE |
| b1798 | yedD | yefD | yejL | b2362 | b2520 |
| b1802 | yedE | yefC | b2191 | b2363 | yfhJ |
| b1806 | yedF | yefB | yojF | b2371 | yfhE |
| b1807 | yedG | b2057 | yojH | b2374 | yfhF |
| b1809 | b1932 | b2060 | yojL | b2375 | b2529 |
| b1810 | b1933 | b2063 | atoB | b2376 | b2531 |
| b1811 | b1934 | b2071 | b2225 | b2377 | csiE |
| yeaB | b1935 | b2072 | b2226 | b2378 | b2543 |
| b1815 | b1936 | b2073 | b2227 | b2381 | b2544 |
| b1816 | dsrB | b2075 | b2228 | b2384 | b2548 |
| b1820 | b1953 | b2076 | b2229 | b2386 | b2549 |
| b1821 | b1955 | b2080 | yfaA | b2389 | yfhB |
| yebH | b1956 | b2081 | yfaL | b2390 | yfhH |
| b1824 | b1957 | b2083 | yfaE | b2391 | b2562 |
| b1825 | yedI | b2084 | yfaH | b2392 | yfiC |
| b1826 | yedA | b2085 | b2244 | yfeA | yfiK |
| yebJ | yedJ | b2086 | b2245 | yfeC | yfiF |
| b1832 | b1963 | b2097 | b2249 | yfeD | b2583 |
| b1833 | b1964 | b2099 | b2250 | b2419 | b2584 |
| b1834 | b1965 | b2101 | b2251 | b2420 | yfiM |
| b1836 | b1966 | b2102 | b2256 | b2427 | yfiH |
| b1837 | b1967 | b2103 | b2257 | b2431 | b2595 |
| b1838 | b1968 | b2105 | b2266 | b2432 | b2596 |
| b1839 | b1969 | b2106 | b2267 | b2433 | yfiL |
| b1841 | b1970 | b2107 | b2268 | b2434 | b2603 |
| b1843 | b1972 | yehB | b2270 | yfeG | yfiN |
| b1844 | b1973 | yehE | b2272 | b2439 | yfjA |
| yebE | b1974 | yehI | b2273 | b2443 | b2611 |
| yebF | b1976 | yehL | b2274 | b2444 | b2612 |
| yebG | b1978 | b2120 | b2275 | b2445 | yfjD |
| yebK | b1979 | yehP | b2286 | b2446 | yfjB |
| yebA | b1980 | yehQ | b2294 | b2447 | b2618 |
| yebL | b1983 | yehR | b2295 | b2448 | b2619 |
| b1858 | b1985 | yehS | b2300 | b2449 | smpB |
| yebI | erfK | yehT | b2301 | b2450 | b2625 |
| yebB | yi52_6 | yehU | b2305 | b2451 | b2626 |
| yebC | b1995 | yehV | dedD | cchB | b2627 |
| yecD | yi22_3 | yehY | dedA | cchA | b2628 |
| yecE | yi21_3 | yohC | b2325 | b2459 | b2629 |
| b1869 | b1998 | yohD | b2331 | | b2631 |

FIG. 2K

| | | | | | |
|---|---|---|---|---|---|
| b2632 | b2772 | yqgD | ygjK | yhbL | yhfY |
| b2634 | b2773 | sprT | ygjM | yhcC | yhfZ |
| b2635 | b2777 | yggJ | ygjN | yhcD | yrfA |
| b2636 | b2778 | b2948 | ygjO | yhcE | yrfB |
| b2637 | mazG | b2949 | ygjP | b3219 | yrfC |
| b2638 | b2790 | b2951 | ygjQ | yhcG | yrfD |
| b2640 | b2791 | b2953 | ygjR | b3221 | yrfE |
| b2641 | b2792 | yggN | ygjT | yhcM | yrfH |
| b2642 | syd | yggL | ygjV | yhcB | yrfI |
| b2643 | b2794 | yggH | b3095 | b3238 | yhgF |
| b2645 | ygdH | b2962 | yqjB | b3239 | yhgG |
| b2646 | ygdE | yggZ | yqjC | yhcP | yhgA |
| b2648 | ygdD | b2969 | yqjD | b3242 | yhgH |
| b2649 | b2809 | b2971 | yqjE | tldD | yhgI |
| b2650 | b2810 | b2973 | b3100 | b3245 | yhgJ |
| b2651 | b2811 | b2981 | yqjF | yhdR | yhgK |
| b2653 | b2812 | b2983 | yhaK | yhdE | yhgL |
| b2654 | ygdB | b2984 | yhaL | yhdA | yzgL |
| b2655 | b2833 | b2985 | yhaM | b3254 | b3434 |
| b2656 | b2834 | b2986 | yhaN | yhdT | yhhW |
| b2658 | b2846 | b2989 | yhaP | b3263 | b3441 |
| b2659 | b2848 | b2998 | yhaQ | yhdV | yhhZ |
| ygaF | b2849 | b2999 | yhaR | yrdB | b3443 |
| b2665 | b2850 | b3000 | yhaS | yrdC | yrhB |
| b2666 | b2851 | b3002 | yhaB | smg | yhhA |
| b2667 | b2853 | b3004 | yhaC | smf_1 | yhhK |
| b2670 | b2854 | b3007 | b3122 | smf_2 | yhhF |
| ygaC | b2856 | yghB | yhaD | fmu | b3466 |
| b2672 | b2857 | b3012 | yhaF | yhdN | yhhP |
| b2673 | b2858 | b3013 | yhaV | yheD | yhhQ |
| b2674 | b2859 | b3014 | yraL | yheE | b3472 |
| b2680 | b2862 | b3015 | yraN | yheF | yhhT |
| b2682 | b2863 | b3016 | yraO | yheG | yhhG |
| ygaH | b2866 | b3021 | yraQ | yheH | rhsB |
| ygaG | b2870 | b3022 | yraR | yheI | yhhH |
| b2689 | b2873 | b3023 | yhbO | yheJ | yhhJ |
| b2690 | b2876 | b3024 | yhbP | yheK | yhiJ |
| ygaD | b2877 | b3027 | yhbQ | yheA | yhiK |
| hycI | b2880 | ygiN | b3156 | yheL | yhiL |
| ygbA | b2883 | yqiA | yhbT | b3344 | yhiM |
| b2737 | b2884 | b3034 | yhbV | yheN | yhiN |
| b2739 | b2896 | ygiA | yhbC | b3346 | yhiO |
| b2745 | b2897 | ygiB | yhbY | slyX | yhiQ |
| ygbB | b2898 | ygiD | yhbE | yheR | yhiR |
| b2747 | b2900 | ygiE | yrbA | yheS | yhiS |
| b2748 | visC | b3042 | yrbB | yheT | yhiF |
| ygbF | ygfB | b3048 | yrbC | yheU | hdeB |
| b2755 | ygfE | ygiF | b3193 | b3356 | hdeA |
| b2756 | b2915 | ygiM | yrbE | yhfG | hdeD |
| b2757 | yggA | ygiG | yrbG | yhfL | yhiE |
| b2758 | yggC | ygiH | yrbI | yhfO | yhjD |
| b2759 | yggF | ygiE | yrbK | yhfP | b3524 |
| b2760 | b2932 | b3068 | yhbN | yhfS | yhjH |
| ygcB | yggG | b3070 | yhbH | yhfT | yhjJ |
| b2766 | yqgB | b3071 | b3205 | yhfU | yhjK |
| b2767 | yqgC | ygjJ | b3207 | yhfX | yhjN |

FIG. 2L

| | | | | | |
|---|---|---|---|---|---|
| b3533 | yieN | yiiU | yjeK | yjgY | rrlH |
| b3534 | yieP | yiiX | yjeA | yjgZ | rrfH |
| b3535 | yifA | yijE | yjeN | yi41 | aspU |
| b3537 | yifE | yijF | yjeO | yjhB | aspV |
| yhjU | b3776 | yijI | yjeQ | yjhD | thrW |
| yhjW | b3777 | yijP | yjeR | yjhE | ffs |
| yiaC | yifH | yijC | yjeS | yi91 | argU |
| yiaF | cyaY | yijD | yjeF | b4286 | glnX |
| yiaG | o161 | b3975 | yjeE | yjhU | glnV |
| yi5A | yigA | yjaD | b4176 | yjhH | metU |
| yiaH | b3814 | yjaF | yjeB | yjhK | glnW |
| yiaA | yigE | yjaG | vacB | yjhL | glnU |
| yiaB | yigF | yjaH | yjfH | yjhO | leuW |
| b3570 | yigG | yjaI | yjfI | yjhQ | metT |
| b3573 | rarD | yjaA | yjfK | yjhS | lysT |
| yiaM | yigI | yjaB | yjfL | yjhT | valT |
| yiaQ | yigJ | yjbC | yjfM | yjhA | lysW |
| yiaR | yigK | yjbD | yjfN | yjiC | valZ |
| yiaW | yigL | yjbE | yjfO | yjiD | lysY |
| rhsA | yigM | yjbF | yjfP | yjiG | lysZ |
| yibA | yigO | yjbG | yjfR | yjiH | lysQ |
| yibJ | yigP | yjbH | yjfS | yjiI | serW |
| yibG | b3835 | yjbA | yjfT | yjiJ | serT |
| yibI | b3836 | yjbI | yjfV | yjiK | serX |
| yibL | b3837 | dinF | yjfW | yjiM | tyrV |
| yibK | b3838 | b4045 | yjfY | yjiN | tyrT |
| yibN | yigU | yjbL | yjfZ | yjiP | dicF |
| yibO | yigW_1 | yjbM | ytfA | yjiQ | valV |
| yibQ | yigW_2 | yjbN | b4206 | b4341 | valW |
| b3618 | yigC | yjbO | b4209 | yjiT | leuZ |
| ttk | b3850 | yjbP | ytfF | b4343 | cysT |
| yicG | b3856 | yjbQ | ytfG | yjiW | glyW |
| yicH | yihD | yjbR | b4212 | yjiA | dsrA |
| yicI | yihE | yjcB | b4215 | yjiX | serU |
| yicK | yihF | yjcC | ytfJ | yjjM | asnT |
| yicN | b3865 | yjcD | ytfK | yjjB | asnW |
| yicO | yihI | yjcE | ytfM | yjjS | asnU |
| yicP | b3872 | yjcF | ytfN | yjjU | asnV |
| b3672 | yihM | yjcG | ytfP | yjjV | proL |
| yidG | b3875 | yjcH | yjfA | yjjI | argW |
| yidH | yihS | yjcO | yjgF | yjjJ | alaX |
| o149 | yihY | yjcS | yjgG | smp | alaW |
| o135 | yihZ | phnQ | yjgH | yjjK | valU |
| yidR | yiiE | b4103 | b4250 | yjjX | valX |
| yidS | yiiF | phnB | b4251 | gpmB | valY |
| yidV | yiiG | phnA | yjgK | creA | lysV |
| yidW | frvX | yjcZ | yjgL | yjjY | rrfG |
| yidA | yiiL | yjdB | yjgD | lasT | rrlG |
| b3698 | yiiM | yjdF | b4256 | b0701 | gltW |
| yidC | b3913 | yjdI | b4257 | b2088 | rrsG |
| yieE | b3914 | yjdJ | yjgP | b4404 | ssrA |
| b3713 | yiiP | yjdK | yjgQ | b4405 | ileY |
| yieI | yiiQ | yjdC | yjgR | | argQ |
| yieJ | yiiR | b4140 | b4272 | rrsH | argZ |
| yieC | yiiS | b4144 | yjgW | ileV | argY |
| b3745 | glpX | yjeJ | yjgX | alaV | argV |

FIG. 2M

| | | | | | |
|---|---|---|---|---|---|
| serV | leuU | rrsC | rrsA | thrU | glyX |
| metZ | rrfF | gltU | ileT | tyrU | glyY |
| metW | thrV | rrlC | alaT | glyT | leuX |
| metV | rrfD | rrfC | rrlA | thrT | leuV |
| glyU | rrlD | aspT | rrfA | rrsE | leuP |
| ssrS | alaU | trpT | spf | gltV | leuQ |
| pheV | ileU | argX | rrsB | rrlE | |
| ileX | rrsD | hisR | gltT | rrfE | |
| rnpB | proK | leuT | rrlB | pheU | |
| metY | selC | proM | rrfB | glyV | |

FIG. 2N

SEQUENCE LISTING

<160> NUMBER OF SEQ ID NOS: 5

<210> SEQ ID NO 1
<211> LENGTH: 42
<212> TYPE: DNA
<213> ORGANISM: Unknown
<220> FEATURE:
<223> OTHER INFORMATION: Forward primer

<400> SEQUENCE: 1
ggaattccag ctgaccacca tgccagagta tacgctactg gc                    42

<210> SEQ ID NO 2
<211> LENGTH: 44
<212> TYPE: DNA
<213> ORGANISM: Unknown
<220> FEATURE:
<223> OTHER INFORMATION: Reverse primer

<400> SEQUENCE: 2
atccccggga attgccatgt catatatcat atctacgatc atgg                  44

<210> SEQ ID NO 3
<211> LENGTH: 44
<212> TYPE: DNA
<213> ORGANISM: Unknown
<220> FEATURE:
<223> OTHER INFORMATION: Forward primer

<400> SEQUENCE: 3
ggaattccag ctgaccacca tgcctggaaa tttatccttc aaag                  44

<210> SEQ ID NO 4
<211> LENGTH: 45

-continued

```
<212> TYPE: DNA
<213> ORGANISM: Unknown
<220> FEATURE:
<223> OTHER INFORMATION: Reverse primer

<400> SEQUENCE: 4
atccccggga attgccatgt tatagtttag attttgcctg cgata                    45

<210> SEQ ID NO 5
<211> LENGTH: 38
<212> TYPE: DNA
<213> ORGANISM: Unknown
<220> FEATURE:
<223> OTHER INFORMATION: Cloning cassette

<400> SEQUENCE: 5
ggaattccag ctgaccacca tggcaattcc cggggatc                            38
```

POPULATION OF TRANSGENIC PLANTS INDIVIDUALLY COMPRISING DISTINCT CODOGENIC GENE SEGMENTS, THE POPULATION HAVING AT LEAST 50% OF THE CODOGENIC GENE SEGMENTS FROM A DONOR ORGANISM

RELATED APPLICATIONS

This application is a national stage application (under 35 U.S.C. 371) of PCT/EP2003/00922 filed Mar. 18, 2003, which claims benefit of German application 102 12 158.3 filed Mar. 19, 2002.

FIELD OF THE INVENTION

The present invention relates to populations of trangenic plants encompassing a substantial part of all codogenic gene segments of a donor organism, and to biological material derived therefrom, plasmid collections and populations of transformed host organisms with which plants can be transformed in a suitable manner. There are also described methods for generating the plants and the material, and the use of the plants and of the material for functional studies.

DESCRIPTION OF THE BACKGROUND

The rising world population and diminishing areas for cultivation mean that there is a need for sustainable production. Genomic information may be exploited in this context for the optimization of production processes, in partricular in chemistry, in the production of foodstuffs and in agriculture. Today, enormous amounts of genomic information are available. However, this predominantly takes the form of sequence information with indirect functional assignment, if any.

It has already been attempted to express individual genes from various organisms in plants for a variety of purposes. In these experiments, it was attempted to study the function of a particular gene in the plant and its effect on the physiology of the plant.

Approaches regarding the expression of a plurality of genes of a specific donor organism in a model plant have as yet only been limited to transient expression systems. Such an approach is described, for example, in WO 99/36516 and WO 01/07600, where a cDNA library derived from the donor organism is inserted into a suitable vector of a plant virus, whereby rapid and strong expression of the cDNA can be achieved after infecting the host plant with said vector. However, only those cDNAs which exist in the original library can be expressed in the plants, but significant amounts of the genes of a genome are expressed only very weakly or under highly specific conditions, if at all, and therefore not covered by such an approach. Another disadvantage of this procedure is that the infection causes effects. These effects may influence the results of physiological studies on the infected plants. Another weakness, which is likewise inherent in transient expression, is that the availability of the transfected material is only transient. Thus, the periods available for analytical studies are only relatively short, while developmental and prolonged effects are not identified. Moreover, when viral vectors are used, the size of the sequences which can be incorporated is limited owing to the fact that the sequences must be packaged in the viral coat.

SUMMARY OF THE INVENTION

It is an object of the present invention to provide plants which are suitable for systematically carrying out functional studies into the function of foreign genes over the entire developmental cycle of the plant and, if desired, even over more than one generation.

This object is achieved by the subject of the present invention, which is a population of transgenic plants comprising at least 50% of all codogenic gene segments of a donor organism, the codogenic gene segments being integrated in the gename of the plants.

BRIEF DESCRIPTION OF THE DRAWINGS

FIG. 1A-1D1 lists 5393 codogenic gene segments from *Saccharomyces cerevisiae*.

FIG. 2A-2N lists codogenic gene segments from *E. coli*.

DESCRIPTION OF THE INVENTION

The term "codogenic gene segment" refers to a nucleic acid. Nucleic acids are formed from monomers (nucleotides) and contain sugars, phosphate and either a purine or pyrimidine or their derivatives. They include DNA and RNA sequences which can be single- or double-stranded and can optionally contain synthetic, unnatural or modified nucleotide bases which can be incorporated into DNA or RNA.

In particular, the term "codogenic gene segment" refers to the coding sequence, i.e. the part of a gene which encodes a protein, polypeptide or part thereof.

The term "gene" refers to a DNA sequence which encompasses both the codogenic gene segment, that is to say in particular the coding sequence, and regulatory elements.

The structural gene which encompasses the codogenic gene segments can have a continuous coding sequence (open reading frame, abbreviated to ORF) or may contain one or more introns which are linked to the exons via suitable splice junctions.

The codogenic gene segments according to the invention are normally found in the cells of the donor organism. These sequences are therefore autologous with regard to the donor organism. In contrast, these codogenic gene segments are normally not found in the plants on which the populations according to the invention are based (recipient plant), unless donor organism and recipient plant are identical with regard to the codogenic gene segment. With regard to the recipient plant, these sequences are therefore heterologous or sequences which, while they can be found in the recipient plant, are derived from another individual. Accordingly, parts of the genome of the recipient plant can be homologous to or identical with a specific integrated codogenic gene segment.

What is critical for the present invention is the integration of the codogenic gene segments in the genome of the plants, where a specific codogenic gene segment can be integrated in the form of a continuous coding sequence (ORF) or may contain one or more introns. If this is the case, such sequences are, as a rule, spliced while being expressed by the plant, it being possible, but not imperative, that the splice pattern corresponds to that of the donor organism.

In principle, the codogenic gene segments can be integrated into the extranuclear genome, for example the plastid genome, of a plant. However, preferred in accordance with the invention is integration into the nuclear genome.

It is preferred in accordance with the invention stably to integrate sequences encompassing the heterologous codogenic gene segments into the genome of the plants. This entails one or more of the following aspects:

during the life cycle of a plant, the number of copies of a specific codogenic segment per cell is essentially constant;

the number of copies of a specific codogenic gene segment per cell can be determined;

being a trait of the plant, the codogenic gene segment is heritable and, in the case of nuclear integration, subject to Mendelian inheritance.

As a rule, the number of integrated copies of a specific codogenic gene segment per cell amounts to less than 20 and in most cases to less than 10. Preferred in accordance with the invention are plants with cells comprising approximately 1 to 5 copies and in particular 1 copy of a specific codogenic gene segment. The number of copies per cell can be determined in a manner known per se by "Southern blot" analysis (extraction of the genomic DNA, restriction digest, electrophoretic separation, transfer to membranes, hybridization with labeled DNA-specific probe or quantitative PCR).

In accordance with the invention, the life cycle of a plant advantageously comprises all of the developmental stages from germination to seed maturation. For example, the life cycle of *Arabidopsis thaliana* encompasses epigeal germination, the development of the seedling into a rosette, the development of the main shoot from the rosette, branching of the main shoot, the development of flowers on the shoots, the flowering process, and seed maturation. Under favorable conditions, *Arabidopsis thaliana* can be propagated seed to seed within approximately 6 weeks.

In accordance with a particular embodiment of the present invention, the heterologous codogenic gene segments in the genome of the transgenic plants are flanked unilaterally or, preferably, bilaterally, by T-DNA sequences, in particular by agrobacterial Ti plasmid sequences. This is likewise an aspect of the stable integration, according to the invention, of the codogenic gene segments into the genome of the plants.

Populations according to the invention of transgenic plants comprise at least 50% of all of the codogenic gene segments of a particular donor organism. Populations of transgenic plants with at least 70% and in particular with at least 90% of all of the codogenic gene segments of a specific donor organism are preferred.

In addition, the codogenic gene segments of a donor organism are generally characterized by the function of their expression products. These include, in particular, functions in the aspects metabolism, energy, transcription, protein synthesis, protein processing, cellular transport and transport mechanisms, cellular communication and signal transduction, cell rescue, cell defence and cell virulence, regulation of the cellular environment and interaction of the cell with its environment, cell fat, transposable elements, viral proteins and plasmid proteins, cellular organization control, subcellular localization, regulation of protein activity, proteins with binding function or cofactor requirement, and transport facilitation. Codogenic gene segments with the same function are combined to what are known as functional gene families.

Metabolic functions relate in particular to the amino acid metabolism, the nitrogen and sulfur metabolism, the nucleotide metabolism, the phosphate metabolism, the carbon and carbohydrate metabolism, the fat, fatty acid and isoprenoid metabolism, the metabolism of vitamins, cofactors and prosthetic groups, and the secondary metabolism.

Energetic functions relate in particular to glycolysis and glyconeogenesis, the pentose phosphate metabolism, the citric acid cycle, the electron transport and the membrane-associated energy storage, respiration, photosynthesis, fermentation, the metabolism of energy reserves, the glyoxylate cycle and fatty acid oxidation.

Functions regarding transcription affect mainly the transcription of rRNA-, tRNA and mRNA, RNA transport and transcript processing.

Functions regarding protein synthesis affect mainly ribosomal biogenesis, translation, translation control and aminoacyl-tRNA synthetases.

Functions regarding protein processing affect mainly folding and stabilization, targeting, sorting and translocation, and the modification of proteins, the assembly of protein complexes and the proteolytic degradation of proteins.

Functions regarding cellular transport and transport mechanisms affect mainly the nuclear, mitochondrial, vesicular, peroxysomal, vacuolar and extracellular transport, exocytossis and secretion, endocytosis, the cellular import and the cytoskeleton-dependent transport.

Functions regarding cellular communication and signal transduction affect mainly intracellular signaling and signal reception, and transmembrane signal transduction.

Functions regarding cell rescue, cell defence and cell virulence affect mainly stress response, detoxification and the degradation of foreign (exogenous) substances.

Functions regarding the regulation of the cellular environment and interaction of the cell with its environment affect mainly ionic homeostasis and cellular perception and response.

Functions regarding cell fate affect mainly the cell cycle and cell growth, cell morphogenesis, cell differentiation, cell death and cell senescence.

Functions regarding the cellular organization control affect mainly the cell wall, the plasma membrane, the cytoplasm, the cytoskeleton, the endoplasmic reticulum, the golgi apparatus, the plastids, the intracellular transport vesicles, the nucleus, the mitochondria, the peroxysomes, the endosomes and the vacuoles or lysosomes.

Functions regarding the subcelluloar localization affect in particular the cell wall, the plasma membrane, the cytoplasm, the cytoskeleton, the centrosomes, the endoplasmic reticulum, the golgi apparatus, intracellular transport vesicles, the nucleus, mitochondria, peroxysomes, endosomes, vacuoles or lysosomes, extracellular or secreted proteins, and prokaryotic cell membranes.

Functions regarding the regulation of the protein activity affect mainly the targets to be regulated.

Functions regarding proteins with binding function or cofactor requirement affect mainly protein binding and lipid binding.

Functions regarding transport facilitation affect mainly channel/pore type transporters, ion transporters, carbon and carbohydrate transporters, amino acid transporters, peptide transporters, lipid transporters, nucleotide transporters, allantoin and allantoate transporters, transporters of active substances, and transport mechanisms.

Particularly important in accordance with the invention are functions regarding metabolism and energy, in particular enzymes of the primary and secondary metabolism, for example P450 enzymes, regarding transcription, in particular transcription factors, and regarding cellular transport and transport mechanisms, in particular channels and transporters.

Thus, populations of transgenic plants which are preferred are in particular those which have at least one subpopulation comprising at least 55% and in particular at least 80% of all of the codogenic gene segments of a donor organism which can be assigned to a functional gene family.

As a rule, the codogenic gene segments of a specific donor organism are publicly available. Those which must be mentioned in particular are public gene databases such as the EMBL database (Stoesser G. et al., Nucleic Acids Res 2001, Vol. 29, 17-21), the GenBank database (Benson D. A. et al., Nucleic Acids Res 2000, Vol. 28,15-18), or the PIR database (Barker W. C. et al., Nucleic Acids Res. 1999, Vol. 27, 39-43).

Moreover, organism-specific gene databases can be used, for example the SGD database (Cherry J. M. et al., Nucleic Acids Res. 1998, Vol. 26, 73-80) or the MIPS database (Mewes H. W. et al., Nucleic Acids Res. 1999, Vol. 27, 44-48) for yeast, the GenProtEC database Riley M., Nucleic Acid Res. 1998, Vol. 26(1), 54) for *E. coli*, the TAIR database (Huala, E. et al., Nucleic Acids Res. 2001 Vol. 29(1), 102-5) or the MIPS database for *Arabidopsis*.

Using this database information, nucleic acids encompassing the codogenic gene segments can be obtained in a manner known per se from suitable sources and provided for the subsequent integration in the plant genomes.

The donor organisms include both prokaryotic and eukaryotic organisms such as viruses, bacteria, yeasts, fungi, algae, plants and animals.

If plants are chosen as donor organism, the plant can, in principle, have any phylogenetic relationship with the recipient plant. Thus, donor and recipient plants may belong to the same family, genus, species, variety or line, with increasing homology between the codogenic gene segments to be integrated and the corresponding parts of the genome of the recipient plant. Donor organisms which are preferred in accordance with the invention are microorganisms, in particular those whose genomes have been sequenced, for example *Acetobacter* (subgen. *Acetobacter*) *aceti*; *Acidithiobacillus ferrooxidans*; *Acinetobacter* sp.; *Actinobacillus* sp; *Aeromonas salmonicida*; *Agrobacterium tumefaciens*; *Aquifex aeolicus*; *Arcanobacterium Pyogenes*; Aster yellows phytoplasma; *Bacillus* sp.; *Bifidobacterium* sp.; *Borrelia burgdorferi*; *Brevibacterium linens*; *Brucella melitensis*; *Buchnera* sp.; *Butyrivibrio fibrisolvens*; *Campylobacter jejuni*; *Caulobacter crescentus*; *Chlamydia* sp.; *Chlamydophila* sp.; *Chlorobium limicola*; *Citrobacter rodentium*; *Clostridium* sp.; *Comamonas testosteroni*; *Corynebacterium* sp.; *Coxiella burnetii*; *Deinococcus radiodurans*; *Dichelobacter nodosus*; *Edwardsiella ictaluri*; *Enterobacter* sp.; *Erysipelothrix rhusiopathiae*; *Escherichia coli*; *Flavobacterium* sp.; *Francisella tularensis*; *Frankia* sp. Cpl1; *Fusobacterium nucleatum*; *Geobacillus stearothermophilus*; *Gluconobacter oxydans*; *Haemophilus* sp.; *Helicobacter pylori*; *Klebsiella pneumoniae*; *Lactobacillus* sp.; *Lactococcus lactis*; *Listeria* sp.; *Mannheimia haemolytica*; *Mesorhizobium loti*; *Methylophaga thalassica*; *Microcystis aeruginosa*; *Microscilla* sp. PRE1; *Moraxella* sp. TA144; *Mycobacterium* sp.; *Mycoplasma* sp.; *Neisseria* sp.; *Nitrosomonas* sp.; *Nostoc* sp. PCC 7120; *Novosphingobium aromaticivorans*; *Oenococcus oeni*; *Pantoea citrea*; *Pasteurella multocida*; *Pediococcus pentosaceus*; *Phormidium foveolarum*; *Phytoplasma* sp.; *Plectonema boryanum*; *Prevotella ruminicola*; *Propionibacterium* sp.; *Proteus vulgaris*; *Pseudomonas* sp.; *Ralstonia* sp.; *Rhizobium* sp.; *Rhodococcus equi*; *Rhodothermus marinus*; *Rickettsia* sp.; *Riemerella anatipestifer*; *Ruminococcus flavefaciens*; *Salmonella* sp.; *Selenomonas ruminantium*; *Serratia entomophila*; *Shigella* sp.; *Sinorhizobium meliloti*; *Staphylococcus* sp.; *Streptococcus* sp.; *Streptomyces* sp.; *Synechococcus* sp.; *Synechocystis* sp. PCC 6803; *Thermotoga maritima*; *Treponema* sp.; *Ureaplasma urealyticum*; *Vibrio cholerae*; *Vibrio parahaemolyticus*; *Xylella fastidiosa*; *Yersinia* sp.; *Zymomonas mobilis*.

In accordance with a particular embodiment of the present invention, the donor organism is a yeast, preferably of the genus *Saccharomyces*, in particular *Saccharomyces cerevisiae*.

Accordingly, a very particular embodiment of the present invention relates to populations of transgenic plants encompassing at least approximately 3000, preferably at least approximately 4500 and advantageously at least approximately 5500 codogenic gene segments from *Saccharomyces cerevisiae*, assuming that the approximate total of codogenic gene segments amounts to 6300 (Mewes et al., Nature 387 (Suppl) July 65, 1997). In particular, the codogenic gene segments are selected from among the codogenic gene segments shown in FIG. 1.

In accordance with a further particular embodiment, the donor organism is a bacterium of the genus *Escherichia*, preferably *E. coli*.

Accordingly, a further very particular embodiment of the present invention relates to populations of transgenic plants encompassing at least approximately 2000, preferably at least approximately 3000 and advantageously at least approximately 3500 codogenic gene segments from *E.coli*, assuming that the approximate total of codogenic gene segments amounts to 4300. In particular, the codogenic gene segments are selected from among the codogenic gene segments shown in FIG. 2.

Accordingly, populations according to the invention of transgenic plants are composed of several individual plants. These individual plants can be distinguished at least at the molecular level. Thus, for each codogenic gene segment from the totality of the codogenic gene segments of a particular donor organism which are encompassed by the population according to the invention of transgenic plants, there is at least one individual of the population with this codogenic gene segment. Accordingly, a population according to the invention of transgenic plants, which encompasses a particular number of a variety of codogenic gene segments of a donor organism, contains at least the same number of individual plants, of which each individual plant is characterized in that it contains a particular gene segment of said codogenic gene segment, while not containing the remaining said codogenic gene segments.

In addition, populations according to the invention can encompass at least one further individual plant in whose genome a specific codogenic gene segment of a donor organism is integrated in combination with a further codogenic gene segment or a plurality of further codogenic gene segments of the donor organism.

As a rule, the codogenic gene segments are linked operably with regulatory sequences in the genome of the plants. It is preferred within a population of transgenic plants to use analogous regulatory sequences for all of the heterologous codogenic gene segments.

As a rule, operable linkage of a specific codogenic gene segment with one or more regulatory sequences comprises a chemical fusion of two or more DNA fragments in suitable orientation, for example in sense or antisense orientation, so that a suitable reading frame is maintained or created by the fused sequences and expedient regulation of the expression of the DNA sequences in the plant cell is ensured.

The term "expression" refers to the transcription and/or translation of a codogenic gene segment. As a rule, the resulting product is a protein. However, expression also includes the transcription of a DNA which is inserted in antisense orientation relative to regulatory elements, thus creating an antisense mRNA. The products also include ribozymes. Expression can be systemic or local, for example limited to specific cell types, tissues or organs.

In principle, the regulatory sequences can take the form of sequences of the recipient plants according to the invention, sequences of the donor organism, sequences of a further organism or synthetic sequences, as long as the function of these sequences in the plants according to the invention is ensured.

As a rule, regulatory sequences are arranged upstream (5'), within and/or downstream (3') relative to a specific codogenic gene segment. In particular, they govern the transcription and/or translation and the transcript stability of the codogenic gene segment, if appropriate in conjunction with further homologous functional systems, such as the cellular protein biosynthesis apparatus.

Regulatory sequences include, above all, sequences arranged upstream (5'), which affect in particular the regulation of transcription initiation, such as promoters, and sequences arranged downstream (3'), which affect above all the regulation of transcription termination, such as polyadenylation signals.

Promoters predominantly govern the expression of the codogenic gene segment by acting as the attachment site for RNA polymerases and/or further factors required for an appropriate transcription initiation.

In principle, all promoters which are capable of stimulating the transcription of genes in plants can be employed. Suitable promoters which are functional in plants are generally known. They may be constitutive or inducible promoters. Suitable promoters may also be developmental- and/or tissue-specific, such as leaf-, root-, seed- and fruit-specific promoters.

Promoters which have proven particularly useful are promoters from phytopathogenic viruses and bacteria. Examples are the CaMV 35S promoter, the FMV 34S promoter, or a promoter from Cassava Vein Mosaic Virus (CsVMV), and, for example, a variety of promoters from *Agrobacterium tumefaciens*, such as the octopine synthase promoter (ocs), the nopaline synthase promotor (nos), or the mannopine synthase promoter. Moreover, a large number of plant promoters are available for the expression of genes in specific tissues, such as roots, flowers or stomata and above all seeds, such as, for example, the arc5 promoter from bean, the LeB4 promoter and the USP promoter from *Vicia faba* and the DcG3 promoter from carrot. A variety of promoters are also available above all for expression in seeds. Further seed-specific promoters are the sucrose binding protein promoter (WO 00/26388), the phaseolin promoter and the napin promoter. To express heterologous sequences strongly in as many tissues as possible, in particular also in leaves, it is preferred to use plant promoters of actin and ubiquitin genes, such as, for example, the rice Actin1 promoter besides various of the abovementioned viral and bacterial promoters. A further example of constitutive plant promoters are the sugar beet V-ATPase promoters (WO 01/14572). Examples of synthetic constitutive promoters which must be mentioned are the superpromoter (WO 95/14098) and promoters derived from G-boxes (WO 94/12015). Furthermore, chemically inducible promoters may also be employed under certain circumstances, compare EP-A 388186, EP-A 335528, WO 97/06268. Others which are available for the expression of genes in plants are leaf-specific promoters as described in DE-A 19644478 or light-regulated promoters such as, for example the petE promoter from pea.

Among the polyadenylation signals, the poly-A addition sequence form the *Agrobacterium tumefaciens* ocs or nos gene may be mentioned, in particular.

Further regulatory sequences which may be expedient also include sequences which govern the transport and/or the localization of the expression products (targeting). Sequences which must be mentioned in particular in this context are the signal-peptide- or transit-peptide-encoding sequences which are known per se. For example, the expression product can successfully be addressed to the plastids of a plant cell with the aid of plastid-transit-peptide-encoding sequences.

Plants which are preferred as recipient plants are in particular those which are capable of being transformed in an expedient manner. They include monocotyledonous and dicotelydonous plants. Plants which must be mentioned in particular are agriculturally useful plants such as cereals and grasses, for example *Triticum* spp., *Zea mais*, *Hordeum vulgare*, *Hafer*, *Secale cereale*, *Oryza sativa*, *Pennisetum glaucum*, *Sorghum bicolor*, *Triticale*, *Agrostis* spp., *Cenchrus ciliaris*, *Dactylis glomerata*, *Festuca arundinacea*, *Lolium* spp., *Medicago* spp. and *Saccharum* spp., pulses and oil crops, for example *Brassica juncea*, *Brassica napus*, *Glycine max*, *Arachis hypogaea*, *Gossypium hirsutum*, *Cicer arietinum*, *Helianthus annuus*, *Lens culinaris*, *Linum usitatissimum*, *Sinapis* alba, *Trifolium repens* and

*Vicia narbonensis*, vegetables and fruits, for example bananas, grapes, *Lycopersicon esculentum*, asparagus, cabbage, water melons, kiwi fruit, *Solanum tuberosum*, *Beta vulgaris*, cassava and chicory, trees, for example *Coffea* species, *Citrus* spp., *Eucalyptus* spp., *Picea* spp., *Pinus* spp. and *Populus* spp., medicinal plants and trees, and flowers.

In accordance with a particular embodiment, the present invention relates to transgenic plants of the genus *Arabidopsis*, for example *Arabidopsis thaliana* and the genus *Oryza*, for example *Oryza sativa*.

Especially preferred populations according to the invention of transgenic plants are based on a population of recipient plants which is essentially homogeneous. Accordingly, the essential distinguishing feature of individuals of this population is the integration of one or more codogenic gene segments of a donor organism. However, an in-planta transformation which has been carried out with one or more codogenic gene segments results, as a rule, in several transgenic plants which then, together with the respective direct progeny, form lines of one or more codogenic gene segments (multiline). A certain variability, which can essentially be attributed to differences in the transformation process, can result between two lines, i.e. individual transgenic plants and their progeny, in whose genome the same codogenic gene segment(s) of a donor organism are integrated. For example, differences between the lines with regard to integration sites and/or copy numbers may lead to quantitatively different expression of the codogenic gene segment(s).

In accordance with a particular embodiment, populations according to the invention encompass at least 5, at least 10 or at least 20 lines per codogenic gene segment.

In particular, it is preferred uniformly to choose regulatory sequences and further sequences due to the transformation process for different codogenic gene segments for a particular population of transgenic plants, so that differences within the population can essentially be contributed to the different codogenic gene segments.

Accordingly, transgenic plants according to the invention comprise at least one transgenic cell which encompasses one or more codogenic gene segments of a donor organism and is advantageously capable of expressing the same. Preferably, essentially all the cells of a transgenic plant according to the invention are transgenic.

The term "transgenic plants" which is used in accordance with the invention also refers to the progeny of a transgenic plant, for example the $T_1$, $T_2$, $T_3$ and subsequent plant generations, or the $BC_1$, $BC_2$, $BC_3$ and subsequent plant generations. Thus, the transgenic plants according to the invention can be raised and selfed or crossed with other individuals in order to obtain further transgenic plants according to the invention. Transgenic plants can also be obtained by means of vegetative propagation of transgenic plant cells.

The present invention also relates to transgenic plant material which can be derived from a population according to the invention of transgenic plants. Such material includes plant cells and specific tissues, organs and parts of plants in all their manifestations, such as seeds, leaves, anthers, fibers, roots, root hairs, stems, embryos, calli, cotyledons, petioles, crops, plant tissue, reproductive tissue and cell cultures which is derived from the actual transgenic plant and/or can be used for bringing about the transgenic plant. Also, such material encompasses at least 50% of all codogenic gene segments of the donor organism in question.

The present invention furthermore relates to a method for generating a population of transgenic plants in which
a) at least one codogenic gene segment of a donor organism is provided;
b) this codogenic gene segment, if appropriate in combination with a further codogenic gene segment or several further codogenic gene segments of the donor organism, is integrated into the genome of at least one plant; and
c) steps a) and b) are carried out for essentially all of the codogenic gene segments of the donor organism.

A codogenic gene segment can expediently be provided in a manner known per se, for example, by customary cloning. In particular, genomic DNA or mRNA can be amplified by means of cDNA of the donor organism. The first-mentioned procedure is the method of choice in the case of donor organisms whose genome has no introns. The last-mentioned procedure is expedient when the genome of the donor organism has introns and these introns are not to be integrated together with the codogenic gene segment in the genome of the plant. This gives a nucleic acid sequence containing the desired codogenic gene segment.

For further cloning, the sequence thus obtained, which contains the codogenic gene segment, is, as a rule, inserted into a suitable cloning vector. Suitable vectors are above all those which are capable of replication in suitable intermediate hosts such as bacterial host cells, for example *Bacillus, Streptomyces, Salmonella* and, above all *Escherichia coli*. The skilled worker is familiar with a multiplicity of suitable vectors and manipulations such as restriction, insertion, ligation, deletion and the like are also part of the expert knowledge, so that the desired sequence which contains the codogenic gene segment, if appropriate together with regulatory elements and/or further elements required for transformation and expression, is, as a rule, successfully provided.

In accordance with a preferred embodiment, a codogenic gene segment is provided by cloning it in a ligation-independent fashion. The advantage of this procedure is that the codogenic gene segments are neither cut by the earlier use of restriction endonucleases nor cloned in an undirected fashion via blunt ends or sticky ends, and the vector itself has no religation potential, a high cloning efficacy thus being achieved.

Particular procedures which can be followed for this purpose are
a1) to amplify the codogenic gene segment with random incorporation of an amount of thio-dNTPs;
a2) to allow a 3'-5'-exonuclease to act on the amplificate so that fragments with single-stranded ends are formed; and
a3) to incubate under annealing conditions the fragments resulting from step a2) with a vector whose single-stranded ends are at least in part complementary to the single-stranded ends of the fragments.

The amplification itself can be carried out in a manner known per se.

Preferably, a procedure is followed which matches the protocol for Pfu DNA polymerase or a Pfu/Taq DNA polymerase mixture.

The primers are chosen to match the sequence to be amplified.

The primers should expediently be chosen in such a way that the amplificate encompasses the entire codogenic sequence from the start codon to the stop codon. It is preferred to employ chimeras whose 5' ends are formed in each case by a universal adaptor sequence and whose 3' ends are formed in each case by a specific sequence of the codogenic gene segment. If the universal adaptor sequences for forward and reverse primers are different, directed cloning into the expression vector is possible.

Following the amplification, the amplificates are expediently analyzed. For example, separation by gel electrophoresis can be followed by qualitative and quantitative analysis.

If dNTPs are employed as a mixture with thio-dNTPs for the amplification, a ratio of 125:1 has proved advantageous, i.e., in theory, a thio-dNTP is incorporated instead of a dNTP at every $125^{th}$ position of the amplificate.

The incorporation of thio-dNTPs makes it possible to modify the amplificates with the aid of exonucleases. In particular, the amplified amplificates which, as a rule, have double-stranded ends, can be incubated with the enzyme exonuclease III. The enzyme has 3'-5'-exonuclease activity, so that the double-stranded DNA ends of the amplificates are degraded starting at the 3' end as a function of amplificate quantity, temperature, time and enzyme quantity. What remains is the counterstrand with the resistant 5' end. Since this enzyme is not capable of breaking down thio-dNTPs, the degradation stops at the first thionucleotide which has been incorporated. Owing to the incorporation of the thio-dNTPs, the amplificates are thus only subjected to limited degradation, independently of their size and DNA concentration.

Thereafter, the modified amplificates can be purified following a standard protocol (for example Qiagen). An aliquot of the purified amplificates is then available for the subsequent cloning, which, according to what has been said above, can be performed in particular in a ligation-independent fashion.

Suitable cloning vectors are generally known in expert circles. They include, in particular, vectors which are capable of replication in bacterial systems, i.e. above all vectors which ensure efficient cloning in *E. coli* and which make possible the stable transformation of plants. Those which must be mentioned in particular are various binary and co-integrated vector systems which are suitable for T-DNA-mediated transformation. As a rule, such vector systems are characterized in that they contain at least the vir genes required for *agrobacterium*-mediated transformation and the sequences which delimit the T-DNA (T-DNA border). These vector systems preferably also encompass further cis-regulatory regions such as promoters and terminators and/or selection markers by means of which suitably transformed organisms can be identified. While vir genes and T-DNA sequences are arranged on the same vector in co-integrated vector systems, binary systems are based on at least two vectors of which one harbors vir genes, but no T-DNA, while a second vector harbors T-DNA, but no vir gene. The last-mentioned vectors are therefore relatively small, easy to manipulate and capable of replication both in *E-coli* and in *agrobacterium*. These binary vectors include vectors from the series pBIB-HYG, pPZP, pBecks, pGreen. Vectors which are-preferably used in accordance with the invention are Bin19, pBI101, pBinAR, pGPTV and pCAMBIA. Binary vectors and their use are reviewed by Hellens et al, *Trends in Plant Science* (2000) 5, 446-451.

To prepare the vectors, the vectors can first be linearized with restriction endonuclease(s) and then enzymatically modified in a suitable manner. Another enzyme which is suitable for this purpose and which has 3'-5'-exonuclease activity is T4-DNA polymerase, which degrades the double-stranded DNA ends of the linearized vector into single strands as a function of vector quantity, temperature, time and enzyme quantity. The vector is subsequently purified, and in each case one aliquot is employed for the ligation-independent cloning.

For ligation-independent cloning, the enzymatically modified and, if appropriate, purified amplificates are cloned with similarly prepared vector fragments without the use of ligase. Instead of this enzyme, which is conventionally used, the annealing potential of the single-stranded ends of the modified amplificates and of the single-stranded ends of the vector, which have compatible adapter sequences, are exploited. This gives vectors which encompass the desired codogenic gene segment(s) (plasmid constructs).

The present invention therefore also relates to collections of plasmid constructs in which at least 50% of all of the codogenic gene segments of a donor organism are integrated. Here, specific plasmid constructs can have one or else more than one codogenic gene segments. The codogenic gene segments in these plasmid constructs are preferably operably linked with regulatory sequences. The regulatory sequences include, in particular, plant sequences like the above-described promoters and terminators. Advantageously, the plasmid constructs can stably be propagated in microorganisms, in particular *Escherichia coli* and *Agrobacterium tumefaciens*, under selective conditions, and make possible the transfer of heterologous DNA into plants.

In accordance with a particular embodiment, the plasmid constructs according to the invention are based on binary vectors (review of binary vectors in Hellens et al., 2000). As a rule, they contain prokaryotic regulatory sequences such as replication origin and selection markers for the propagation in microorganisms such as *Escherichia coli* and *Agrobacterium tumefaciens*, and agrobacterial T-DNA sequences to transfer DNA into plant genomes. At least the right border sequence, which encompasses approximately 25 base pairs, of the entire agrobacterial T-DNA sequence is required. The vector constructs according to the invention usually contain T-DNA sequences from both the right and the left border region, which contain expedient recognition sites for site-specifically acting enzymes which, in turn, are encoded by some of the vir genes.

The present invention moreover also relates to collections of host organisms which contain the collections according to the invention of plasmid constructs. In this sense, the host organisms are transformed with the plasmid constructs according to the invention. Suitable host organisms are known to the skilled worker. They include above all bacterial hosts of which some have already been mentioned above in context with donor microorganisms, for example bacteria from the genera *Bacillus Streptomyces, Salmonella*, and the like. Host organisms which are preferred in accordance with the invention are those from the genus *Escherichia*, in particular *Escherichia coli*, and *Agrobakterium*, in particular *Agrobacterium tumefaciens*.

Moreover, what has been said about the plant population also applies analogously to the collections according to the invention of plasmid constructs.

The resulting plasmid constructs can subsequently be transferred into a suitable intermediate host, for example a bacterium, for verification purposes. The transformation into *E. coli*, which can be carried out in a manner known per se, for example by means of heat shock or electroporation, has proved expedient in this context.

The transformed *E. coli* colonies can thus be analyzed for cloning efficacy. This can be carried out with the aid of a PCR. In such a procedure, both the identity and the integrity of the plasmid construct can be verified using a defined number of colonies by subjecting an aliquot of the colonies to said PCR. To do so, universal primers which are derived from vector sequences are generally employed, the forward primer being arranged upstream of the start ATG and the reverse primer downstream of the stop codon of the codogenic gene segment. The amplificates are separated by electrophoresis and assessed for quantity and quality. If a fragment with a suitable size is detected, the assessment is positive.

The plasmid constructs which have optionally been verified are subsequently used for transforming the plants. To this end, it may first be necessary to obtain the constructs from the intermediate hosts. For example, the constructs can be obtained from bacterial hosts in the form of plasmids using a procedure analogous to conventional plasmid isolation.

A large number of methods for transforming plants are known. Since stable integration of heterologous DNA into the genome of plants is advantageous according to the invention, T-DNA-mediated transformation in particular has proved to be expedient.

To do so, it is first necessary to transform suitable vehicles, in particular agrobacteria, with the codogenic gene segment or the corresponding plasmid construct. This can be done in a manner known per se. For example, the plasmid construct which has been generated according to what has been said above can be transformed into competent agrobacteria by means of electroporation or heat shock.

In principle, one must distinguish between the formation of co-integrated vectors and the transformation with binary vectors. In the first alternative, the vector constructs encompassing the codogenic gene segment have no T-DNA sequences, but the co-integrated vectors are formed in the agrobacteria by homologous recombination of the vector construct with T-DNA. The T-DNA is present in the agrobacteria in the form of Ti or Ri plasmids in which the oncogenes have expediently been replaced by exogenous DNA. If binary vectors are used, they can be transferred to agrobacteria by bacterial conjugation or directly. These agrobacteria expediently already comprise the vector which harbors the vir genes (frequently referred to as helper-Ti(Ri) plasmid).

One or more markers with the aid of which the transformed agrobacteria and transformed plant cells can be selected may also advantageously be used together with the plasmid construct and the T-DNA. A multiplicity of markers have been developed for this purpose. They include for example those which confer resistance to chloramphenicol, kanamycin, the aminoglycoside G418, hygromycin and the like.

If desired, the plasmid constructs can be verified again with regard to identity and/or integrity before they are transformed into agrobacteria. This can be done for example in analogy to the above PCR for verifying the cloning efficacy.

As a rule, it is desired that the plasmid constructs are flanked by T-DNA unilaterally or bilaterally of the codogenic gene segment. This is particularly useful when the bacteria used for the transformation belong to the species *Agrobacterium tumefaciens* or *Agrobacterium rhizogenes*.

Preferred in accordance with the invention is the transformation with the aid of *Agrobacterium tumefaciens*.

The transformed agrobacteria can be cultured in a manner known per se and are thus available for expedient plant transformation.

The plants or plant parts to be transformed are grown or provided in the customary manner. The transformed agrobacteria are subsequently allowed to act on the plants or plant parts until a sufficiently high transformation rate has been achieved.

The agrobacteria can act on the plants or plant parts in different ways.

For example, a culture of morphogenic plant cells or tissue can be used. Subsequently to the T-DNA transfer, the bacteria are eliminated, as a rule by using antibiotics, and the regeneration of plant tissue is induced. This is done in particular using plant hormones so that, after callus has formed initially, the development of shoots is promoted.

It is preferred in accordance with the invention to carry out the transformation in planta. To this end, it is possible, for example, to allow the agrobacteria to act on seeds of plants or to inoculate plant meristem with agrobacteria.

In particular it has proved advantageous according to the invention to allow a suspension of transformed agrobacteria to act on the intact plant or at least the flower primordia. The plant is subsequently grown on until seeds of the treated plant are obtained (Clough and Bent, Plant J. (1998) 16, 735-743).

To select transformed plants, plant material obtained from the transformation process is, as a rule, subjected to selective conditions so that transformed plants can be distinguished from untransformed plants. For example, the seeds which have been obtained in the above-described manner can again be planted and, after cultivation, be subjected to suitable selection by spraying. Another possibility is to sterilize the seeds, if appropriate, and then to grow them on agar plates using a suitable selection agent such that only the transformed seeds can grow into plants.

The present invention also relates to the use of a population according to the invention of transgenic plants and/or a biological material derived therefrom for functional studies.

In accordance with an embodiment, the functional studies concern the metabolism of the transgenic plants. Thus, it is possible to study in particular biochemical parameters, such as the accumulation of specific substrates or products of enzymatic reactions or the expression of endogenous genes of the recipient plant, for example, with the aid of the RNA or protein profile of the plant.

In accordance with a further embodiment, the functional studies concern phenotypic traits of the transgenic plants. Phenotypic traits of interest include, for example, the growth, the color, the morphology or the flowering behavior of the plants and further traits which characterize the phenotype of the plant. Such studies can be carried out by assessing individual cells of the transgenic plant. As a rule, however, such studies are carried out at the multicellular level by assessing organized structures, i.e. in particular the intact plant or plant parts such as leaves, roots and the like. The studies can therefore take the form of macroscopic or microscopic studies.

In accordance with a particular embodiment, at least one trait selected from among germination behavior, number of cotyledons, cotyledon area, number of rosette leaves, rosette leaf area, number of stomata on the rosette leaves, shape of the rosette leaves, dry weight of the rosette leaves, plant growth rate, time of shoot formation, branching of the shoot, shoot length, number of lateral shoots, number of flowers, flower size, flowering time, inflorescence shape, pollen size, color and number of pollen, seed size, seed color, seed shape, relative seed weight (based on seed volume) and absolute seed weight, total number of seeds, number of seeds per pod, pod length, number of pods per plant, time of seed maturation, root length, total root weight, root branching, number and length of root hairs, onset of senescence, duration of senescence and plant pigmentation (chlorophyll content) is studied.

In accordance with a particular aspect of the present invention, the functional studies are carried out on plants which are exposed to particular environmental conditions. These include abiotic stresses such as low-temperature stress, frost stress, drought stress, salt stress, ozone stress, $CO_2$ stress, light stress, oxidative stress, high-temperature stress, anoxic stress, heavy metals, ionizing/UV radiation, nutrient deficiency (for example N, P, K, microelements and the like), biotic stresses such as plant pathogens, for example fungi, plasmodia, bacteria and viruses, plant pathogens such as nematodes, protozoans, slugs, snails and insects, furthermore higher parasitic plants, and biological interactions such as symbioses.

The functional determination of the donor organism's codogenic gene segments in the recipient is of particular importance. This application applies both to codogenic gene segments whose function in the donor organism is known and to codogenic gene segments whose function in the donor organism is insufficiently elucidated, if at all. In this context, the function may already be exerted by the transcribed RNA, for example in the sense of antisense suppression or cosuppression, or by a regulatory RNA. In most cases, however, the function relates to the translated protein.

The functional determination can be carried out for example based on the above-described metabolic or phenotypic modifications.

As a rule, the use according to the invention for carrying out functional studies includes a method in which
a) the population according to the invention of transgenic plants is provided;
b) the desired functional study is carried out; and
c) the result of the study is compared with a result of a study obtained analogously with at least one reference plant.

The reference plant is characterized in that none of the codogenic gene segments encompassed by the population according to the invention is integrated into its genome or is at least not expressed therein. In this sense, the reference plant is to be referred to as the wild type from which the transgenic plants of the population according to the invention differ by the integration and in particular the expression of at least one codogenic gene segment.

If the comparison reveals a deviation, it can be concluded that the recipient plant has been the subject of a functional modification which correlates with the expression of one or more specific codogenic gene segments of a donor organism.

EXAMPLES

The present invention is hereinbelow described in greater detail with reference to examples.

Example 1

Generation of the Population of Transgenic Plants

The generation of a population according to the invention of transgenic plants is described with reference to *Arabidopsis thaliana* into whose genome the codogenic gene segments from *Saccharomyces cerevisiae* are integrated. By way of example, specific information is given for the YKL174C gene and the YKR009C gene. As a rule, the remaining codogenic gene segments are integrated analogously or, if necessary, in suitably modified form.

1. Generation of Transformed Agrobacteria

To generate the population according to the invention of transgenic plants, the codogenic gene segments to be integrated are initially transferred to agrobacteria. The process chain used for this purpose, which encompasses eight steps, permits efficaceous amplification and directed cloning of the amplificates into constitutive expression vectors with plant selection markers and their transformation into agrobacteria of a high-throughput process.

The process chain is divided into the following eight process steps: amplification (1), modification of the amplificate (2), vector preparation (3), ligation-independent cloning (4), transformation of *E.coli* (5), PCR for verifying the cloning efficacy (6), plasmid preparation (7) and transformation of agrobacteria (8). Unless otherwise specified, standard methods of Sambrook et al., *Molecular Cloning: A laboratory manual*, Cold Spring Harbor 1989, Cold Spring Harbor Laboratory Press are used.

1.1. Amplification

The amplification is carried out in a 96-well thermoplate in accordance with the Pfu Turbo or Herculase DNA polymerase protocol (Stratagene). The composition is as follows: 1× PCR buffer [20 mM Tris-HCl (pH 8.8), 2 mM $MgSO_4$, 10 mM KCl, 10 mM $(NH_4)SO_4$, 0.1% Triton X-100, 0.1 mg/ml BSA], 0.2 mM α-Thio-dNTP and dNTP (1:125), 100 ng genomic DNA of *Saccharomyces cerevisiae* (strain S288C; Research Genetics, Inc., now Invitrogen), 50 pmol forward primer, 50 pmol reverse primer, 2.5 U Pfu or Herculase DNA polymerase. The amplification cycles are as follows: 1 cycle for 3 min at 94° C., followed by 25-30 cycles of in each case 30 sec at 94° C., 30 sec at 55° C. and 5-6 min at 72° C., followed by 1 cycle of 7-10 min at 72° C., then 4° C.∞. The amplification products are separated electrophoretically and assessed with regard to quantity and quality. If a fragment in the correct size is detected, the assessment is positive.

The following primer sequences are selected:
For the YKL174C gene:

```
1) forward primer
                                          (SEQ ID NO: 1)
5'-GGAATTCCAGCTGACCACCATGCCAGAGTATACGCTACTGGC 2) reverse primer
                                          (SEQ ID NO: 2)
5'-ATCCCCGGGAATTGCCATGTCATATATCATATCTACGATCATGG
```

For the YKR009C gene:

```
1) forward primer
                                          (SEQ ID NO: 3)
5'-GGAATTCCAGCTGACCACCATGCCTGGAAATTTATCCTTCAAAG 2) reverse primer
                                          (SEQ ID NO: 4)
5'-ATCCCCGGGAATTGCCATGTTATAGTTTAGATTTTGCCTGCGATA
```

1.2. Modification of the Amplificate

Treatment with exonuclease III is effected in the same 96-well thermoplate as the amplification reaction above, by adding 10 U exonuclease III (MBI-Fermentas). The reactions are incubated for 10 minutes at 20° C. in a cycler and stopped by addition of high-salt buffer from the Qiaquick Purification Kit (Qiagen). The purification is performed as specified in the Qiaquick standard protocol (Qiagen).

1.3. Vector Preparation

The restriction with NcoI and its inhibition is carried out using 30 μg of vector DNA following the NcoI protocol (MBI-Fermentas). A binary vector which, between the T-DNA border sequences, comprises a selection cassette (promoter, selection marker, terminator) and an expression cassette with promoter, cloning cassette and terminator sequence is used. The binary vector has no further NcoI cleavage sites except for the one in the cloning cassette. The cloning cassette consists of the following sequence:
5'-GGAATTCCAGCTGACCACCATGGCAAT-TCCCGGGGATC-3' (SEQ ID NO: 5). The nuclease reaction is treated with 1 U T4-DNA polymerase and then incubated for 2 min at 37° C. and stopped by addition of high-salt buffer. The linearized and modified vector fragments are purified via NUCLEOBOND nucleic acid purification columns following the standard protocol (Machery-Nagel).

1.4. Ligation-Independent Cloning

Approx. 30 ng of prepared vector (as per 1.3.) and a defined amount of modified amplificate (approx. 80 ng, as per 1.2) are mixed in a 96-well thermoplate.

Annealing is performed in the cycler as follows: 1 cycle for 15 min at 65° C., cooling to 37° C. (0.1° C./1 sec), 1 cycle for 10 min at 37° C., cooling to 4° C. (0.1° C./1 sec), then 4° C. ∞.

1.5. Transformation of *Escherichia coli*

The transformation is carried out in the same 96-well thermoplate as the ligation-independent cloning above by adding competent *E. coli* cells (strain DH5α) and incubation in the cycler for 20 min at 1° C., followed by a heat shock for 90 seconds at 42° C and cooling to 4° C. This is followed by the addition of complete medium (SOC) and transfer into a 96-well deepwell plate with incubation for 45 min at 37° C. The entire reaction is subsequently plated onto agar plates supplemented with kanamycin and incubated overnight at 37° C.

1.6. PCR for Verifying the Cloning Efficacy

The amplification is carried out in a 96-well thermoplate following the protocol for Taq DNA polymerase (Gibco-BRL). The composition is as follows: 1× PCR buffer [20 mM Tris-HCL (pH 8.4), 1.5 mM $MgCl_2$, 50 mM KCl, 0.2 mM dNTP, 5 pmol forward primer, 5 pmol reverse primer, 0.625 U Taq DNA polymerase. A defined number of plasmid constructs is picked from each agar plate, and in each case one aliquot is transferred into one well, charged with the PCR mastermix, of a 96-well thermoplate. The amplification cycles are as follows: 1 cycle for 5 min at 94° C., followed by 35 cycles with in each case 15 sec at 94° C., 15 sec at 66° C. and 5 min at 72° C., followed by 1 cycle for 10 min at 72° C., then 4° C. ∞.

As a rule, four different colonies are analyzed per codogenic plasmid construct. To this end, the colonies in question are taken up with a tip of a pipette and transferred into the solution for the PCR.

Control primers which bind upstream and downstream of the cloning cassettes and thus make possible the amplification of the insert are used.

The amplification products are separated electrophoretically and assessed for quality. If a PCR fragment with the respective size is detected, the assessment is positive. It is always the colony of the first positive PCR fragment from each group of four colonies which is taken into the subsequent plasmid preparation step.

1.7. Plasmid Preparation

An aliquot of positive colonies is transferred into a well, charged with complete medium (LB) and kanamycin, of a deepwell plate and incubated overnight at 37° C.

The plasmid preparation is carried out as specified in the QIAPREP nucleic acid purification column standard protocol (Qiagen).

1.8. Transformation of Agrobacteria 1 ng of the isolated plasmid DNA is transformed into competent *Agrobacterium tumefaciens* cells strain GV 3101 pMP90 (Koncz and Schell, Mol. Gen. Gent. 204, 383-396, 1986) in a 96-well thermoplate by means of electroporation. Then, complete medium (YEP) is added and the reaction is transferred into a 96-well deepwell plate with incubation for 3 hours at 28° C. Thereafter, the entire reaction is plated onto YEP agar plates with kanamycin and incubated for 48 hours at 28° C.

2. Plant Transformation and Selection

The plasmid constructs present in the agrobacteria generated as specified in 1, are then available for transforming plants.

2.1. Bacterial Culture

With the aid of a pipette tip, one colony is picked from the agar plate and taken up in 3 ml of liquid TB medium which additionally contains kanamycin, rifampicin and gentamycin. The preculture grows for 48 hours at 28° C. and 120 rpm.

400 ml of LB medium which likewise contains kanamycin and gentamycin are used for the main culture. The preculture is transferred into the main culture. The main culture grows for 18 hours at 28° C. aund 120 rpm. Following centrifugation at 4000 rpm, the pellet is resuspended in infiltration medium (MS medium, 10% sucrose).

2.2. Plant Culture

Dishes (green Piki Saat 80 dishes with perforated bottom, 30×20×4.5 cm, Wiesauplast, Kunststofftechnik, Germany) are half-filled with a GS 90 substrate (standard soil, Werkverband E.V., Germany). The dishes are watered overnight with 0.05% PREVICUR solution (PREVICUR N, fungicide against mildew, Aventis CropScience). *Arabidopsis thaliana* C24 seeds are broadcast over the dish, approximately 1000 seeds per dish. The dishes are covered with a hood and placed into the stratification chamber (8 h, 110 µE, 22° C.; 16 hours in the dark at 6° C.). After 5 days, the dishes are placed into the short-day phytotron (8 h 130 µE, 22° C.; 16 hours in the dark at 20° C.). Here, they remain for approximately 10 days until the first true leaves have formed.

The seedlings are transferred into pots containing the same substrate (Teku pots, 10 cmØ, series LC, manufacturer: Poppelmann GmbH&Co, Germany). Nine plants are pricked out into each pot. The pots are then returned into the short-day phytotron, where the plants continue to grow.

After 10 days, the plants are transferred into the greenhouse cabin (additional illumination, 16 h, 340 µE, 22° C.; 8 h in the dark at 20° C.), where they continue to grow for another 17 days.

2.3. Transformation 6-week-old *Arabidopsis* plants which are just flowering are dipped for 10 seconds in the above-described agrobacterial suspension. The suspension had previously been treated with 10 µl of SILWETT L77 surfactant (Crompton S.A., Osi Specialties, Switzerland). The respective method is described by Clough and Bent, 1998.

The plants are then laid flat into a humid chamber for 18 hours. Thereafter, the pots are returned to the greenhouse, where the plants continue to grow. The plants remain for another 10 weeks in the greenhouse until the seeds can be harvested.

2.4. Selection

Depending on the resistance marker used for the selection of transformed plants, the harvested seeds are planted in the greenhouse and subjected to spray selection, or else sterilized and then grown on agar plates with the respective selection agent. After approx. 10-14 days, the transformed resistant plants differ markedly from the dead wild-type seedlings and can be pricked out into 6-cm pots. To carry out the selection in the greenhouse, seedlings are stratified for 3 days and then sprayed with an aqueous solution of 4 mg/l Pursuit. This selection is repeated after 3 days and 5 days. After a further 2 days, the transformed, resistant seedlings (plantlets in the four-leaf stage) can be distinguished clearly from the untransformed plantlets. The nontransgenic seedlings are bleached or dead. The transformed resistant plants are pricked out into 6-cm pots, where they are grown and their seeds are obtained. The seeds of the transgenic *A. thaliana* plants are stored in the freezer (at −20° C.).

In this manner, a population of transgenic plants, or biological material derived therefrom, of the species *Arabidopsis thaliana* in whose genome in each case one codogenic gene segment from *Saccharomyces cerevisiae* is integrated is generated.

This population is subjected to functional studies. The phenotypic study under normal conditions and stress conditions is used as an example.

3. Description of the Morphological Analyses.

3.1. Preparation of the Plant Material

The seeds are planted in plastic pots with a diameter of 60 mm. For the soil mixture, a mixture of GS-90 substrate and quartz sand (4:1 v/v) is mixed in the potting machine and filled into the pots. Thereafter, 35 pots are placed together into a dish and treated with PREVICUR. To carry out treatment, 25 ml of PREVICUR are taken up in 10 l of tap water. This quantity was sufficient for treating approximately 200 pots. The pots are placed into the PREVICUR solution and additionally provided with overhead irrigation with tap water without PREVICUR. The seeds are planted on the same day.

For planting, the seeds which are stored in the freezer (at −20 ° C.) are removed from the reaction vessels with the aid of a toothpick and transferred into the pots which contain the soil mixture. In total, approximately 5-12 seeds are distributed in the middle of the pot.

After planting, the dishes together with the pots are covered with a matching plastic hood and placed into the growth cabinet at 16 h light (20° C.) and for 3-4 days in the dark (4° C.). The humidity level is approximately 80-90%. After the stratification, the test plants are grown for 21 days in a 16 h light/8 h dark photoperiod at 20° C. and an atmospheric humidity of 60%. OSRAM tubes type VIALOX high-pressure sodium fluorescence tube (manufactured by Osram, Germany), which generate light with the color SON-T PLUS at an intensity of 220 µE/m2/s were used as the light source.

After the stratification, the 10-day-old seedlings are singled out. The plants which show the best growth in the middle of the pot are considered the target plants. All the remaining plants are carefully removed with the aid of metal tweezers and discarded.

During their growth, the plants are irrigated twice overhead with tap water (directed at the soil).

3.2. Morphological Analysis

The 21-day-old test plants are assessed using a developmental key. All the morphological deviations from the reference plant (non-genetically-modified wild type) are recorded. The developmental key groups all of the morphological deviations of the Arabidopsis plants into six main groups. Pigment mutants, cabbage head mutants, dwarf mutants, foliar mutants, rosette mutants and flowering mutants are distinguished. In the main group in question, between two and five different phenotypes are recorded. Thus, for example, albino/yellow mutants, fusca mutants and dark-green mutants are distinguished in the main group of the pigment mutants. In addition to the main traits, other traits such as shape of the leaves, the degree of hirsuitness of the leaves, plant size and flowering time are recorded in the main group in question.

With the aid of the developmental key, a plurality of lines in which a marked morphological deviation to the phenotype of the wild type is observed are detected within the population.

Thus, early flowering is observed in lines (2510) which express the YKL174C gene (similarity to choline transport protein HNM1P). These transgenic plants already flower at an age of 25 days. In contrast, the non-transgenic wild-type plants flower at an age of as much as 30 days or more under identical growth conditions. In addition to the phenomenon of early flowering, other morphological traits such as dark-green pigmentation and dwarfism can be identified with the aid of the key.

In lines which express the YKR009C gene (hydratase-dehydrogenase-epimerase, peroxisomal), dwarfism is observed on day 21 post-germination. The rosette diameter of the transgenic plants measures approximately 15 mm, while the rosette diameter of a wild type of equal age measures approximately 40 mm. Also, pigmentation is markedly darker, which can be attributed to an increased chlorophyll content.

Phenotypic modifications are also observed in further lines which express specific, other codogenic gene segments, while no phenotypic modifications in the transgenic plants were observed for the expression of the remaining codogenic gene segments in the present model.

3.3. Drought Stress Analysis

After the morphological traits were studied, the test plants were exposed to the drought stress test. To ensure identical drought stress conditions for all of the test plants, the test plants are watered generously before being exposed to the drought stress. This measure is intended to ensure as much homogeneity as possible with regard to the moisture content at the beginning of the test. To minimize light damage, the light intensity is reduced to approximately $150\ \mu Em^{-2}s^{-1}$ during the test. The relative atmospheric humidity is reduced from 60% to 20% at 20° C. The relative atmospheric humidity is reduced stepwise by 10% per day. To rule out positional effects, the trays holding the test plants are rotated in the chamber over the entire test period.

The plants which display sensitivity to the stressor (which are sensitive in comparison with the wild type) are recorded on days 7, 8 and 9 after the onset of the stress. The old leaves of the drought-sensitive plant show yellowish or pale green discoloration and, having wilted, lie on the ground. The younger leaves, in contrast, are curled and resemble the healthy leaves in color. The size of the drought-sensitive plants, in contrast, corresponds approximately to that of the wild type. On day 9 after the onset of the stress, the drought-sensitive plants are desiccated and brittle.

Plants which show drought resistance in comparison with wild-type reference plants are observed daily between days 11 and 14 after the onset of the stress. The observations are recorded. The phenotype of the drought-resistant plants does not differ from the phenotype of a non-stressed plant. The wild-type plants, in contrast, are desiccated after day 10.

Thus, the expression of specific codogenic gene segments from *Saccharomyces cerevisiae* (in particular the ORFs YDR51w and YER174c encoding glutaredoxin and thioredoxin) leads to improved drought resistance in *Arabidopsis thaliana* in comparison with the wild type, while the expression of the remaining codogenic gene segments has no effect on drought resistance.

3.4. Frost Stress Analysis.

To carry out the frost stress analysis, the test plants are raised as described above. At the age of 21 days, they are exposed to the frost stress test. The light intensity during the test is reduced to approximately $50\ \mu Em^{-2}s^{-1}$ in order to avoid light damage during the stress test. The relative atmospheric humidity is not modified during the test. The frost stress treatment is carried out at the following temperatures: first 10 hours at −2° C. and subsequently 48 hours at −6° C. The transition from 20° C. to −2° C., from −2° C. to −6° C. and from −6° C. to 20° C. takes in each case 4 hours. These stress conditions are sufficient to kill the wild-type plants. 3 days after the frost stress test has ended, the test plants are analyzed for the presence of resistance reactions.

In the frost-resistant lines, it is observed that growth continues for 3 days after the stress has ended. Only occasional frost damage, if any, is observed. In most cases, this is limited to the oldest leaves. Frost damage is characterized by desiccation and discoloration of the damaged parts, in particular the leaves. The discolored leaves are pale green or yellow.

Thus, the expression specific codogenic gene segments from *Saccharomyces cerevisiae* leads to improved frost resistance in *Arabidopsis thaliana* in comparison with the wild type, while the expression of the remaining codogenic gene segments has no effect on frost resistance.

4. Plant Cultivation for Bioanalytical Studies.

The bioanalytical study of the plants requires that the plants are grown rapidly and uniformly.

For the soil mixture, a mixture of GS-90 substrate and quartz sand (4:1 v/v) is mixed in the potting machine (Laible System GmbH, Singen, Germany) and filled into the pots. Thereafter, 35 pots are placed together into a dish and treated with PREVICUR. To carry out treatment, 25 ml of PREVICUR are taken up in 10 l of tap water. This quantity was sufficient for treating approximately 200 pots. The pots are placed into the PREVICUR solution and additionally provided with overhead irrigation with tap water without PREVICUR. The seeds are planted on the same day.

For planting, the seeds which are stored in the freezer (at −20° C.) are removed from the Eppendorf tubes with the aid of a toothpick and transferred into the pots which contain the soil mixture. In total, approximately 5-12 seeds are distributed in the middle of the pot.

After planting, the dishes together with the pots are covered with a matching plastic hood and placed into the growth cabinet at 16 h light (20° C.) and 8 hours darkness at 4° C. The humidity is approximately 80-90% and the time of the treatment is 72 hours. After the stratification, the test plants are cultivated for 21 days at a 16-hour-light/8-hour-dark photoperiod at 20° C., an atmospheric humidity of 60% and a CO2 concentration of 400 ppm. OSRAM daylight lamps type POWERSTAR HQI-T 250 W/D, which generate a light resembling the solar spectrum at a light intensity of 220 μE/m2/s are used as the light source.

After the stratification, the 10-day-old seedlings are singled out. The plants which show the best growth in the middle of the pot are considered the target plants. All the remaining plants are carefully removed with the aid of metal tweezers and discarded.

During their growth, the plants are subjected twice daily to overhead irrigation with tap water (directed at the plants/pots). After approximately 22 days, the plants, which weigh approximately 300-400 mg, are harvested for the analysis.

5. Metabolic Analysis

The plant material is harvested rapidly and shock-frozen in liquid nitrogen, freeze-dried and then extracted by means of accelerated solvent extraction (ASE) using methanol/water and methanol/dichloromethane. Following liquid-liquid-partition, aliquots of the organic phase and the aqueous phase are evaporated to dryness. In the case of the organic phase, the derivatization comprises transmethylation followed by methoxyamination by reaction with methoxyamine hydrochloride and trimethylsilylation with MSTFA (N-methyl-N-(trimethylsilyl)-trifluoroacetamide). The methanolic/aqueous phase is derivatized only by means of methoxyamination and trimethylsilylation. Final determination of the analytes is carried out by GC/EI-MS. To carry out an LC-MS/MS, the extracts, which have been evaporated to dryness, are only taken up in mobile phase and then analyzed.

In this way the plant material can be investigated, for example, for the amount therein of the amino acids methionine and threonine. For this purpose the methionine content and threonine content are determined by liquid and gas chromatography (LC and GC) for each transgenic plant in the above-described population (Arabidopsis thaliana with codogenic gene segments from Saccharomyces cerevisiae) in each case on 15 transgenic lines and on further plant samples, serving for comparison, from wild-type plants (Arabidopsis thaliana).

The chromatograms are evaluated by dividing the measured peak areas or peak heights of the analyte under determination (methionine or threonine) by the peak area or peak height of the respective internal standard. These values are standardized to the fresh weight determined for the plant. The value for each transgenic plant is then related to the respective wild-type control group, by dividing it by the mean of the 5 values obtained for the wild-type plants in question (factor 1).

Additionally, the value for a transgenic plant with a defined ORF is related to the mean of the values of all other 14 transgenic plants in whose genome the ORF has not been integrated, and the values of the 5 wild-type controls (factor 2).

The table below lists these values from two experiments, conducted independently of one another, for the plants in whose genome the YEL046C ORF from Saccharomyces cerevisiae has been integrated.

| Analyte | Factor 1 | Factor 2 | GC/LC |
|---|---|---|---|
| Methionine | 3.46-3.58 | 3.31-3.4 | LC |
| Threonine | 0.45-0.15 | 0.61-0.15 | LC |
| Threonine | 0.17-0.16 | 0.18-0.16 | GC |
| Methionine | 3.31-3.67 | 3.5-3.53 | GC |

Accordingly, those transgenic plants in whose genome the YEL046C ORF, encoding threonine aldolase, has been integrated, exhibit a significantly increased methionine content and a significantly decreased threonine content. This applies not only to the comparison with wild-type plants (factor 1) but also to the comparison with the other transgenic plants in the population investigated, in whose genome the said ORF has not been integrated (factor 2).

We claim:

1. A population of transgenic plants that consists of a plurality of transgenic plants of which each plant has integrated into its genome one or more than one copy of one codogenic gene segment of a cellular donor organism that encodes one protein of the cellular donor organism, but has integrated no other codogenic gene segment encoding another protein of the cellular donor organism,
   wherein the integrated codogenic gene segment comprises a start codon and a stop codon that define an open reading frame encoding the protein;
   wherein the integrated codogenic gene segment is operably linked to a regulatory sequence so that the open reading frame is transcribed and translated;
   wherein said plurality of transgenic plants as a whole comprises at least 50% of all codogenic gene segments that encode a protein of the cellular donor organism; and
   wherein the plurality of transgenic plants is obtained by
   a) providing a known codogenic gene segment that encodes one protein of a cellular donor organism and integrating one or more than one copy of the codogenic gene segment into the genome of a plant;
   b) providing another known codogenic gene segment that encodes another protein of the cellular donor organism and integrating one or more than one copy of the other codogenic gene segment into the genome of another plant;
   c) repeating step b) so that the resulting plurality of transgenic plants as a whole comprises at least 50% of all codogenic gene segments that encode a protein of the cellular donor organism.

2. The population of claim 1, wherein the codogenic gene segments are integrated into the nuclear genome.

3. The population of claim 1, wherein 1 to 5 copies of the codogenic gene segments are integrated per plant cell.

4. The population of claim 1, wherein the codogenic gene segments are unilaterally or bilaterally flanked by a T-DNA sequence.

5. The population of claim 1, wherein the regulatory sequence contains a signal peptide-encoding sequence, transit-peptide-encoding sequence, or both.

6. The population of claim 1, wherein the cellular donor organism is a microorganism.

7. The population of claim 6, wherein the microorganism is a yeast.

8. The population of claim 7, wherein the yeast is *Saccharomyces cerevisiae*.

9. The population of claim 6, wherein the microorganism is an organism of the species *Escherichia coli*.

10. The population of claim 1, wherein the transgenic plants belong to the genus *Arabidopsis*.

11. The population of claim 1, wherein the transgenic plants belong to the genus *Oryza*.

12. The population of claim 1, wherein the product of the codogenic gene segments has a function in metabolism, energy, transcription, protein synthesis, protein processing, cellular transport and transport mechanisms, cellular communication and signal transduction, cell rescue, cell defense and cell virulence, regulation of the cellular environment and interaction of the cell with its environment, cell fat, transposable elements, viral proteins and plasmid proteins, cellular organization control, subcellular localization, regulation of protein activity, proteins with binding function or cofactor requirement, and/or transport facilitation.

13. A method of generating the population of transgenic plants of claim 1, comprising:
   a) providing a known codogenic gene segment that encodes one protein of a cellular donor organism and integrating one or more than one copy of the codogenic gene segment into the genome of at least one plant;
   b) providing another known codogenic gene segment that encodes another protein of the cellular donor organism and integrating one or more than one copy of the other codogenic gene segment into the genome of another plant; and
   c) repeating step b) so that the resulting plurality of transgenic plants as a whole comprises at least 50% of all codogenic gene segments that encode a protein of the cellular donor organism;
   wherein each plant contains one or more than one copy of one codogenic gene segment of a cellular donor organism that encodes one protein of the cellular donor organism, but has integrated no other codogenic gene segment encoding another protein of the cellular donor organism;
   wherein said plurality of transgenic plants as a whole comprises at least 50% of all codogenic gene segments that encode a protein of the cellular donor organism, and wherein the codogenic gene segment comprises a start codon and a stop codon that define an open reading frame encoding the protein so that the open reading frame is transcribed and translated.

14. The method of claim 13, wherein bacteria from the genus *Agrobacterium* are transformed with one or more of the codogenic gene segments.

15. The method of claim 14, wherein the bacterium is *Agrobacterium tumefaciens*.

16. The method of claim 13, wherein the codogenic gene segment is integrated into the genome of said at least one plant by:
   allowing agrobacteria that are transformed with the codogenic gene segments to act on the plant or suitable biological material therefrom; and
   obtaining the transgenic plant or suitable biological material therefrom.

17. The method of claim 13, wherein the codogenic gene segment is integrated into the genome of said at least one plant by:
   allowing agrobacteria that are transformed with the codogenic gene segments to act in *planta*.

18. The method of claim 16, further comprising planting seeds of the plants treated with agrobacteria subjecting the seeds to selective conditions, and obtaining transformed plants or suitable biological material therefrom.

19. A method of generating the population of transgenic plants of claim 1, comprising: providing at least 50% of all of the codogenic gene segments encoding a protein of a cellular donor organism; and
   integrating said codogenic gene segments encoding a protein into the genome of at least one plant, wherein one or more copies of a single specific codogenic gene segment encoding a protein but no other codogenic gene segment encoding another protein of the cellular donor organism are integrated into a plant, resulting in a plurality of transgenic plants by:
   a) providing a known codogenic gene segment that encodes one protein of a cellular donor organism and integrating one or more than one copy of the codogenic gene segment into the genome of at least one plant;
   b) providing another known codogenic gene segment that encodes another protein of the cellular donor organism and integrating one or more than one copy of the other codogenic gene segment into the genome of another plant; and
   c) repeating step b) so that the resulting plurality of transgenic plants as a whole comprises at least 50% of all codogenic gene segments that encode a protein of a cellular donor organism;
   wherein said plurality of transgenic plants as a whole comprises at least 50% of all codogenic gene segments that encode a protein of a cellular donor organism, and wherein the integrated codogenic gene segment comprises a start codon and a stop codon that define an open reading frame encoding the protein and is capable of expressing a product.

20. A method for identifying stress tolerant transgenic plants comprising exposing the population of transgenic plants of claim 1 to stress conditions and identifying the transgenic plants exhibiting stress tolerance when compared to wild-type plants subjected to the same stress conditions.

21. The method of claim 20, wherein the stress conditions is low-temperature stress or drought stress.

22. A population of transgenic plants that consists of a plurality of transgenic plants of which each plant has integrated into its genome one or more than one copy of one codogenic gene segment of a cellular donor organism that encodes one protein of the cellular donor organism, but has integrated no other codogenic gene segment encoding another protein of the cellular donor organism,
   wherein the integrated codogenic gene segment comprises a start codon and a stop codon that define an open reading frame encoding the protein;
   wherein the integrated codogenic gene segment is operably linked to a regulatory sequence so that the open reading frame is transcribed and translated; wherein said plurality of transgenic plants as a whole comprises at least 50% of all codogenic gene segments that encode a protein of the cellular donor organism; and wherein the plurality of transgenic plants is obtained by
   a) providing a known codogenic gene segment that encodes one protein of a cellular donor organism and integrating one or more than one copy of the codogenic gene segment into the genome of a plant;
   b) providing another known codogenic gene segment that encodes another protein of the cellular donor organism and integrating one or more than one copy of the other codogenic gene segment into the genome of another plant;
   c) repeating step b) so that the resulting plurality of transgenic plants as a whole comprises at least 50% of all codogenic gene segments that encode a protein of the cellular donor organism; wherein the proteins are proteins that are expressed in the cellular donor organism.

23. A population of transgenic plants that consists of a plurality of transgenic plants of which each plant has integrated into its genome one or more than one copy of one codogenic gene segment of a cellular donor organism that encodes one protein of the cellular donor organism, but has integrated no other codogenic gene segment encoding another protein of the cellular donor organism,
   wherein the integrated codogenic gene segment comprises a start codon and a stop codon that define an open reading frame encoding the protein;
   wherein the integrated codogenic gene segment is operably linked to a regulatory sequence so that the open reading frame is transcribed and translated; wherein said plurality of transgenic plants as a whole comprises at least 50% of all codogenic gene segments that encode a protein of the cellular donor organism; and wherein the plurality of transgenic plants is obtained by
   a) providing a known codogenic gene segment that encodes one protein of a cellular donor organism and integrating one or more than one copy of the codogenic gene segment into the genome of a plant;
   b) providing another known codogenic gene segment that encodes another protein of the cellular donor organism and integrating one or more than one copy of the other codogenic gene segment into the genome of another plant;
   c) repeating step b) so that the resulting plurality of transgenic plants as a whole comprises at least 50% of all codogenic gene segments that encode a protein of the cellular donor organism; wherein the proteins are full-length proteins.

24. The population of claim 1, wherein the protein sequence of the proteins is available from a public gene database selected from the group consisting of the EMBL database, the GenBank database, the PIR database, the SGD database, the MIPS database, the GenProtEC database, and the TAIR database.

25. The population of claim 1, wherein the cellular donor organism is selected from the group of microorganisms consisting of *Acetobacter* (subgen. Acetobacter) *aceti*, *Acidithiobacillus ferrooxidans*, *Acinetobacter* sp., *Actinobacillus* sp.,

*Aeromonas salmonicida, Agrobacterium tumefaciens, Aquifex aeolicus, Arcanobacterium pyogenes,* Aster yellows phytoplasma, *Bacillus* sp., *Bifidobacterium* sp., *Borrelia burgdorferi, Brevibacterium Brucella melitensis, Buchnera* sp., *Butyrivibrio fibrisolvens, Campylobacter jejuni, Caulobacter crescentus, Chlamydia* sp., *Chlamydophila* sp., *Chlorobium limicola, Citrobacter rodentium, Clostridium* sp., *Comamonas testosteroni, Corynebacterium* sp., *Coxiella burnetii, Deinococcus radiodurans, Dichelobacter nodosus, Edwardsiella ictaluri, Enterobacter* sp., *Erysipelothrix rhusiopathiae, Escherichia coli, Flavobacterium* sp., *Francisella tularensis, Frankia* sp. CpI1, *Fusobacterium nucleatum, Geobacillus stearothermophilus, Gluconobacter oxydans, Haemophilus* sp., *Helicobacter pylori, Klebsiella pneumoniae, Lactobacillus* sp., *Lactococcus lactis, Listeria* sp., *Mannheimia haemolytica, Mesorhizobium loti, Methylophaga thalassica, Microcystis aeruginosa, Microscilla* sp. PRE1, *Moraxella* sp. TA144, *Mycobacterium* sp., *Mycoplasma* sp., *Neisseria* sp., *Nitrosomonas* sp., *Nostoc* sp. PCC 7120, *Novosphingobium aromaticivorans, Oenococcus oeni, Pantoea citrea, Pasteurella multocida, Pediococcus pentosaceus, Phormidium foveolarum, Phytoplasma* sp., *Plectonema boryanum, Prevotella ruminicola, Propionibacterium* sp., *Proteus vulgaris, Pseudomonas* sp., *Ralstonia* sp., *Rhizobium* sp., *Rhodococcus equi, Rhodothermus marinus, Rickettsia* sp., *Riemerella anatipestifer, Ruminococcus flavefaciens, Salmonella* sp., *Selenomonas ruminantium, Serratia entomophila, Shigella* sp., *Sinorhizobium meliloti, Staphylococcus* sp., *Streptococcus* sp., *Streptomyces* sp., *Synechococcus* sp., *Synechocystis* sp. PCC 6803, *Thermotoga maritima, Treponema* sp., *Ureaplasma urealyticum, Vibrio cholerae, Vibrio parahaemolyticus, Xylella fastidiosa, Yersinia* sp., and *Zymomonas mobilis.*

26. The population of claim 1, where the population comprises at least 3000 different codogenic gene segments from *Saccharomyces cerevisiae* or at least 3000 different codogenic gene segments from *E. coli.*

27. The population of claim 1, wherein the codogenic gene segments include codogenic gene segments selected from the codogenic gene segments shown in FIG. 1 or FIG. 2.

* * * * *

UNITED STATES PATENT AND TRADEMARK OFFICE
CERTIFICATE OF CORRECTION

PATENT NO. : 8,247,652 B2
APPLICATION NO. : 10/508264
DATED : August 21, 2012
INVENTOR(S) : Astrid Blau et al.

Page 1 of 1

It is certified that error appears in the above-identified patent and that said Letters Patent is hereby corrected as shown below:

In the claims:

In Claim 25, in column 27, on line 4, "*burgdorferi, Brevibacterium Brucella melitensis, Buchnera*" should read -- *burgdorferi, Brevibacterium linens, Brucella melitensis, Buchnera* --.

Signed and Sealed this
Twenty-third Day of April, 2013

Teresa Stanek Rea
*Acting Director of the United States Patent and Trademark Office*